United States Patent
Stefano et al.

(10) Patent No.: US 8,865,696 B2
(45) Date of Patent: *Oct. 21, 2014

(54) MORPHINE AND MORPHINE PRECURSORS

(71) Applicant: The Research Foundation for the State University of New York, Albany, NY (US)

(72) Inventors: George B. Stefano, Melville, NY (US); Patrick Cadet, Elmont, NY (US); Kirk J. Mantione, Patchogue, NY (US); Wei Zhu, West Babylon, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/924,211

(22) Filed: Jun. 21, 2013

(65) Prior Publication Data

US 2013/0309326 A1 Nov. 21, 2013

Related U.S. Application Data

(63) Continuation of application No. 12/904,373, filed on Oct. 14, 2010, now Pat. No. 8,481,559, which is a continuation of application No. 11/576,448, filed as application No. PCT/US2005/035628 on Sep. 30, 2005, now abandoned.

(60) Provisional application No. 60/714,769, filed on Sep. 6, 2005, provisional application No. 60/615,048, filed on Oct. 1, 2004.

(51) Int. Cl.
*A61K 31/555* (2006.01)
*A61K 31/44* (2006.01)

(52) U.S. Cl.
USPC .......................... 514/187; 514/282; 514/307

(58) Field of Classification Search
USPC ......................................... 514/187, 282, 307
See application file for complete search history.

(56) References Cited

U.S. PATENT DOCUMENTS

| | | | |
|---|---|---|---|
| 3,894,027 A | 7/1975 | Sohar et al. |
| 4,873,191 A | 10/1989 | Wagner et al. |
| 5,116,847 A | 5/1992 | Gilbert et al. |
| 5,225,440 A | 7/1993 | London et al. |
| 5,580,859 A | 12/1996 | Felgner et al. |
| 5,589,466 A | 12/1996 | Felgner et al. |
| 5,849,761 A | 12/1998 | Yaksh |
| 5,879,705 A | 3/1999 | Heafield et al. |
| 5,976,568 A | 11/1999 | Riley |
| 6,124,282 A | 9/2000 | Sellers et al. |
| 6,403,602 B1 | 6/2002 | Crooks et al. |
| 6,451,341 B1 | 9/2002 | Slaga et al. |
| 6,524,805 B1 | 2/2003 | Stefano et al. |
| 8,481,559 B2 | 7/2013 | Stefano et al. |
| 2003/0021949 A1 | 1/2003 | Tomita et al. |
| 2003/0087896 A1 | 5/2003 | Glover |
| 2003/0175822 A1 | 9/2003 | Stefano et al. |
| 2003/0219494 A1 | 11/2003 | Smith et al. |
| 2006/0088607 A1 | 4/2006 | Stefano et al. |
| 2007/0087390 A1 | 4/2007 | Stefano et al. |
| 2008/0221143 A1 | 9/2008 | Stefano et al. |
| 2011/0130356 A1 | 6/2011 | Stefano et al. |

FOREIGN PATENT DOCUMENTS

WO    WO 98/33937    9/1998

OTHER PUBLICATIONS

Ahmed et al. "Gender and risk of autoimmune diseases: possible role of estrogenic compounds," *Environ Health Perspect.*, 1999, 107(Suppl 5):681-686.
Bare et al. "Expression of two variants of the human μ opioid receptor mRNA in SK-N-SH cells and human brain," *FEBS Letters*, 1994, 354:213-216.
Bidlack et al. "Opiod Rreceptors and signaling on Cells from the Immune System," *J Neuroimmune Pharmacol.*, 2006, 1:260-269.
Bilfinger and Kushnerik. "The use of morphine in surgery: an overview," *Adv. Neuroimmunol.*, 1994, 4:133-144.
Bilfinger et al. "Cryopreserved Veins in Myocardial Revascularization: Possible Mechanism for Their Increased Failure," *Ann. Thorac. Surg.*, 1997, 63:1063-1069.
Carter and Medzihradsky. "Go mediates the coupling of the μ opioid receptor to adenylyl cyclase in cloned neural cells and brain," *PNAS USA*, 1993, 90:4062-4066.
Cruciani et al. "Presence in neuroblastoma cells of a mu 3 receptor with selectivity for opiate alkaloids but without affinity for opioid peptides," *Brain Res.*, 1994, 667(2):229-237.
Cutolo et al. "Sex hormones and rheumatoid arthritis," *Autoimmunity Reviews*, 2002, 1:284-289.
Cutolo et al. "Synovial fluid estrogens in rheumatoid arthritis," *Autoimmunity Reviews*, 2004, 3(3):193-198.
Fox-Threlkeld et al. "Identification of Mechanisms and Sites of Actions of Mu and Delta Opioid Receptor Activation in the Canine Intestine," *J. Pharmacol. Exp. Ther.*, 1994, 268(2):689-700.
Genbank Accession No. L25119 dated Aug. 8, 1994, 2 pages.
Gossler et al. "Transgenesis by means of blastocyst-derived embryonic stem cell lines," *Proc. Natl. Acad. Sci. USA*, 1986, 83:9065-9069.
Graham et al. "Cannabinoid receptors: A brief history and 'what's hot'," *Front in Biosci.*, 2009, 14:944-957.
Hopman et al. "Effect of increasing oral doses of loperamide on gallbladder motility in man," *Br. J. Clin. Pharmac.*, 1990, 29:55-60.
Hoskin et al. "The bioavailability an dpharmacokinetics of morphine after intravenous, oral and buccal administration in healthy volunteers," *Br. J. Clin. Pharmac.*, 1989, 27:499-205.

(Continued)

*Primary Examiner* — Kevin E Weddington
(74) *Attorney, Agent, or Firm* — Fish & Richardson P.C.

(57) ABSTRACT

Methods and materials related to the use of morphine, morphine precursors (e.g., reticuline), and inhibitors of morphine synthesis or activity to treat diseases, to reduce inflammation, or to restore normal function are provided.

16 Claims, 54 Drawing Sheets

(56) References Cited

OTHER PUBLICATIONS

Iuvone et al. "Opioids Inhibit the Induction of Nitric Oxide Synthase in J774 Macrophages," *Biochem. Biophys. Res. Comm.*, 1995, 212(3):975-980.

Lantin-Hermoso et al. "Estrogen acutely stimulates nitric oxide synthase activity in fetal pulmonary artery endothelium," *Am. J. Phys.*, 1997, 273(1, Part 1):L119-L126.

Lo. "Transformation by Iontophoretic Microinjection of DNA: Multiple Integrations Without Tandem Insertions," *Mol. Cell. Biol.*, 1983, 3(10):1803-1814.

Makman et al. "Properties of 1-13 Opiate Alkaloid Receptors in Macrophages, Astrocytes, and HL-60 Human Promyelocytic Leukemia Cells," *Adv. Exp. Med. Biol.*, 1998, 437:137-148.

Mantione et al. "Morphine 6 glucuronide stimulates nitric oxide release in mussel neural tissues: evidence for a morphine 6 glucuronide opiate receptor subtype," *Cell Mol. Life Sci.*, 2002, 59:570-574.

NCI Drug dictionary, www.cancer.gov/Templates/drugdictionary, downloaded Aug. 10, 2009, 1 page.

Raynor et al. "Characterization of the Cloned Human Mu Opioid Receptor," *J. Pharm. Exp. Ther.*, 1995, 272:423-428.

Richardson et al. Cannabinoids Reduce Hyperalgesia and Inflammation Via Interaction With Peripheral CB1 Receptors, *Pain*, 1998, 75:111-119.

Schnieke et al. "Human Factor IX Transgenic Sheep Produced by Transfer of Nuclei from Transfected Fetal Fibroblasts," *Science*, 1997, 278:2130-2133.

Sedqi et al. "Complementary DNA Cloning of a µ-Opioid Receptor from Rat Peritoneal Macrophages," *Biochem. Biophys. Res. Comm.*, 1995, 209(2):563-574.

Spencer et al. "Mobilization of Ca+2 from intracellular stores in transfected neuro2a cells by activation of multiple opioid receptor subtypes," *Biochem Pharmacol.*, 1997, 54:809-818.

Stefano et al. "Opioid Inhibition of Dopamine Release from Nervous Tissue of *Mytilus edulis* and *Octopus bimaculatus*," *Science*, 1981, 213(4503):928-930.

Stefano et al. "Presence of the 1-13 Opiate Receptor in Endothelial Cells," *J. Biol. Chem.*, 1995, 270 (51):30290-30293.

Stefano et al., "Morphine stimulates INOS expression via a rebound from inhibition in human macrophages: nitric oxide involvement," *International Journal of Immunopathology and Pharmacology*, 2001, 14(3):129-138.

Thompson et al. "Germ Line Transmission and Expression of a Corrected HPRT Gene Produced by Gene Targeting in Embryonic Stem Cells," *Cell*, 1989, 56:313-321.

Uhl et al. "Theµ opiate receptor as a candidate gene for pain: Polymorphisms, variations in expression, nociception, and opiate responses," *PNAS*, 1999, 7752-7755.

Van der Putten et al. "Efficient insertion of genes into the mouse germ line via retroviral vectors," *Proc. Natl. Acad. Sci. USA*, 1985, 82:6148-6152.

Vidal et al. "Interleukin-1 induces the expression of I-1 opioid receptors in endothelial cells," *Immunopharmacology*, 1998, 38:261-266.

Walker et al. "Effect of mu-opioids morphine and buprenorphine on the development of adjuvant arthritis in rat," *Inflamm Res.*, 1996. 45(11):557-563.

Watson et al. "Membrane estrogen and glucocorticoid receptors-implications for hormonal control of immune function and autoimmunity," *International immunopharmacology*, 2001, 1(6):1049-1063.

Wendel and Hoehe. "The humanµ receptor gene: 5' regulatory and intronic sequences," *J. Mol. Med.*, 1998, 76:525-532.

Woods et al. "Behavioral Effects of Thebaine in the Rhesus Monkey," *Pharmacology Biochemistry & Behavior*, 1981, vol. 14, pp. 805-809.

Zhao and Bhargava. "Nitric Oxide Synthase Inhibition Attenuates Tolerance to Morphine but not to [D-Ala2,Glu4] Deltorphin II, a o2-0pioid Receptor Agonist in Mice," *Peptides*, 1996, 17(4):619-623.

Berg et al. "Reduction of dyskinesia and induction of akinesia induced by morphine in two Parkinsonian patients with severe sciatica," *J. Neural. Transm.*, 1999, 106:725-728.

Samadi et al. "The opioid agonist morphine decreases the dyskinetic response to dopaminergic agents in parkinsonian monkeys," *Neurobiol. Dis.*, 2004,16:246-253.

Bilfinger et al., "Neuroimmune implications of cardiopulmonary bypass," *Adv. Neuroimmunol.*, 1993, 3:277-288.

Bird et al. "Human NCI-H295 Adrenocortical Carcinoma Cells: A Model for Angiotensin-II-Responsive Aldosterone Secretion," *Endocrinology*, 1993, 133(4):1555-1561.

Brochmann-Hanssen and Nielsen. "(+)-Reticuline—a new opium alkaloid." *Tetrahedron Lett.*, 1965, 18:1271-1274.

Cadet and Stefano. "*Mytilus edulis* pedal ganglia expressµ opiate receptor transcripts exhibiting high sequency identity with human neuronalµ 1," *Brain Res. Mol. Brain Res.*, 1999, 74:242-246.

Cadet et al. "Endogenous morphinergic signaling and tumor growth," *Front. Biosci.*, 2004, 9:3176-3186.

Cadet et al. "Molecular Identification and Functional Expression ofµ 3, a Novel Alternatively Spliced Variant of the Humanµ Opiate Receptor Gene," *J. Immunol.*, 2003, 170(10):5118-5123.

Fimiani et al. "Morphine and Anandamide Stimulate Intracellular Calcium Transients in Human Arterial Endothelial Cells: Coupling to Nitric Oxide Release," *Cellular Signaling*, 1999, 11(3):189-193.

Gazdar et al. "Establishment and characterization of a human adrenocortical carcinoma cell line that expresses multiple pathways of steroid biosynthesis," *Cancer Res.*, 1990, 50(17):5488-5496.

GenBank Accession No. M20403, dated Nov. 2, 1994, 2 pages.

Hughes et al. "Detection of immunoreactive Interleukin-6 in invertebrate hemolymph and nervous Tissue," *Prog. Neuroimmune Endocrinol.*, 1991, 4:234-239.

Hughes et al. "Interaction of immunoactive monokines (IL-1 and TNF) in the bivalve mollusk *Mytilus edulis*," *Proc. Natl. Acad. Sci. USA*, 1990, 87:4426-4429.

Hughes et al. "Lipopolysaccharide and opioids activate distinct populations of *Mytilus edulis* Immunocytes," *Cell. Tiss. Res.*, 1991, 264:317-320.

Hughes et al. "LPS stimulated invertebrate hemocytes: a role for immunoreactive TNF and IL-1," *Dev. Comp. Immunol*, 1991, 15:117-122.

Hughes et al. "Similarities of signal systems in vertebrates and invertebrates: Detection, action, and interactions of immunoreactive monokines in the mussel, *Mytilus edulis*," *Adv. Neuroimmunol.*, 1991,1:59-70.

Kotamraju et al. "Nitric oxide inhibits H20 2-induced transferrin receptor-dependent apoptosis in endothelial cells: Role of ubiquitin-proteasome pathway," *Proc. Natl. Acad. Sci. USA*, 2003, 100(19):10653-10658.

Liu et al. "Morphine stimulates nitric oxide release from invertebrate microglia," *Brain Res.*, 1996, 722(1,2): 125-131.

Magazine et al. "Morphine-induced conformational changes in human monocytes, granulocytes, and endothelial cells and in invertebrate immunocytes and microglia are mediated by nitric oxide," *J. Immunol.*, 1996, 156:4845-4850.

Makman et al. "Human Granulocytes Contain an Opiate Alkaloid-Selective Receptor Mediating Inhibition of Cytokine-Induced Activation and Chemotaxis," *J. Immunol.*, 1995, 154:1323-1330.

Olsen et al. "Human gliomas contain morphine," *Med. Sci. Monit.*, 2005, 11(5)MSI8-MS21.

Paeman et al. "Glial localization of interleukin-la in invertebrate ganglia," *Cell. Mol. Neurobiol.*, 1992,12:463-472.

Poeaknapo. "Mammalian morphine: de novo formation of morphine in human cells," *Med. Sci. Monit.*, 2005, 11(5):MS6-MS17.

Rainey et al. "The NCI-H295 cell line: a pluripotent model for human adrenocortical studies," *Mol. Cell. Encocrinol.*, 1994,100:45-50.

Schön et al. "Microscopic computer-assisted analysis of conformational state: reference to neuroimmunology," *Adv. Neuroimmunol.*, 1991, 1:252-259.

Shipp et al. "Downregulation of enkephalin-mediated inflammatory response by CD10/neutral endopeptidase 24.11," *Nature*, 1990, 347:394-396.

Sonetti et al. "Endogenous morphine and ACTH association in neural tissues," *Med. Sci. Monit.*, 2005, 11(5):MS22-MS30.

(56) References Cited

OTHER PUBLICATIONS

Stefano and Bilfinger. "Human neutrophil and macrophage chemokinesis induced by 31, cardiopulmonary bypass: Loss of DAME and IL-1 chemotaxis," *J. Neuroimmunol.*, 1993,47:189-198.
Stefano et al. "Electric Field Exposure Activates Immunocytes: Evidence for Calcium Dependency," *Electro-Magnetobiol.*, 1994, 13(2):123-136.
Stefano et al. "Morphine- and anandamide-stimulated nitric oxide production inhibits presynaptic dopamine release," *Brain Res.*, 1997, 763:63-68.
Stefano et al. "Morphine Enhances Nitric Oxide Release in the Mammalian Gastrointestinal Tract Via the mu3 opiate receptor subtype: A hormonal Role for Endogenous Morphine," *J. Physiol. Pharmacol.*, 2004, 55(1-Pt2):279-288.
Stefano et al. "Opiate-like substances in an invertebrate, and opiate receptor on invertebrate and human immunocytes, and a role in immunosuppression," *Proc. Natl. Acad. Sci. USA*, 1993, 90:11099-11103.
Stefano et al. "Opioid induction of immunoreactive interleukin-1 in *Mytilus edulis* and human immunocytes: an interleukin-1-like substance in invertebrate neural tissue," *J. Neuroimmunol.*, 1991, 32:29-34.
Stefano et al., "Autoimmunoregulation: differential modulation of CD 10/neutral endopeptidase 24.11 by tumor necrosis factor and neuropeptides," *J. Neuroimmunol.*, 1992, 41 :9-14.
Stefano et al., [D-Ala$^2$]Deltorphin I binding and pharmacological evidence for a special subtype of δ opioid receptor on human and invertebrate immune cells, *Proc. Natl. Acad. Sci. USA*, 1992, 89:9316-9320.
Stefano, "Advances in Endogenous Morphine," *Med. Sci. Monit.*, 2005, 11(5):ED1-1.
Szucs et al. "Modulation of Voltage-Activated Ion Currents on Identified Neurons of *Helix pomatia* L. by Interleukin-1," *Cell. Mol. Neurobiol.*, 1992, 12(5):429-438.
Xu et al. "Intravenous Morphine Increases Release of Nitric Oxide from Spinal Cord by an α-Adrenergic and Cholinergic Mechanism," *J. Neurophysiol.*, 1997, 78(4):2072-2078.
Zhu et al, "Identification of morphine and morphine-6-glucuronide in the adrenal medullary chromaffm PC-12 cell line by nano-electrospray ionization double quadrupole orthogonalacceleration time-of-flight mass spectrometry," *Eur. J. Mass Spectrom.*, 2001, 7:25-28.
Zhu et al, "In vivo and in vitro L-DOPA and reticulin exposure increases ganglionic morphine levels," *Med. Sci. Monit.*, 2005, 11(5): MS1-MS5.
Zhu et al, "Opiate Alkaloids and Nitric Oxide Production in the Nematode *Ascaris suum,*" *J. Parasitol.*, 2004, 90(1): 15-22.
Zhu et al, "Presence of isoquinoline alkaloids 23:329-334 in molluscan ganglia," *Neuroendocrinol. Lett.*, 2002, 23:329-334.
Zhu et al, "Presence of morphine and morphine-6-glucuronide in the marine mollusk *Mytilus edulis* ganglia determined by GCIMS and Q-TOF-MS. Starvation increases opiate alkaloid evels," *Mol. Brain Res.*, 2001, 88:15-160.
Zhu et al, "Presence of reticuline in rat brain: a pathway for morphine biosynthesis" *Mol. Brain Res.*, 2003, 117:83-90.
Zhu et al, "Reticuline Exposure to Invertebrate Ganglia Increases Endogenous Morphine Levels," *Neuroendocrinol. Lett.*, 2004, 25(4):323-330.
Zhuge and Yu. "Three new alternative splicing variants of human cytochrome P450 2D6 mRNA in human extratumoral liver tissue," *World J. Gastroenterol.*, 2004, 10(22):3356-3360.
Authorized Officer B. Kwon. International Search Report and Written Opinion in International Application No. PCT/US05/35628, mailed Aug. 8, 2006, 9 pages.
Authorized Officer Y. Cussac. International Preliminary Report on Patentability in International Application No. PCT/US05/35628, issued Apr. 3, 2007, 5 pages.
Authorized Officer S. Tang. International Search Report in International Application No. PCT/US98/23944, mailed Mar. 2, 1999, 5 pages.
Supplementary European Search Report in EP05810196, mailed Sep. 1, 2009, 9 pages.
Japanese Office Action in Japanese Application No. 2007-534882, dated Jan. 18, 2012, 3 pages.
USPTO Non-final Office Action in U.S. Appl. No. 11/465,790, mailed Aug. 20, 2009, 16 pages.
USPTO Non-final Office Action in U.S. Appl. No. 10/338,306, mailed Apr. 18, 2006, 9 pages.
USPTO Non-final Office Action in U.S. Appl. No. 09/530,880, mailed Dec. 4, 2001, 5 pages.
USPTO Final Office Action in U.S. Appl. No. 09/530,880, mailed Jun. 18, 2002, 4 pages.
USPTO Non-final Office Action in U.S. Appl. No. 11/241,248, mailed Mar. 19, 2009, 13 pages.
USPTO Final Office Action in U.S. Appl. No. 11/241,248, mailed Sep. 2, 2009, 12 pages.
Fish & Richardson P.C. Amendment in Reply to Action dated Dec. 4, 2001 in U.S. Appl. No. 09/530,880, filed Mar. 8, 2002, 8 pages.
Fish & Richardson P.C., Amendment in Reply to Action dated Jun. 18, 2002 in U.S. Appl. No. 09/530,880, filed Sep. 13, 2002, 5 pages.
Fish & Richardson P.C., Amendment in Reply to Action dated Mar. 19, 2009, in U.S. Appl. No. 11/241,248, filed May 8, 2009, 9 pages.
European Office Action in European Application No. EP05810196, dated Dec. 7, 2009, 5 pages.
USPTO Non-final Office Action in U.S. Appl. No. 11/576,448, dated Apr. 14, 2010, 9 pages.
USPTO Non-final Office Action in U.S. Appl. No. 11/465,790, mailed Apr. 15, 2010, 17 pages.
Homayoun et al., "The role of nitric oxide in anticonvulsant and proconvulsant effects of morphine in mice," Epilepsy Research, 48:33-41, 2002.
USPTO Non-final Office Action in U.S. Appl. No. 11/241,249, dated Oct. 22, 2013, 28 pages.
USPTO Non-final Office Action in U.S. Appl. No. 12/904,373, dated Jun. 13, 2012, 11 pages.

ggccaaggggaaccctgagagcagcttcaatgatgagaacctgcgcatagtggtgctgacctgttctctgccgggatg
nnccaaggggaaccctgagagcagcttcaatgatgagaacctgcgcatagtggtgctgacctgttctctgccgggatg gtgaccacctcgaccacgctggcctggggc ctc c tgctcatgatc c tacatc -c ggatgtgcagcccg t gtc c aa c agga
gtgaccacctcgaccacgctggcctggggc atc n tgctcatgatc a tacatc tn ggatgtgcagcgccg g gtc - aa n agga gat c gac g acgtgataggcaggtgcgg c gaccagagatgggtgaccaggct c acatgcctacacaccactgccgtgat
gat t gac t acgtgataggcaggtgcgg a gaccagagatggtgaccaggct -

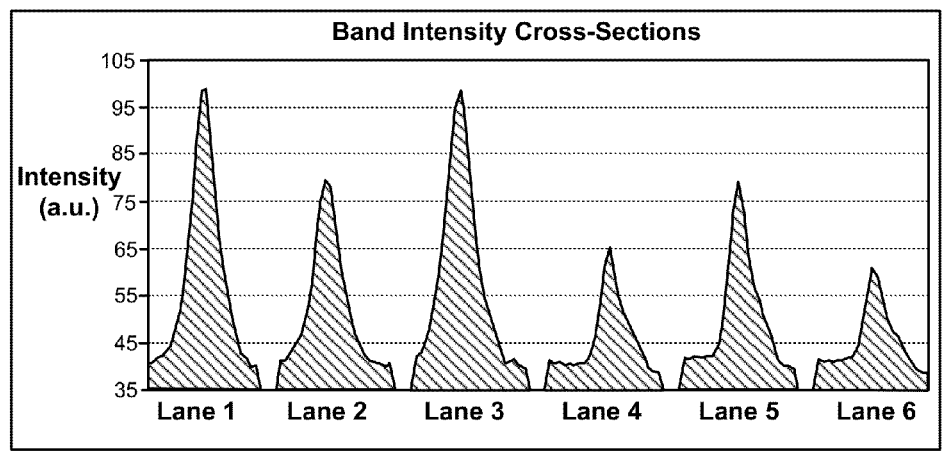
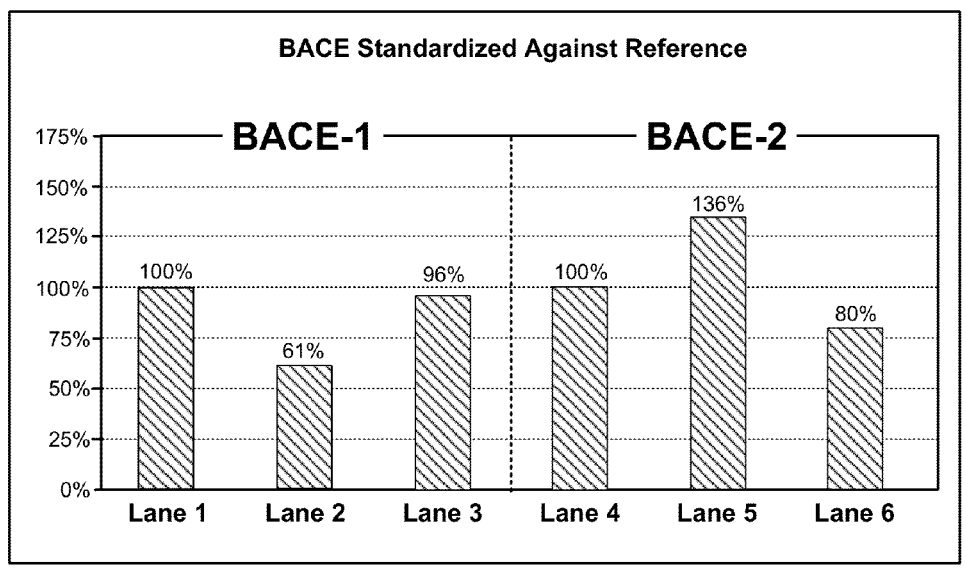
Figure 34

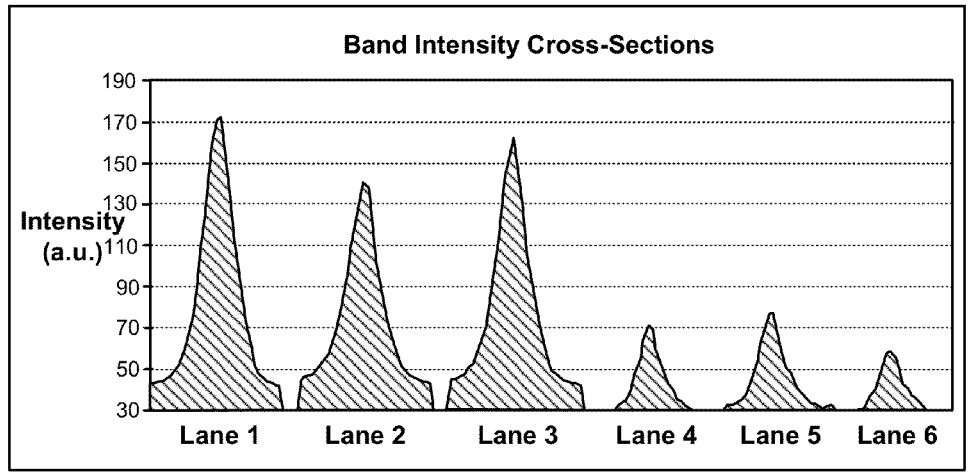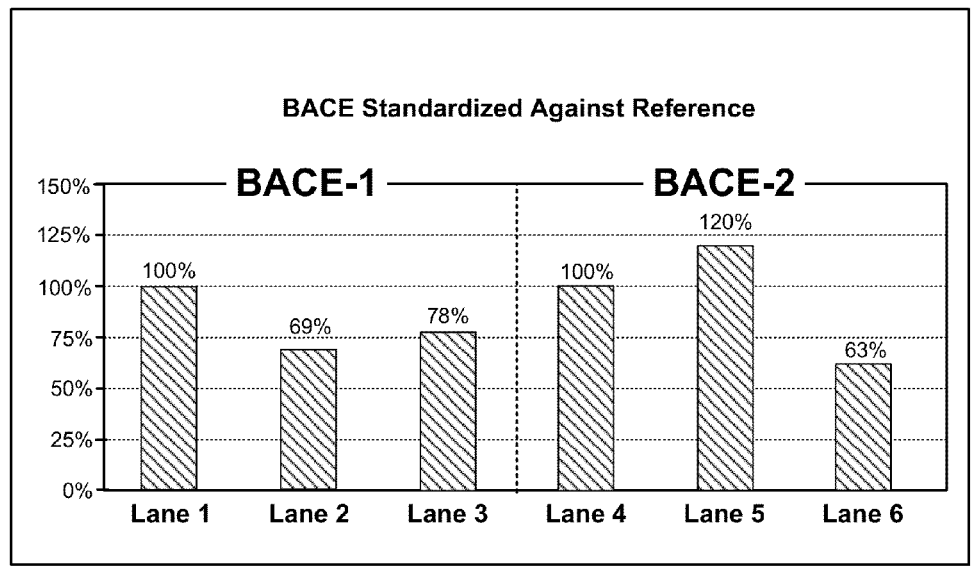
Figure 35

Page 1/2

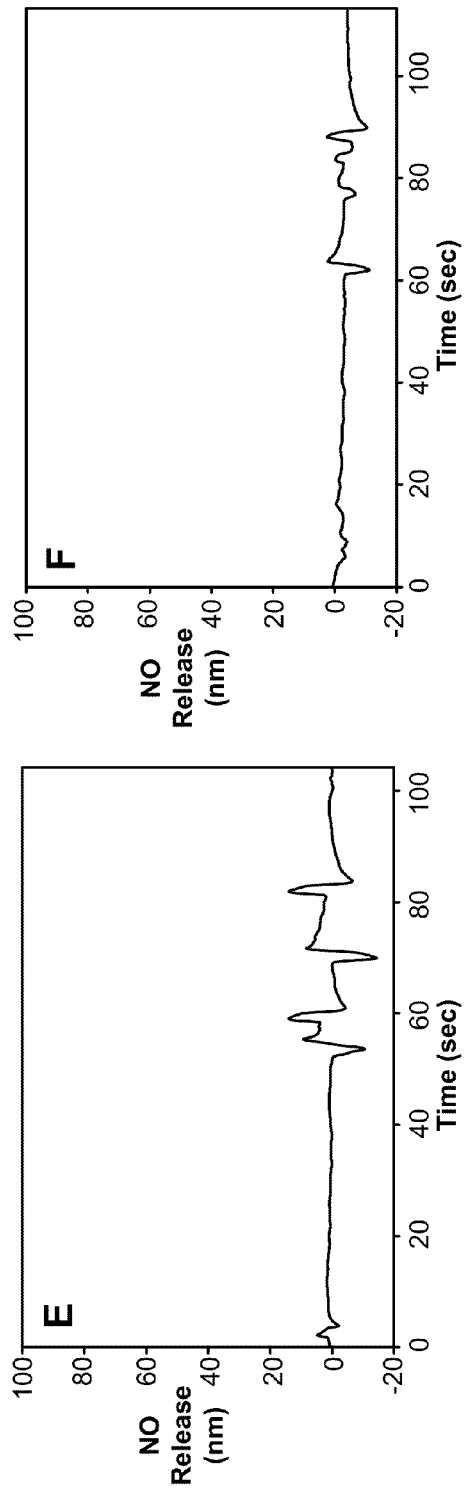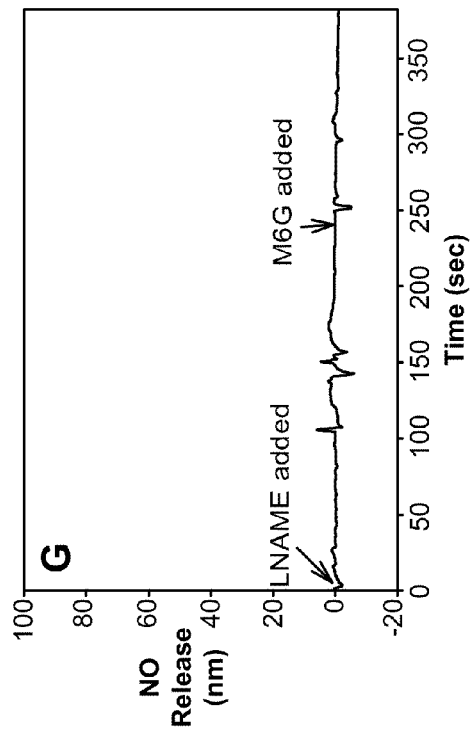
Figure 41
Page 2/2

Page 1/2

Page 2/2

MORPHINE AND MORPHINE PRECURSORS

CROSS-REFERENCE TO RELATED APPLICATIONS

This application is a continuation of U.S. application Ser. No. 12/904,373, filed Oct. 4, 2010, which is a continuation of U.S. application Ser. No. 11/576,448, filed Aug. 31, 2007, which is a U.S. National Stage application under 35 U.S.C. §371 and claims benefit under 35 U.S.C. §119(a) of International Application No. PCT/US2005/035628 having an International Filing Date of Sep. 30, 2005, which claims the benefit of U.S. Provisional Application Ser. No. 60/714,769, having a filing date of Sep. 6, 2005, and U.S. Provisional Application Ser. No. 60/615,048 having a filing date of Oct. 1, 2004. The disclosures of the prior applications are considered part of (and are incorporated by reference in) the disclosure of this application.

STATEMENT AS TO FEDERALLY SPONSORED RESEARCH

This invention was made with government support under grant numbers MH047392 and DA009010 awarded by the National Institutes of Health. The government has certain rights in the invention.

BACKGROUND

1. Technical Field

This document relates to methods and materials involved in using morphine, morphine precursors (e.g., reticuline), morphine-6β-glucuronide, and inhibitors of morphine synthesis or activity to treat mammals.

2. Background Information

Many people suffer from conditions such as depression, neurodegenerative diseases (e.g., Alzheimer's disease), pro-inflammatory diseases, autoimmune disorders, and atherosclerosis. In many cases, few, if any, successful treatments are available for these people.

Morphine is a powerful analgesic that is routinely used to reduce pain in humans. For example, surgery patients are typically instructed to take 5 to 10 mg of morphine per person to alleviate pain caused by the surgical procedure. In some cases, patients suffering from extreme pain (e.g., burn victims or cancer patients) are instructed to take higher doses of morphine. For moderate to severe pain, the optimal intramuscular dosage is considered to be 10 mg per 70 kg body weight every four hours. The typical dose range is from 5 to 20 mg every four hours, depending on the severity of the pain. The oral dose range is between 8 and 20 mg, but orally administered morphine has substantially less analgesic potency. Orally administered morphine can exhibit about one-tenth of the effect produced by subcutaneous injection of morphine since orally administered morphine is rapidly destroyed as it passes through the liver after absorption. The intravenous route is used primarily for severe post-operative pain or in an emergency. In such cases, the dose range is between 4 and 10 mg, and the analgesic effect ensues almost immediately.

SUMMARY

This document provides methods and materials related to using morphine, morphine-6β-glucuronide, morphine precursors (e.g., reticuline), inhibitors of morphine synthesis or activity, and inhibitors of dopamine synthesis to treat diseases, to reduce inflammation, or to restore normal function. For example, this document provides compositions containing morphine, morphine-6β-glucuronide, morphine precursors, inhibitors of morphine synthesis, inhibitors of morphine activity, inhibitors of dopamine synthesis, or combinations thereof. This document also provides methods for using such compositions (e.g., method for providing a mammal with a long-term, low level of morphine). As described herein, a long-term, low level of morphine can be achieved in a mammal by repeatedly administering a low dose of morphine, by repeatedly administering a morphine precursor, or by repeatedly administering a combination of morphine and morphine precursors. In some cases, inhibitors such as dopamine β-hydroxylase inhibitors can be used to inhibit the dopamine to norepinephrine step in adrenaline synthesis, which can result in an endogenous dopamine level increase as well as an endogenous morphine level increase.

Providing a mammal with a long-term, low level of morphine can allow the mammal to experience behavioral changes (e.g., a general overall calm feeling). In addition, providing a mammal with a long-term, low level of morphine can allow the mammal to experience reduced inflammatory responses and can allow the mammal to maintain an increased, basal level of constitutive nitric oxide release. In some cases, the compositions provided herein can be used to down regulate immune, vascular, neural, and gastrointestinal tissues via nitric oxide produced within a mammal. For example, the compositions provided herein can be used to reduce the excited state of inflamed gastrointestinal tissues in mammals having Crohn's disease.

The methods and materials provided herein also can be used to treat (e.g., reduce the severity of symptoms) neural conditions (e.g., schizophrenia, chronic pain, mania, depression, psychosis, paranoia, autism, stress, Alzheimer's disease, or Parkinson's disease), immune conditions (e.g., pro-inflammatory diseases, autoimmune disorders, histolytic medullary reticulosis, lupus, or arthritis), vascular conditions (e.g., atherosclerosis or neuronal vasculopathy), gastrointestinal conditions (e.g., colitis, Crohn's disease, or irritable bowel syndrome), or addiction (e.g., opiate addiction). For example, morphine or a morphine precursor such as reticuline, norlaudanosoline, L-DOPA, or codeine can be used to treat neural conditions such as neurovascular alterations involving hypothalamic hormone secretion (e.g., reproductive and growth hormones).

As disclosed herein, prolonged treatment with a low dose of morphine can result the continued positive effects of morphine such as nitric oxide release, without the need to escalate morphine dosages with time to achieve the same beneficial effects. In addition, the use of low doses of morphine can allow patients to experience the beneficial effects of morphine, while not experiencing possible negative effects of morphine (e.g., addiction or powerful analgesia). Likewise, treating patients with a morphine precursor such as reticuline can allow patients to experience the beneficial effects of morphine, while not experiencing possible negative effects of morphine (e.g., addiction or powerful analgesia). For example, using a morphine precursor such as reticuline can allow patients to receive a low dose of morphine indirectly with a reduced risk of overdosing.

In general, one aspect of this document features a method for inducing nitric oxide release from cells in a mammal. The method comprises, or consists essentially of, administering, to the mammal, a composition in an amount, at a frequency more frequent than once a week, and for a duration longer than one month, wherein the composition comprises, or consists essentially of, morphine or morphine-6β-glucuronide, and wherein the amount of the composition results in less than 0.05 mg of the morphine or morphine-6β-glucuronide being administered to the mammal per kg of body weight of the mammal per day. The cells can be immune cells. The mammal can be a human. The composition can contain a morphine precursor. The composition can be in the form of a tablet. The composition can contain selenium. The composition can contain arginine (e.g., L-arginine). The composition can contain a calcium source. The amount of the composition can result in less than 0.025 mg of the morphine or morphine-6β-glucuronide being administered to the mammal per kg of body weight of the mammal per day. The e amount of the composition can result in less than 0.01 mg of the morphine or morphine-6β-glucuronide being administered to the mammal per kg of body weight of the mammal per day. The frequency can be more frequent than four times a week. The frequency can be between two and five times a day. The frequency can be once a day. The duration can be longer than two months. The duration can be longer than three months. The composition can contain morphine. The composition can contain morphine-6β-glucuronide. The composition can contain morphine and morphine-6β-glucuronide.

In another embodiment, this document features a method for inducing nitric oxide release from cells in a mammal. The method comprises, or consists essentially of, administering, to the mammal, a composition in an amount, at a frequency more frequent than once a week, and for a duration longer than one month, wherein the composition comprises thebaine or codeine, and wherein the amount of the composition results in less than 0.05 mg of the thebaine or codeine being administered to the mammal per kg of body weight of the mammal per day. The cells can be immune cells. The mammal can be a human. The composition can contain morphine in an amount that results in less than 0.05 mg of the morphine being administered to the mammal per kg of body weight of the mammal per day. The composition can be in the form of a tablet. The composition can contain selenium. The composition can contain arginine (e.g., L-arginine). The composition can contain a calcium source. The amount of the composition can result in less than 0.01 mg of the thebaine or codeine being administered to the mammal per kg of body weight of the mammal per day. The amount of the composition can result in less than 0.005 mg of the thebaine or codeine being administered to the mammal per kg of body weight of the mammal per day. The frequency can be more frequent than four times a week. The frequency can be between two and five times a day. The frequency can be once a day. The duration can be longer than two months. The duration can be longer than three months. The composition can contain thebaine. The composition can contain codeine. The composition can contain thebaine and codeine.

In another embodiment, this document features a method for inducing nitric oxide release from cells in a mammal. The method comprises, or consists essentially of, administering, to the mammal, a composition in an amount, at a frequency more frequent than once a week, and for a duration longer than one month, wherein the composition comprises one or more agents selected from the group consisting of reticuline, norlaudanosoline, and salutaridine, and wherein the amount of the composition results in less than 1 mg of the one or more agents being administered to the mammal per kg of body weight of the mammal per day. The cells can be immune cells. The mammal can be a human. The composition can contain morphine in an amount that results in less than 0.05 mg of the morphine being administered to the mammal per kg of body weight of the mammal per day. The composition can be in the form of a tablet. The composition can contain selenium. The composition can contain arginine (e.g., L-arginine). The composition can contain a calcium source. The amount of the composition can result in less than 0.5 mg of the one or more agents being administered to the mammal per kg of body weight of the mammal per day. The amount of the composition can result in less than 0.05 mg of the one or more agents being administered to the mammal per kg of body weight of the mammal per day. The frequency can be more frequent than four times a week. The frequency can be between two and five times a day. The frequency can be once a day. The duration can be longer than two months. The duration can be longer than three months. The composition can contain reticuline, norlaudanosoline, and salutaridine.

In another embodiment, this document features a method for inducing nitric oxide release from cells in a mammal. The method comprises, or consists essentially of, administering, to the mammal, a composition in an amount, at a frequency more frequent than once a week, and for a duration longer than one month, wherein the composition comprises dopamine or L-DOPA, and wherein the amount of the composition results in less than 1 µg of the dopamine or L-DOPA being administered to the mammal per kg of body weight of the mammal per day. The cells can be immune cells. The mammal can be a human. The composition can contain morphine in an amount that results in less than 0.05 mg of the morphine being administered to the mammal per kg of body weight of the mammal per day. The composition can be in the form of a tablet. The composition can contain selenium. The composition can contain arginine (e.g., L-arginine). The composition can contain a calcium source. The amount of the composition can result in less than 0.5 mg of the one or more agents being administered to the mammal per kg of body weight of the mammal per day. The amount of the composition can result in less than 0.05 mg of the one or more agents being administered to the mammal per kg of body weight of the mammal per day. The frequency can be more frequent than four times a week. The frequency can be between two and five times a day. The frequency can be once a day. The duration can be longer than two months. The duration can be longer than three months. The composition can contain reticuline, norlaudanosoline, and salutaridine.

In another aspect, this document features a composition comprising, or consisting essentially of, morphine and selenium. The composition can contain between 35 µg and 700 µg of morphine. The composition can contain between 55 µg and 300 µg of selenium. The composition can contain arginine (e.g., L-arginine). The composition comprises between 1 mg and 500 mg of arginine. The composition can contain a calcium source. The composition can contain between 250 µg and 1.5 g (e.g., between 1 g and 1.3 g) of the calcium source. The calcium source can be calcium citrate. The composition can contain one or more agents selected from the group consisting of tyrosine, tyramine, phenylalanine, 3,4 dihydroxyphenyl pyruvate, dihydroxyphenyl acetaldehyde, dopamine, L-DOPA, reticuline, norlaudanosoline, salutaridine, thebaine, and codeine. The composition can contain one or more agents selected from the group consisting of CYP2D6 and CYP2D7 inhibitors.

In another embodiment, this document features a composition comprising, or consisting essentially of, morphine and arginine (e.g., L-arginine). The composition can contain between 35 µg and 700 µg of morphine. The composition can contain between 1 mg and 500 mg of arginine. The composition can contain a calcium source. The composition can contain between 250 µg and 1.5 g (e.g., between 1 g and 1.3 g) of the calcium source. The calcium source can be calcium citrate. The composition can contain one or more agents selected from the group consisting of tyrosine, tyramine, phenylalanine, 3,4 dihydroxyphenyl pyruvate, dihydroxyphenyl acetaldehyde, dopamine, L-DOPA, reticuline, norlaudanosoline, salutaridine, thebaine, and codeine. The composition can contain one or more agents selected from the group consisting of CYP2D6 and CYP2D7 inhibitors.

In another embodiment, this document features a composition for reducing the level of morphine produced in cells, wherein the composition comprises, or consists essentially of, L-DOPA and dopamine. The composition can contain between 25 mg and 500 mg (e.g., 250 mg) of L-DOPA. The composition can contain between 25 mg and 500 mg (e.g., 250 mg) of dopamine. The composition can contain an equal amount of L-DOPA and dopamine.

In another aspect, this document features a method for increasing production of morphine in a mammal. The method comprises, or consists essentially of, administering a composition to the mammal under conditions effective to increase the amount of morphine produced by cells within the mammal, wherein the composition comprises one or more agents selected from the group consisting of reticuline, norlaudanosoline, salutaridine, thebaine, and codeine. The cells can be immune cells. The mammal can be a human. The composition can contain morphine. The composition can be in the form of a tablet. The composition can contain selenium. The composition can contain arginine (e.g., L-arginine). The composition can contain a calcium source. The method can include, prior to the administering step, identifying the mammal as needing an increase in morphine. The method can include, after the administering step, monitoring the mammal to confirm an increase in morphine. The method can include administering the composition to the mammal at a frequency more frequent than once a month. The method can include administering the composition to the mammal at a frequency more frequent than once a week. The method can include administering the composition to the mammal at a frequency between once and five times a day. The method can include administering the composition to the mammal at a frequency more frequent than once a week and for a duration longer than one month. The duration can be longer than three months.

In another embodiment, this document features a method for treating a mammal having a condition selected from the group consisting of schizophrenia, mania, depression, psychosis, chronic pain, paranoia, autism, stress, Alzheimer's disease, Parkinson's disease, pro-inflammatory diseases, autoimmune disorders, histolytic medullary reticulosis, lupus, arthritis, atherosclerosis, neuronal vasculopathy, gastrointestinal conditions, and addiction. The method comprises, or consists essentially of, administering a composition to the mammal under conditions wherein the severity of a symptom of the condition is reduced, wherein the composition comprises one or more agents selected from the group consisting of reticuline, norlaudanosoline, salutaridine, thebaine, and codeine. The method can include, prior to the administering step, identifying the mammal as having the condition. The method can include, after the administering step, monitoring the mammal to confirm an reduction is the severity. The mammal can be a human. The composition can be administered orally. The composition can be administered to the mammal in an amount such that the mammal receives between about 1 and 5 mg of at least one of the one or more agents per kg body weight of the mammal. The composition can be administered to the mammal at a frequency more frequent than once a month. The composition can be administered to the mammal at a frequency between once and 5 times a day or week.

In another embodiment, this document features a method for treating a mammal having a condition selected from the group consisting of schizophrenia, mania, depression, psychosis, chronic pain, paranoia, autism, stress, Alzheimer's disease, Parkinson's disease, pro-inflammatory diseases, autoimmune disorders, histolytic medullary reticulosis, lupus, arthritis, atherosclerosis, neuronal vasculopathy, gastrointestinal conditions, and addiction. The method comprises, or consists essentially of, administering, to the mammal, a composition in an amount, at a frequency more frequent than once a week, and for a duration longer than one month, wherein the composition comprises morphine or morphine-6β-glucuronide, and wherein the amount of the composition results in less than 0.05 mg of the morphine or morphine-6β-glucuronide being administered to the mammal per kg of body weight of the mammal per day. The method can include, prior to the administering step, identifying the mammal as having the condition. The severity of a symptom of the condition can be reduced at a time point at least one month following an initial administration of the composition. The method can include, after the administering step, evaluating the mammal to confirm a reduction in the severity of a symptom of the condition. The mammal can be a human. The composition can be administered orally. The composition can be administered to the mammal at a frequency more frequent than once a week. The composition can be administered to the mammal at a frequency between once and 5 times a day or week. The composition can contain morphine. The composition can contain morphine-6β-glucuronide. The composition can contain morphine and morphine-6β-glucuronide.

In another aspect, this document features a dietary supplement comprising, or consisting essentially of, selenium, morphine, and arginine (e.g., L-arginine). The composition can contain any of the additional components described herein such as a morphine precursor or a calcium source.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

Figure 4:
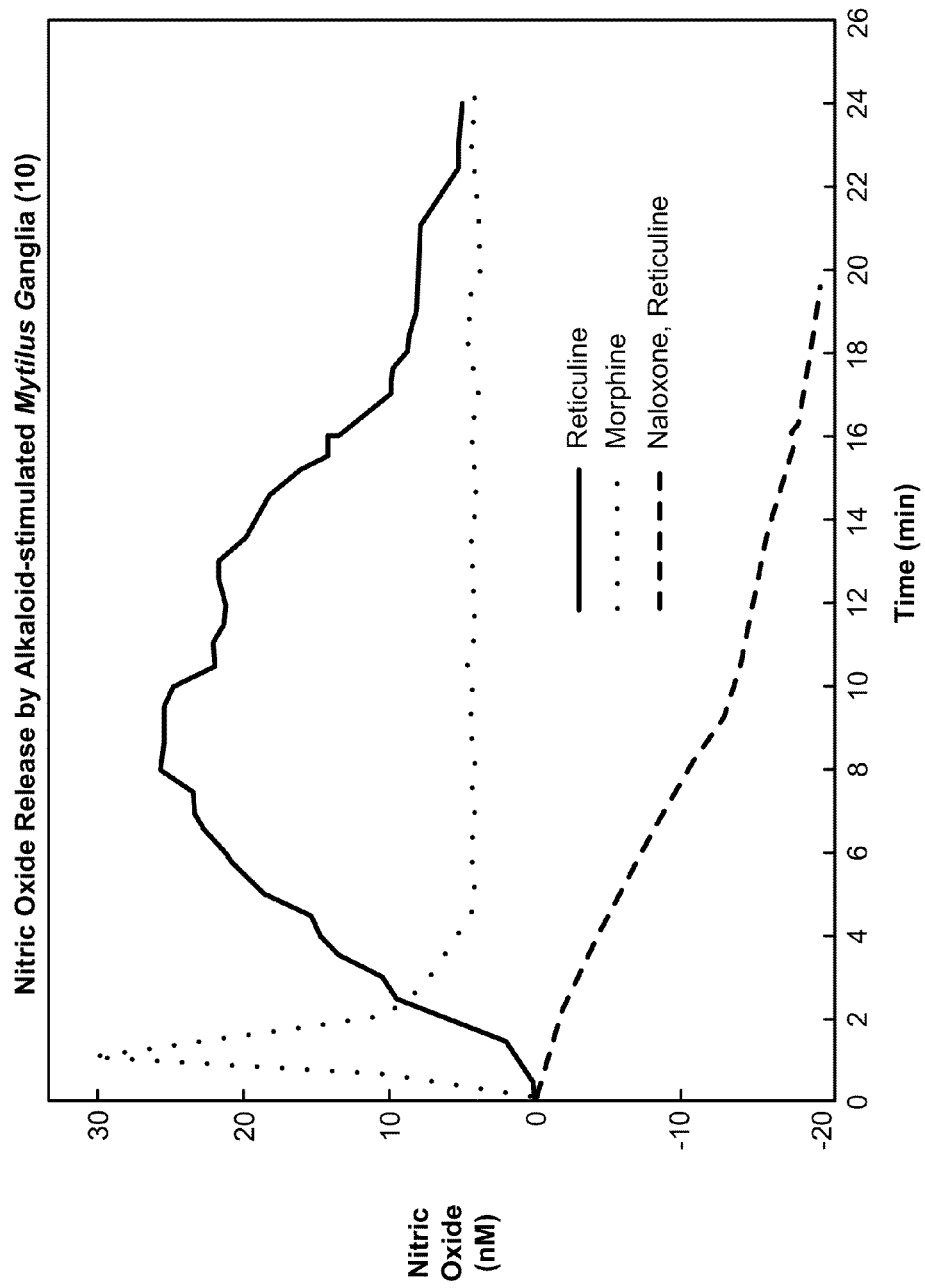

FIG. 4 is a graph plotting NO release versus time for ganglia treated with reticuline ($10^{-7}$ M) alone, morphine ($10^{-6}$ M) alone, or naloxone ($10^{-6}$ M) plus reticuline ($10^{-7}$ M).

Figure 5:
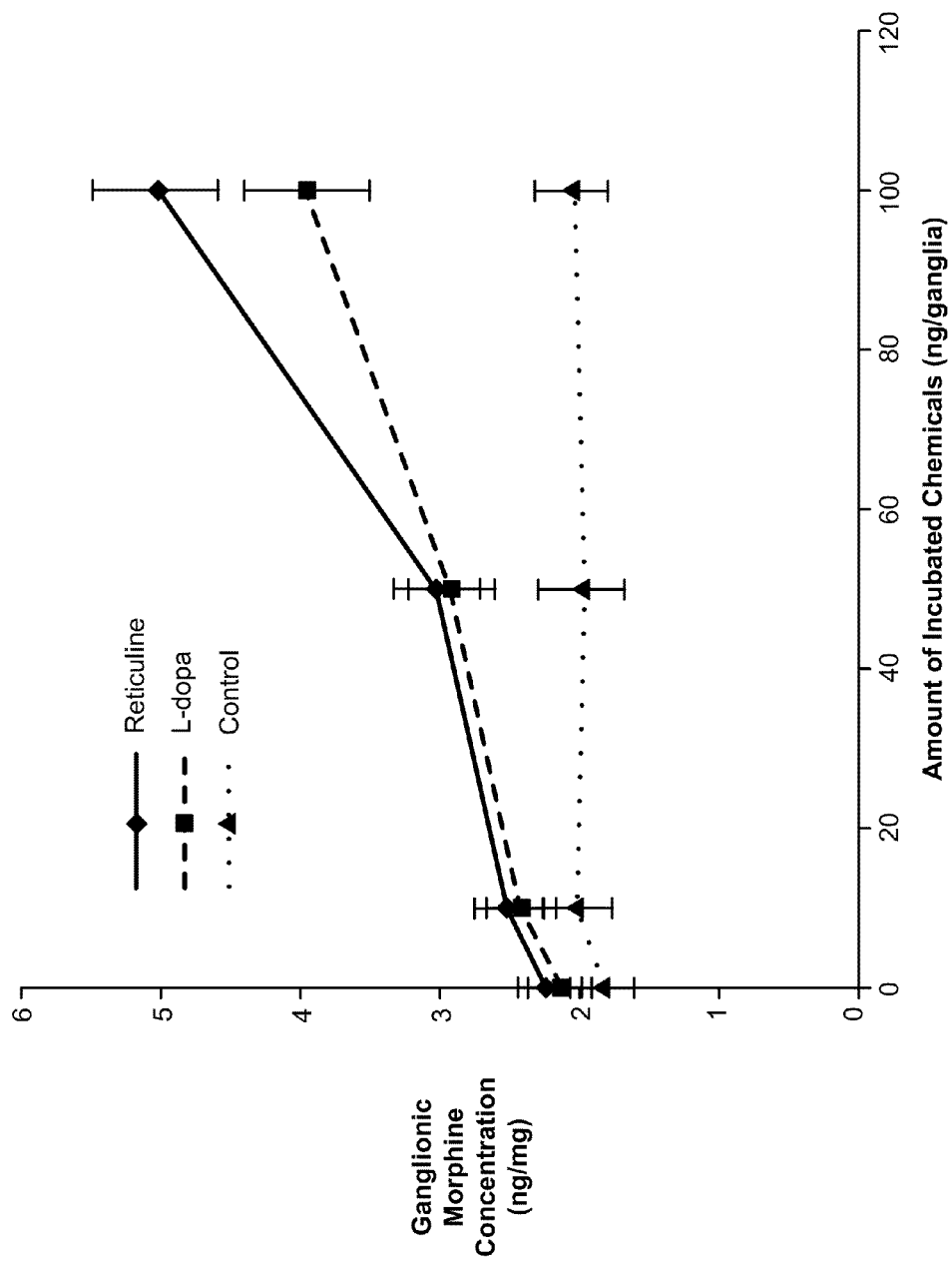

FIG. 5 is a graph plotting morphine levels detected for *Mytilus edulis* pedal ganglia treated in vitro with 1.0, 10, 50, or 100 ng of L-dopa or reticuline for 60 minutes. Vehicle treated ganglia morphine levels before and after the incubation with the respective precursors was determined (2.1±0.44 and 2.3±0.31 ng/ganglia, respectively). One Way ANOVA analysis revealed that the morphine levels in ganglion incubated with reticuline (50 and 100 ng) or L-DOPA (50 and 100 ng) were significantly higher than those measured in control ganglion (P<0.01 for 50 ng amounts, and P<0.001 for 100 ng amounts). One ganglion weighs about 1.7 mg. All determinations were replicated four times, and the mean±SEM is presented.

Figure 6:
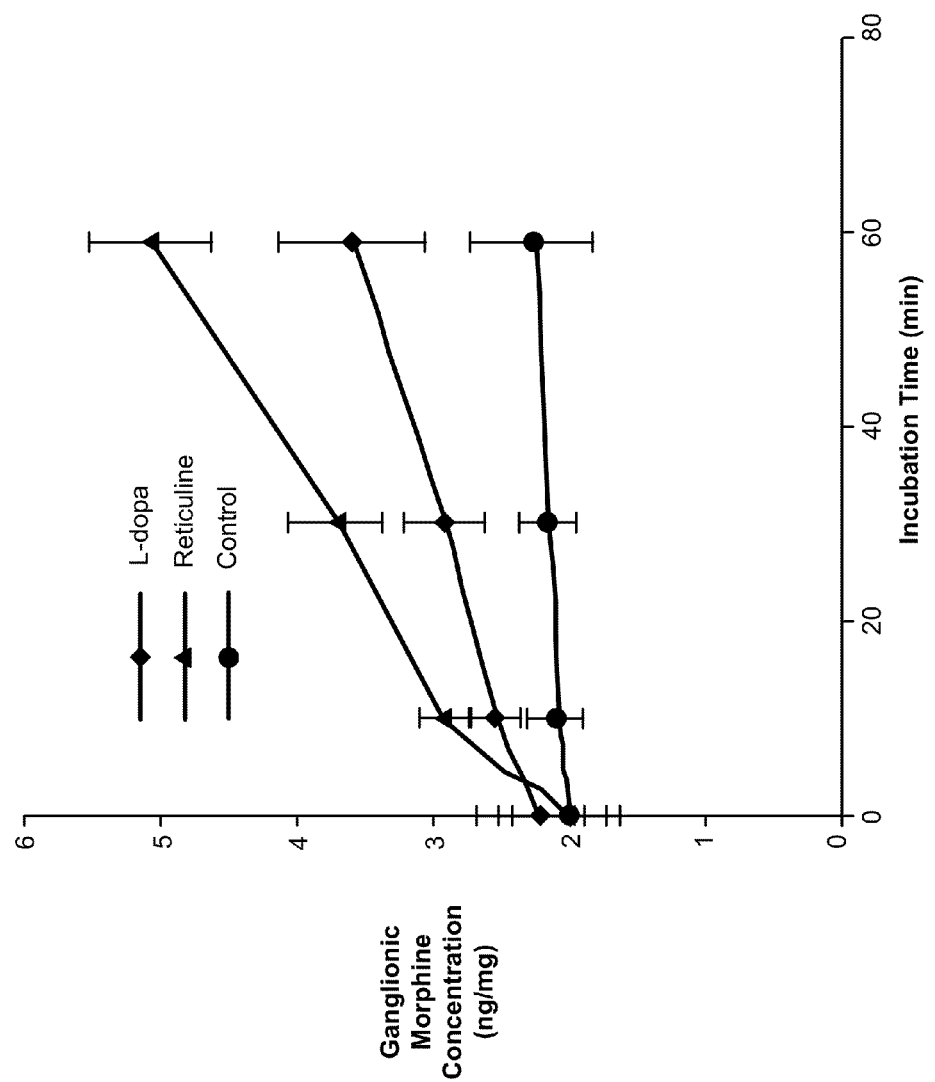

FIG. 6 is a graph plotting morphine levels versus the time *Mytilus edulis* ganglia were incubated with reticuline or L-DOPA (1 µg/10 ganglia). One Way ANOVA analysis revealed that the ganglionic morphine levels in ganglia incubated with the morphine precursors were significantly higher than control at 30 and 60 minutes (P<0.01). All determinations were replicated four times, and the mean graphed±SEM.

Figure 7:
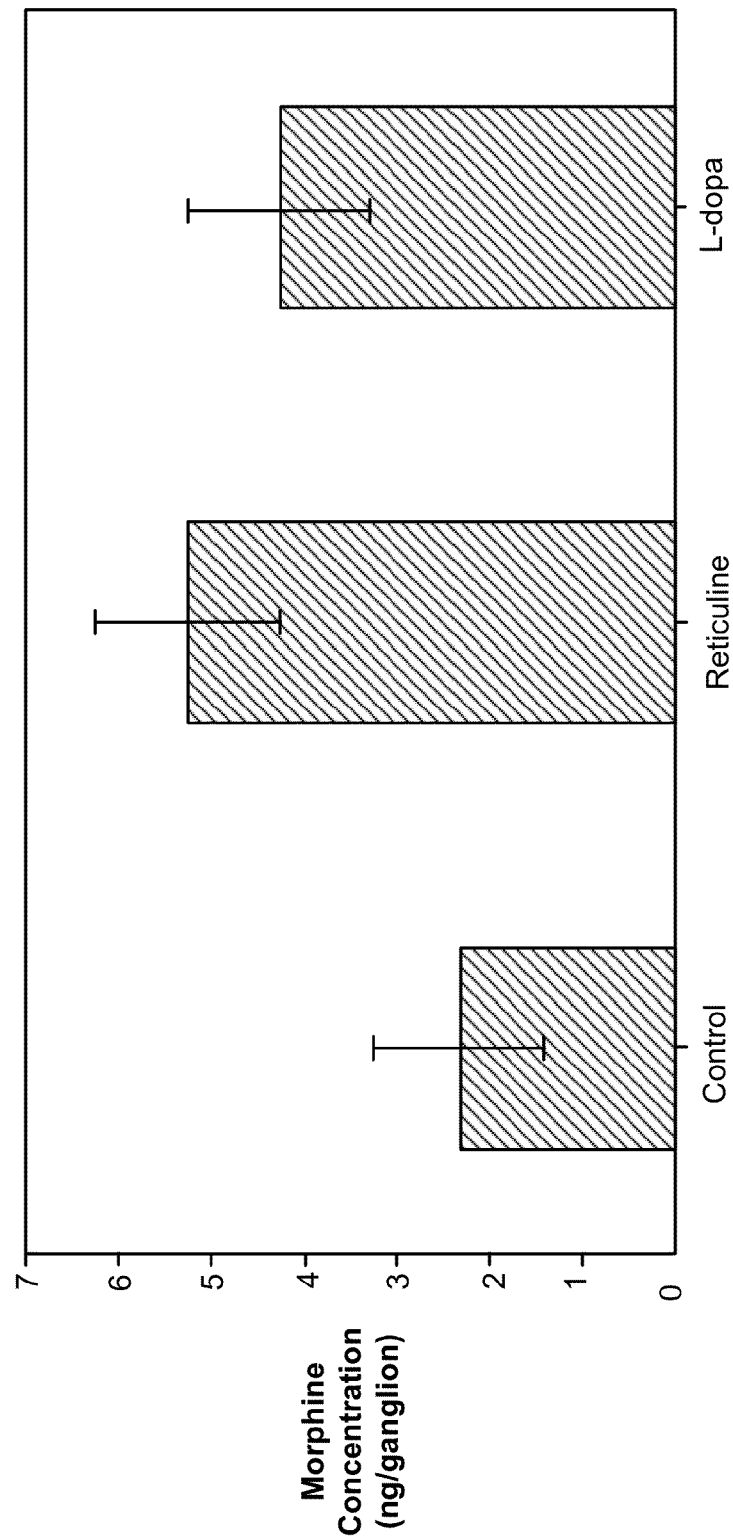

FIG. 7 is a bar graph plotting the level of morphine (ng/ganglion) in animals one hour after receiving an injection of reticuline or L-DOPA (1 µg/animal) into the base of *Mytilus* foot. Morphine levels were significantly increased compared to control levels (P<0.01; One Way ANOVA analysis). All determinations were replicated four times, and the mean±SEM is presented.

Figure 8:
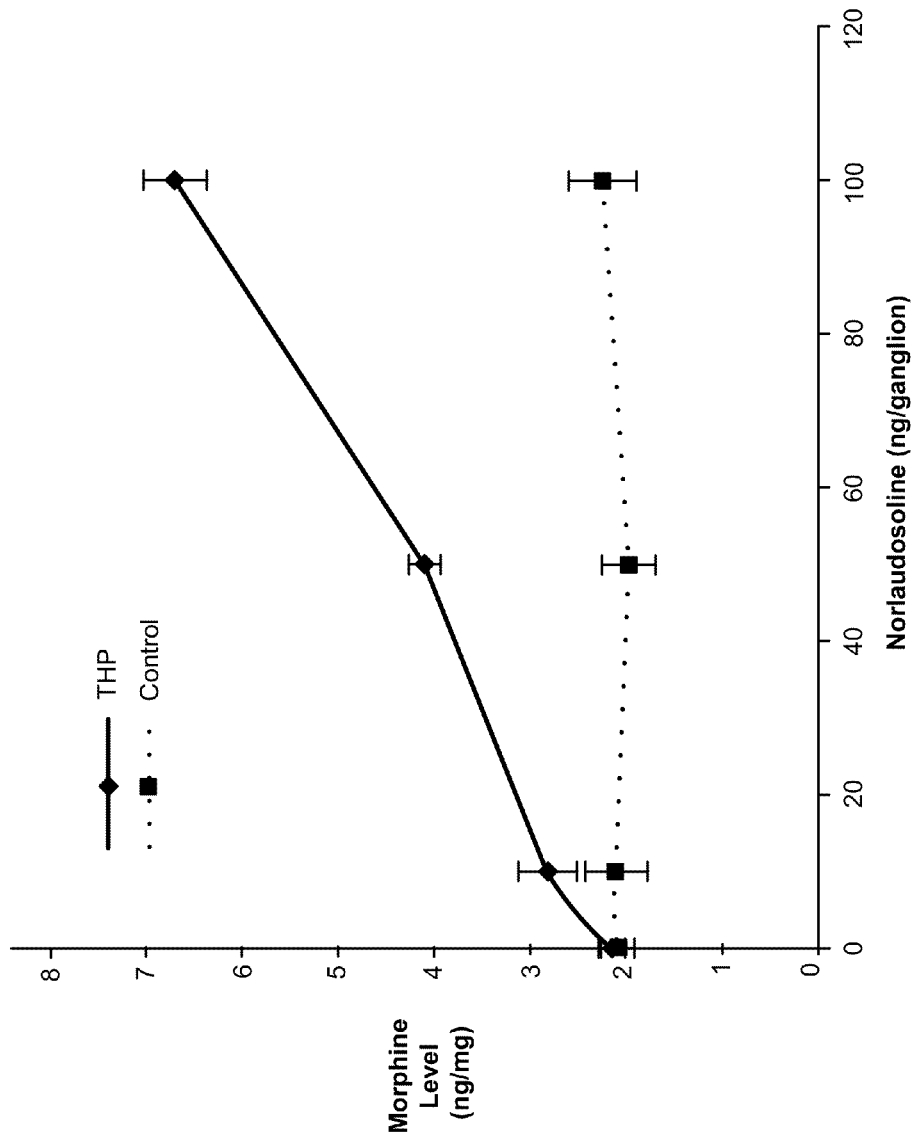

FIG. 8 is a graph plotting morphine levels detected for *Mytilus edulis* pedal ganglia treated in vitro with 1.0, 10, 50, or 100 ng of norlaudanosoline for 60 minutes. One Way ANOVA analysis revealed that the morphine levels in ganglion incubated with norlaudanosoline were significantly higher than control at 50 and 100 ng of norlaudanosoline. All determinations were replicated four times, and the mean graphed±SEM.

Figure 9:
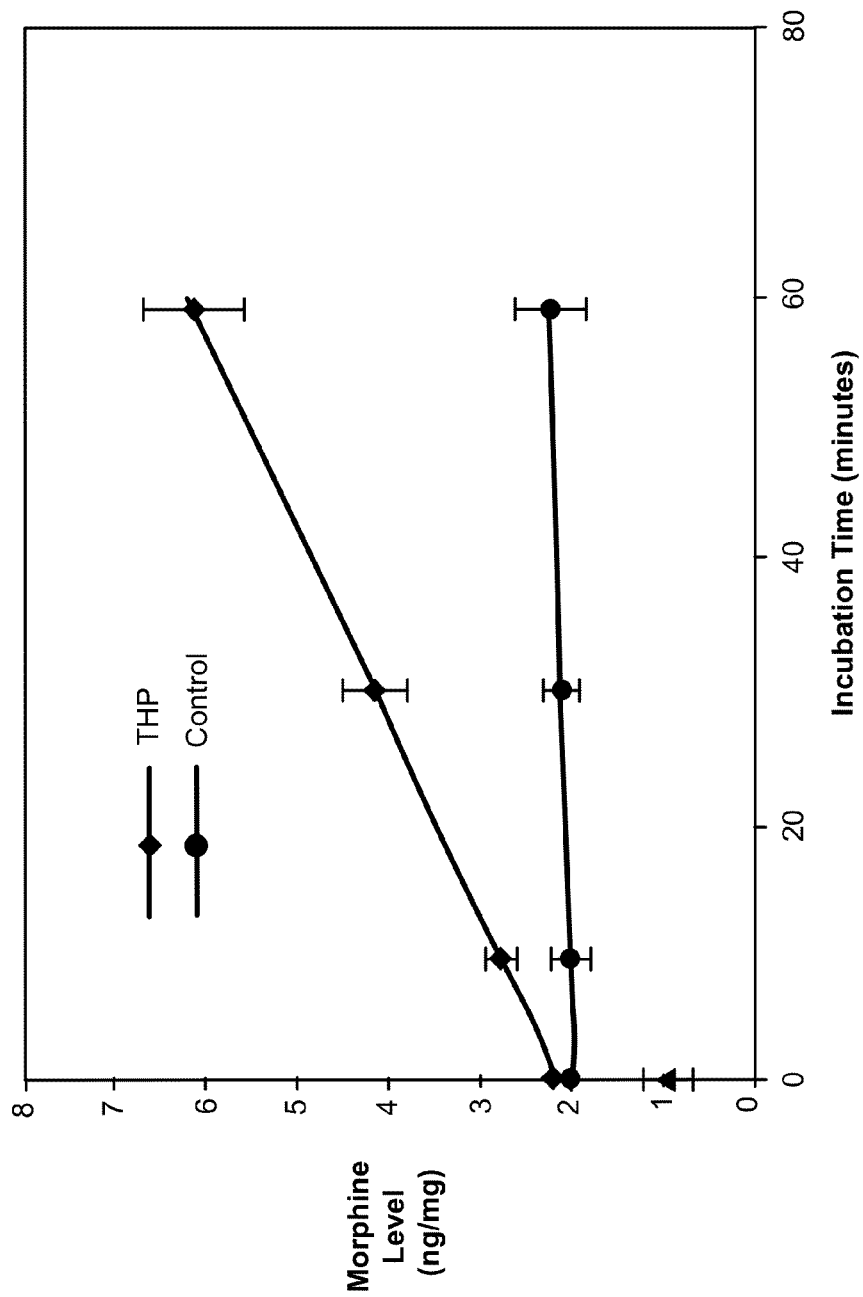

FIG. 9 is a graph plotting morphine levels versus the time *Mytilus edulis* ganglia were incubated with norlaudanosoline (100 ng/ganglia). One Way ANOVA analysis revealed that the morphine levels in ganglia incubated with norlaudanosoline were significantly higher than controls at 30 and 60 minutes (P<0.01). All determinations were replicated four times, and the mean graphed±SEM.

Figure 10:
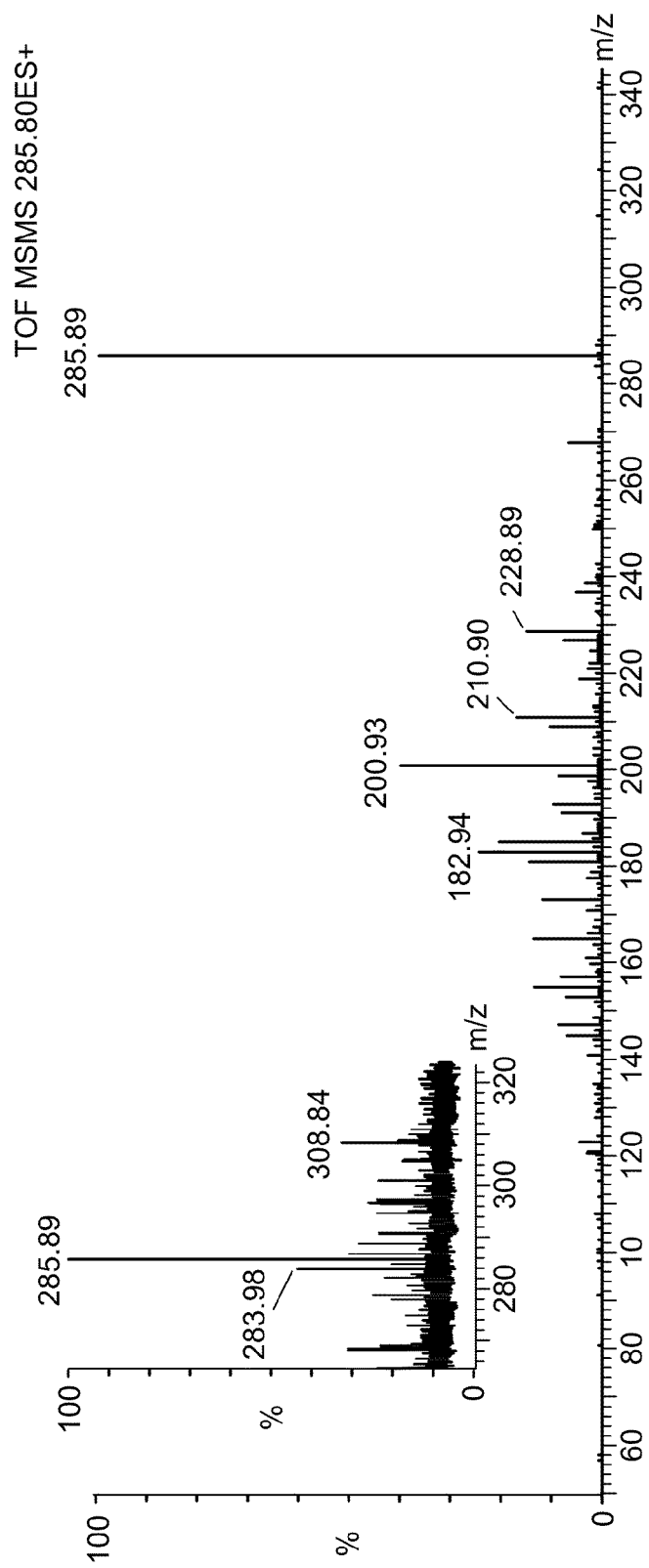

FIG. 10 is a Q-TOF analysis of authentic morphine extracted from HPLC fractions (inset). WBC morphine exhibited the same MS as authentic material.

Figure 11A:
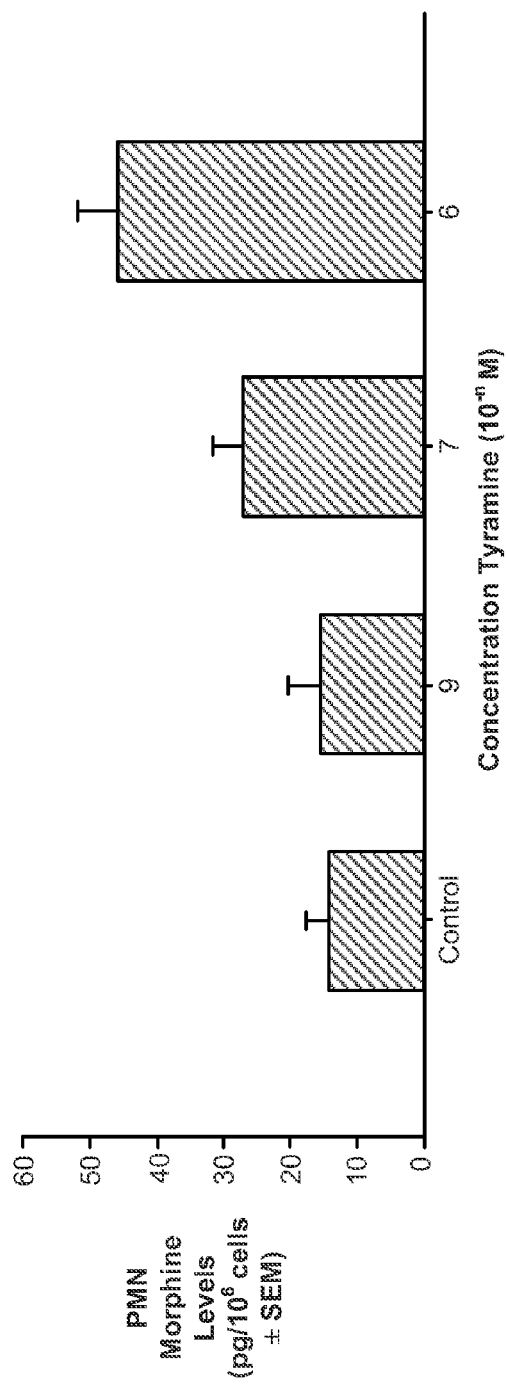
Figure 11B:
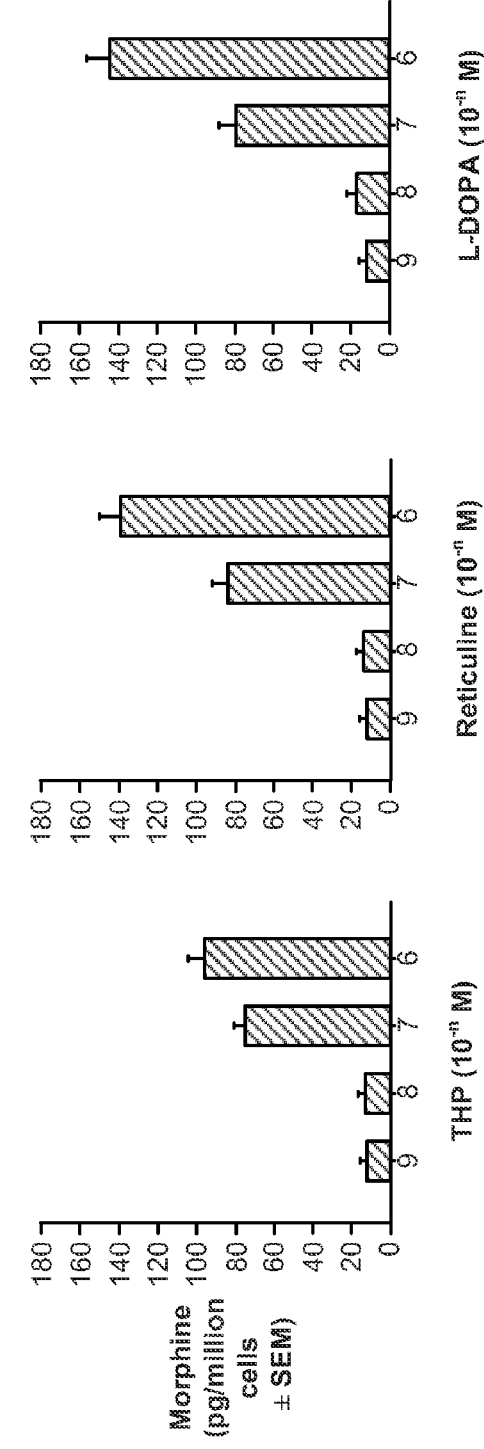

FIG. 11A is a graph plotting the amount of morphine produced from human WBC obtained from a Buffy coat and incubated with the indicated amount of tyramine for one hour (P<0.001, One Way ANOVA at the $10^{-7}$ to $10^{-6}$ M concentrations). FIG. 11B contains bar graphs plotting the amount of morphine produced from human WBC obtained from a Buffy coat and incubated with the indicated amount of norlaudanosoline (THP), reticuline, or L-DOPA for one hour (P<0.001, One Way ANOVA at the $10^{-7}$ to $10^{-6}$ M concentrations). Each experiment was repeated three times, and the mean±SEM is presented.

Figure 12:
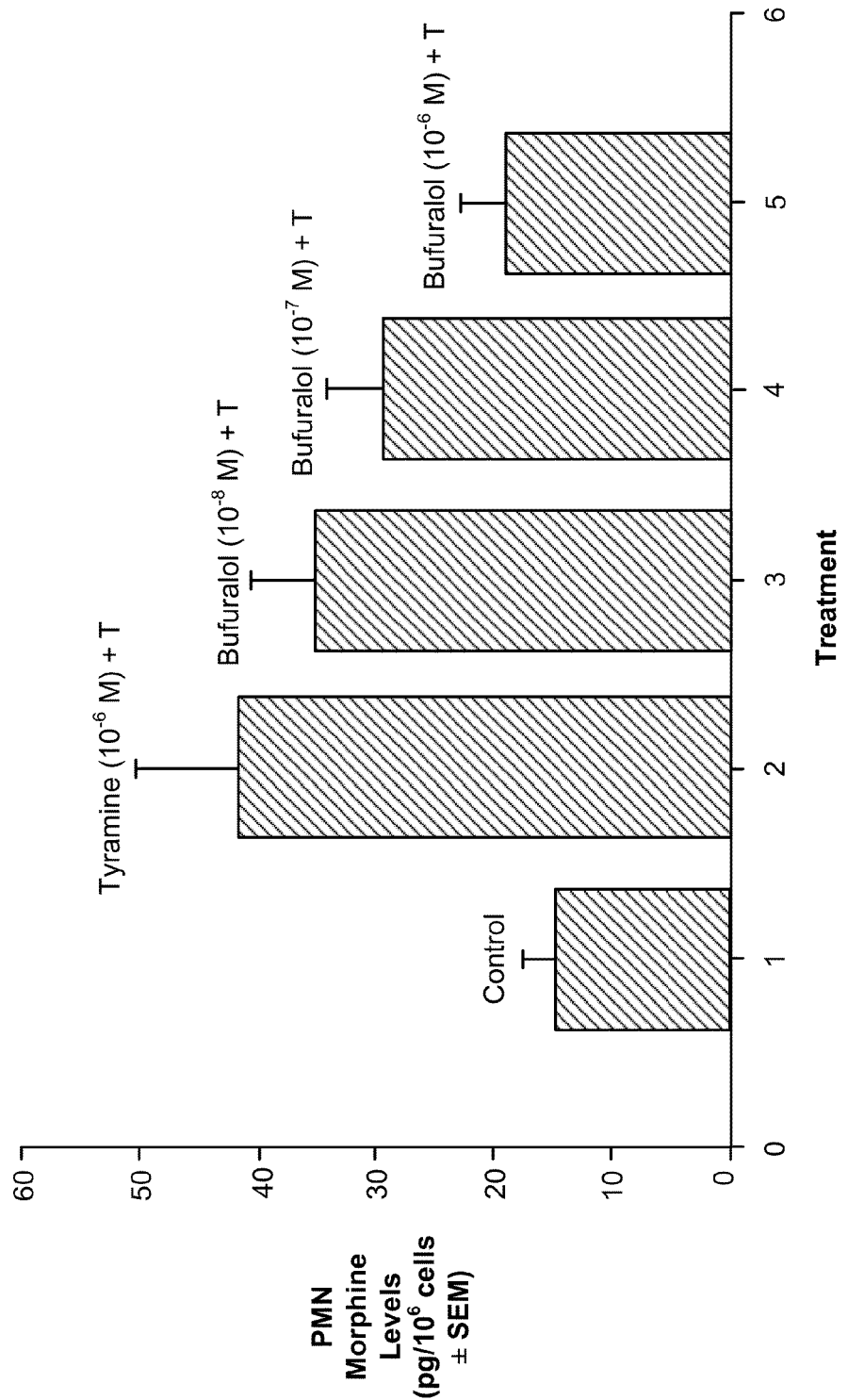

FIG. 12 is a graph plotting the amount of morphine produced from human PMNs obtained from a Buffy coat and incubated with tyramine (T; $10^{-6}$ M) and the indicated amount of bufuralol. The tyramine-induced morphine levels were diminished significantly with increasing concentrations of bufuralol (P<0.001, One Way ANOVA). Each experiment was repeated three times, and the mean±SEM is presented.

Figure 13:
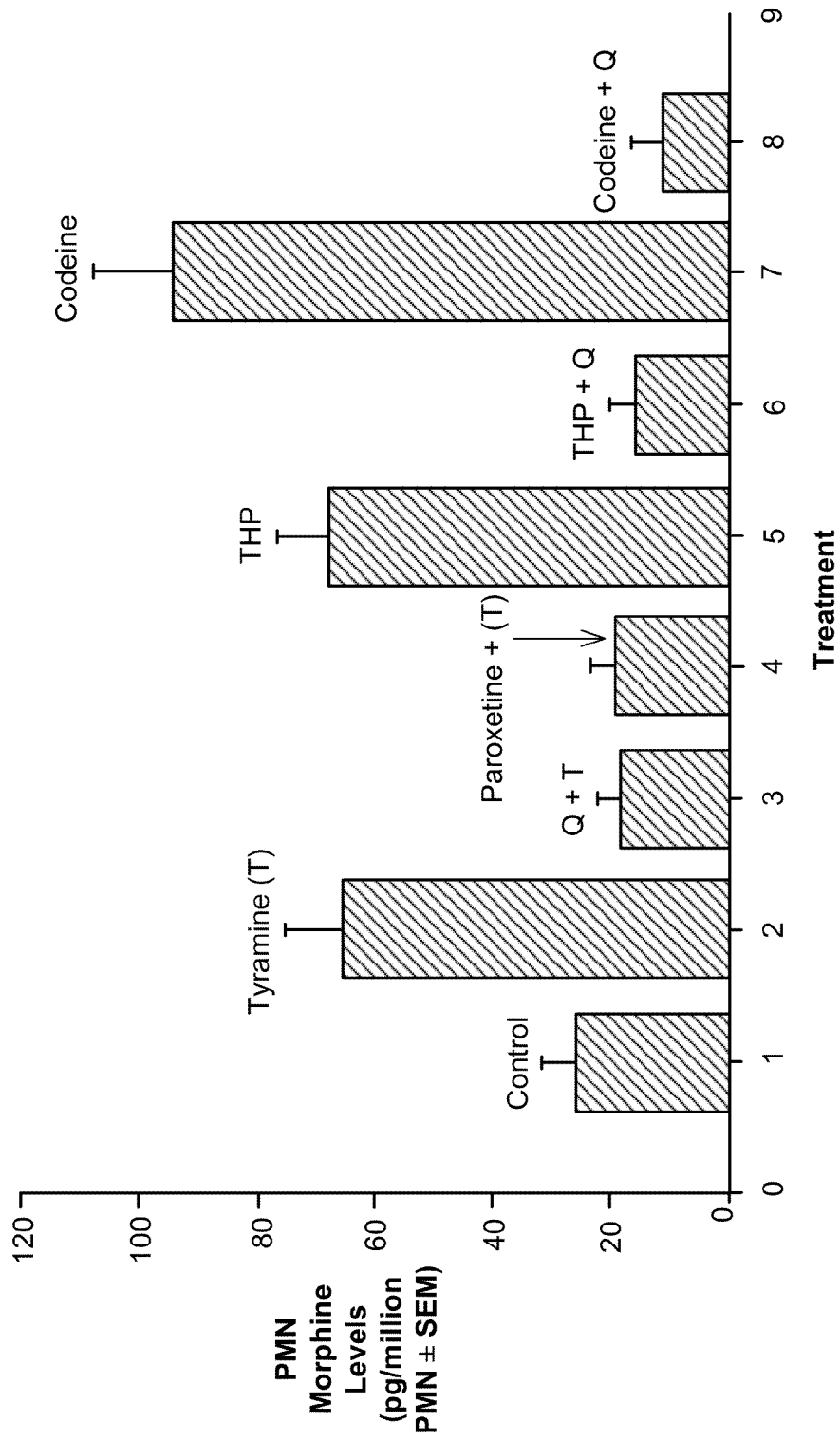

FIG. 13 is a graph plotting the amount of morphine produced from human PMNs obtained from a Buffy coat and incubated with tyramine (T; $10^{-6}$ M), norlaudanosoline (THP; $10^{-7}$M), or codeine together with either quinidine ($10^{-6}$ M) or paroxetine ($10^{-6}$ M). The tyramine- and THP-induced morphine levels were diminished by treatment with quinidine (P<0.001, One Way ANOVA compared to tyramine and THP stimulated morphine levels, respectively). Each experiment was repeated five times, and the mean±SEM is presented.

Figure 14:
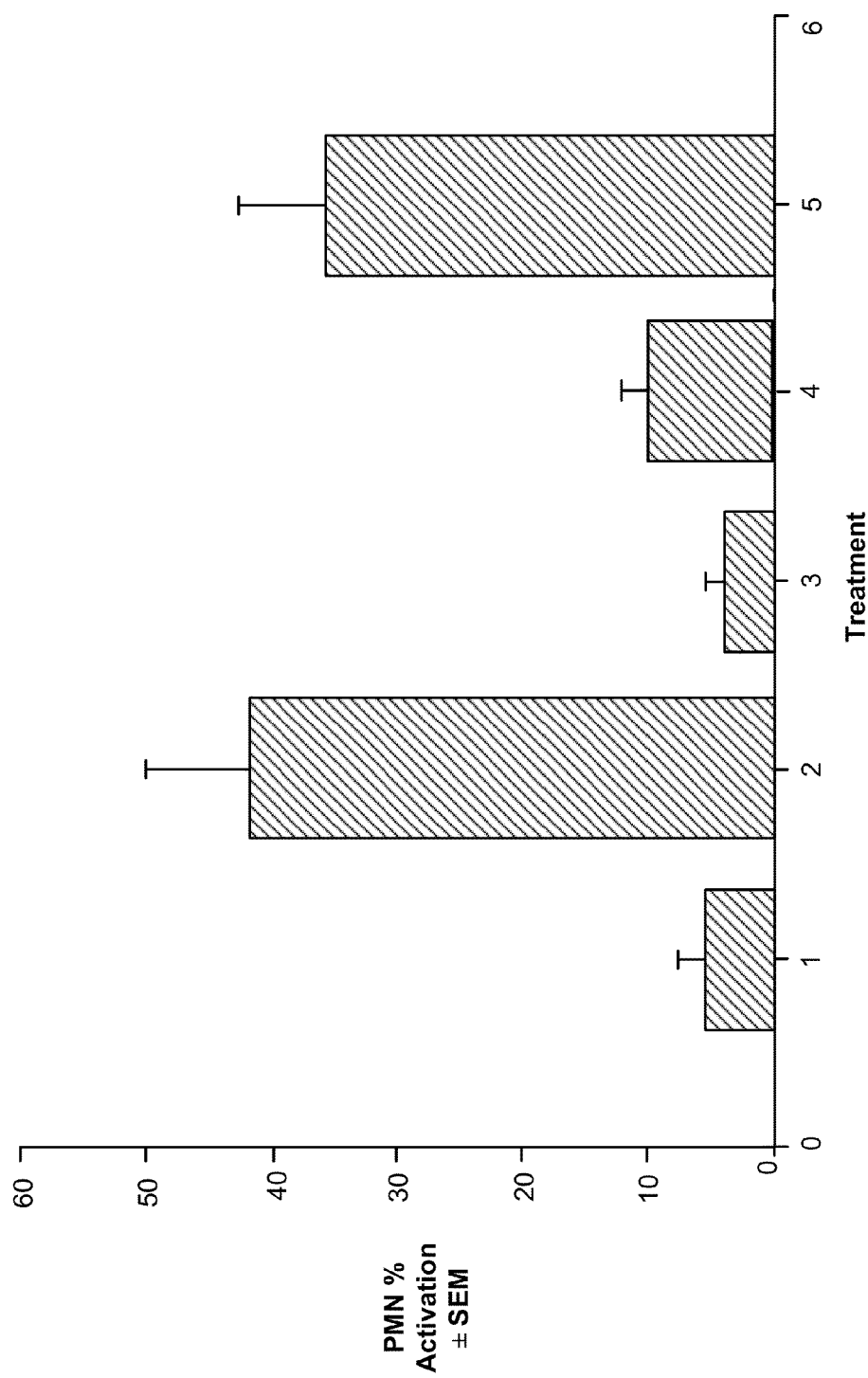

FIG. 14 is a graph plotting the level of PMN activation for cells treated as follows: 1, PMN activity level after 60 minutes of no treatment; 2, PMNs incubated with IL-1β; 3, PMNs incubated with L-DOPA ($10^{-6}$ M); 4, mixed culture with 50% L-DOPA exposed cells and 50% IL-1β exposed cells for one hour; 5, mixed culture with 50% L-DOPA exposed cells and 50% IL-1β exposed cells for one hour (the IL-1β exposed cells were exposed to naloxone ($10^{-6}$ M) five minutes before being added to the mixed culture). Cells mixed without treatment from the two groups exhibited only a 6% increase over that of their respective controls. Each experiment was replicated four times, and the mean±SEM is presented.

Figure 15:
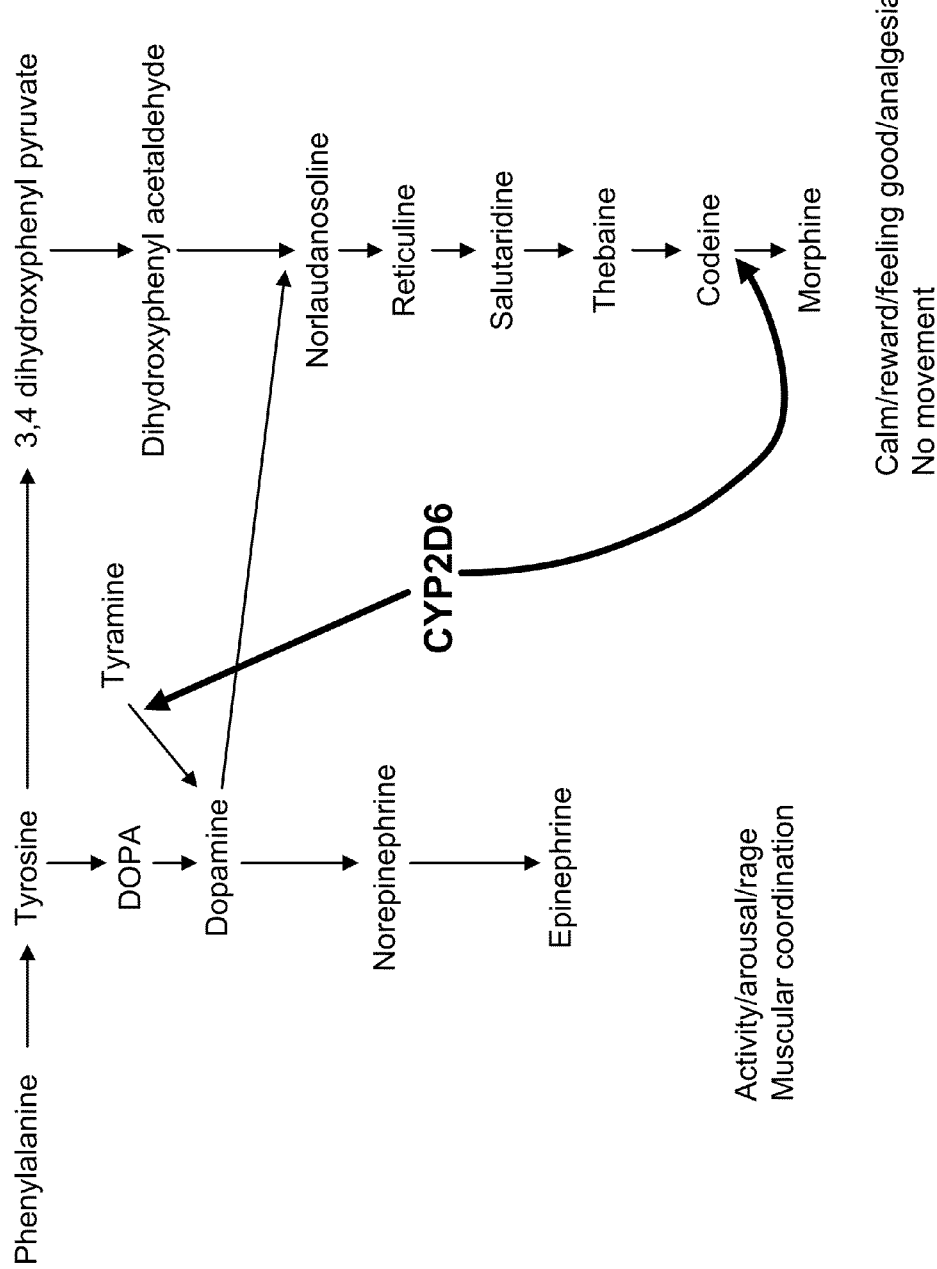

FIG. 15 is a diagram of the biosynthetic pathways for producing morphine and catecholamines.

FIG. 16A is a graph plotting morphine levels in *Mytilus edulis* ganglia treated with the indicated amount of tyrosine or tyramine for 60 minutes. At concentrations of $10^{-7}$ and $10^{-6}$ M, the mean values were statistically significant (P<0.001) as compared to untreated ganglia. FIG. 16B is a graph plotting morphine levels versus the time *Mytilus edulis* ganglia were incubated with tyrosine or tyramine ($10^{-6}$M). At 45- and 60-minute incubations, the mean values were statistically significant (P<0.001) as compared to untreated ganglia. All determinations were replicated three times, and the mean graphed±SEM.

Figure 17:
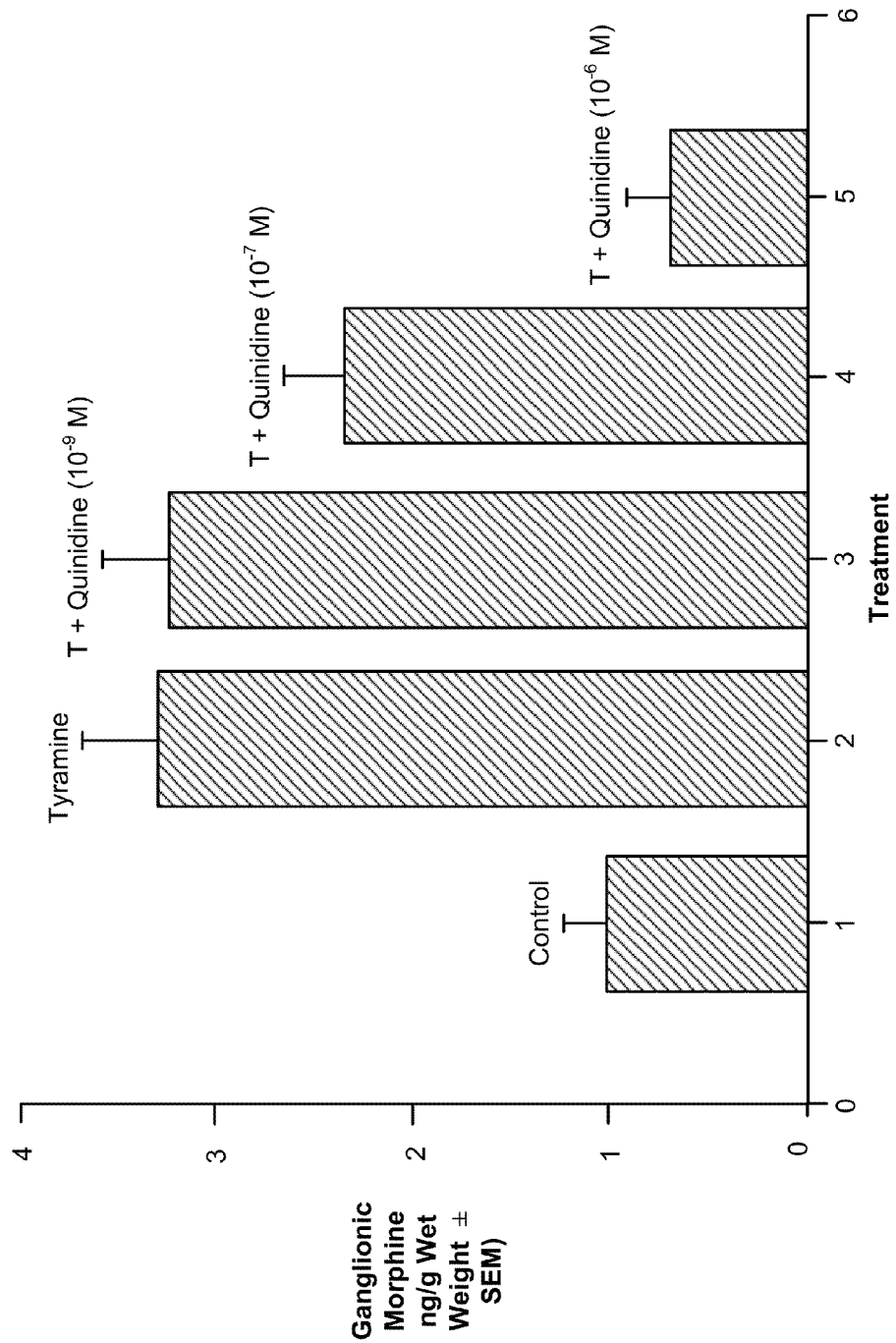

FIG. 17 is a graph plotting the amount of morphine produced from *Mytilus edulis* ganglia incubated with tyramine (T; $10^{-6}$ M) and the indicated amount of quinidine. The tyramine-induced morphine levels were diminished significantly with increasing concentrations of quinidine (P<0.001, One Way ANOVA). Each experiment was repeated five times, and the mean±SEM is presented.

Figure 18:
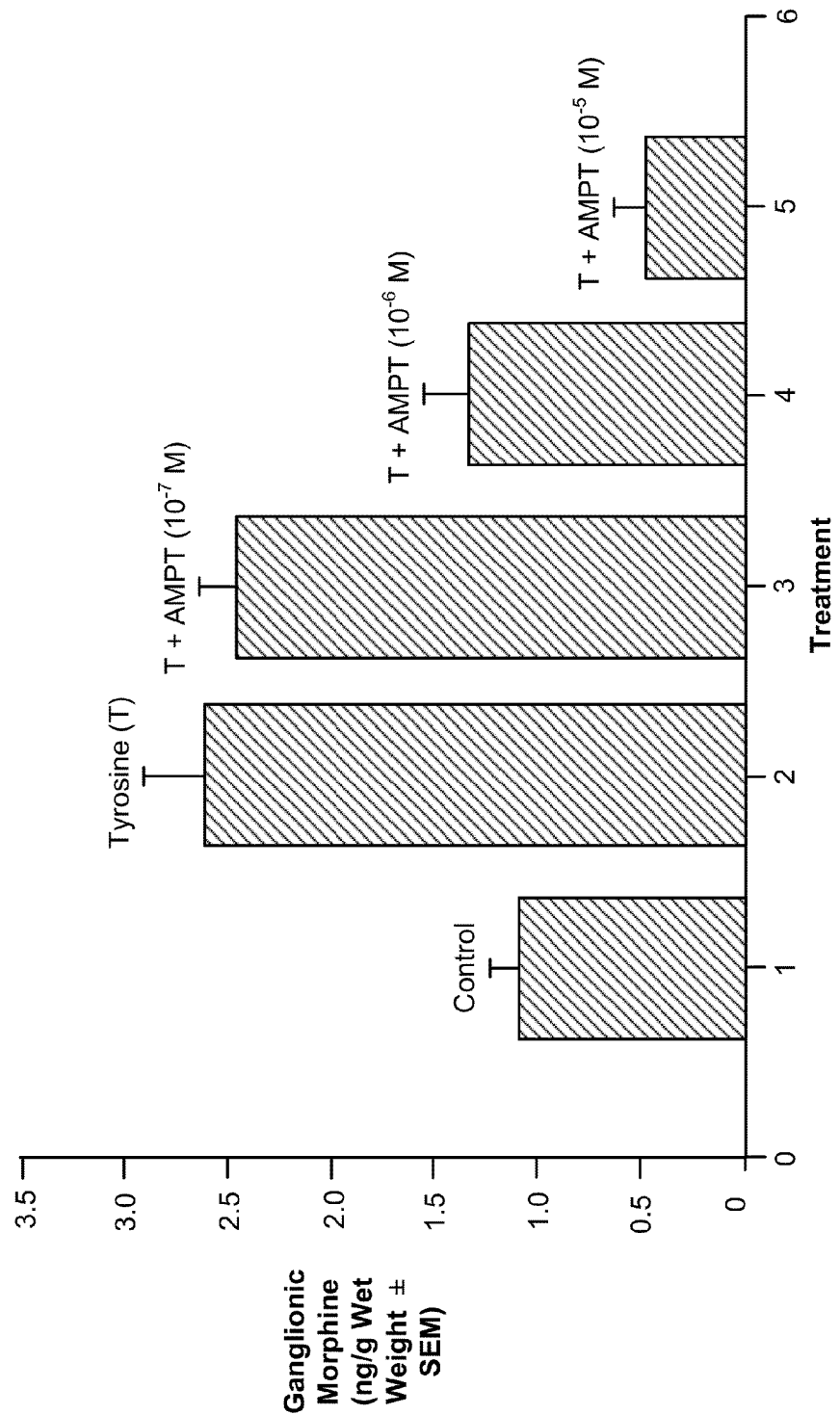

FIG. 18 is a graph plotting the amount of morphine produced from *Mytilus edulis* ganglia incubated with tyrosine (T; $10^{-6}$ M) and the indicated amount of alpha-methyl-para-tyrosine (AMPT). The tyrosine-induced morphine levels were diminished significantly with increasing concentrations of AMPT (P<0.001, One Way ANOVA). Each experiment was repeated four times, and the mean±SEM is presented.

Figure 19:
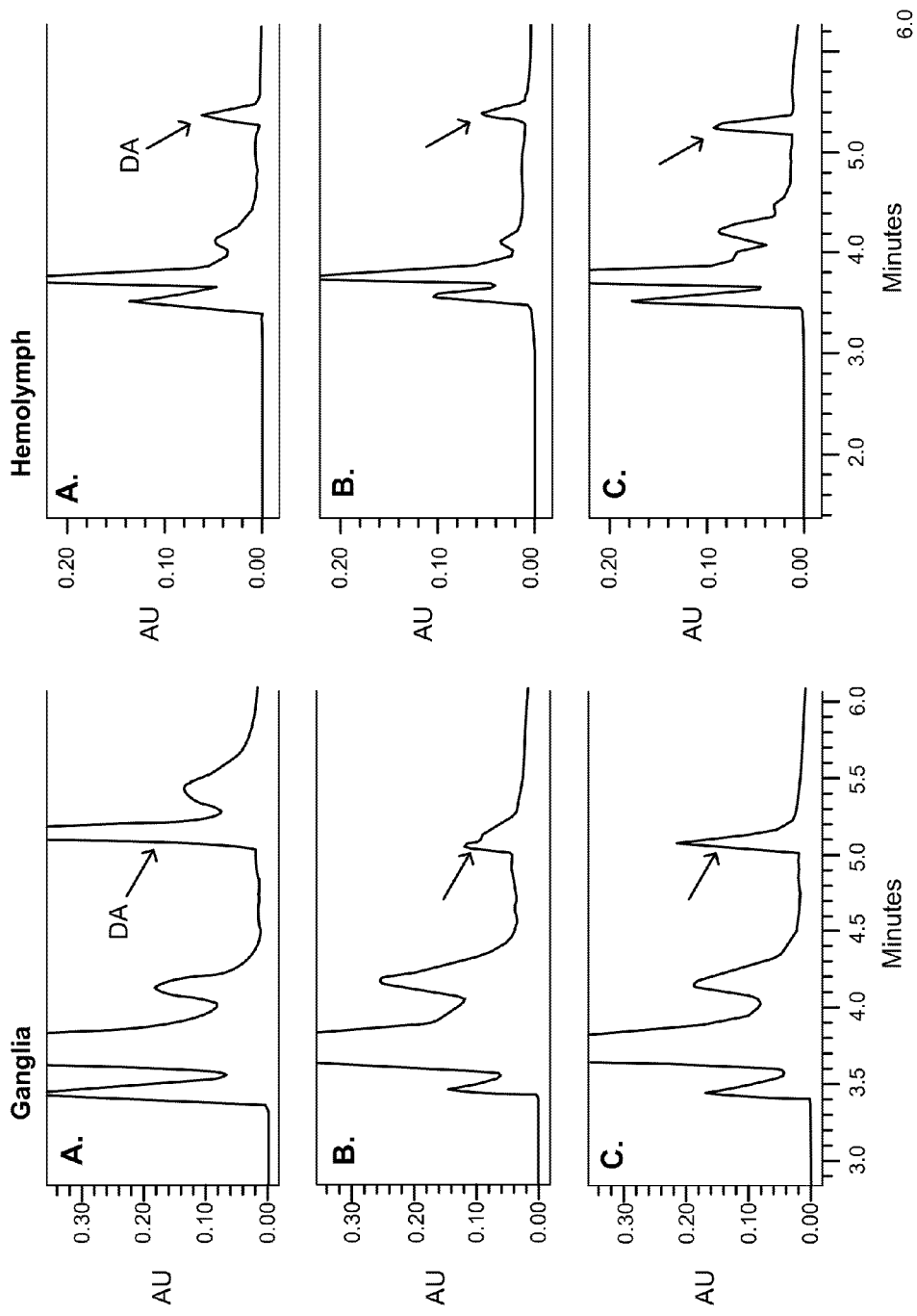

FIG. 19 contains representative HPLC chromatograms demonstrating ganglionic and hemolymph dopamine (DA) levels can be modulated by tyramine and quinidine ($10^{-6}$ M) exposure. Ganglia, Panel A: Tyramine injection (100 µg/animal, under foot) resulted in 9.17±1.21 µg of DA/g. Ganglia, Panel B: Tyramine and quinidine injections (100 µg/animal) resulted in 2.57±0.32 µg of DA/g. Ganglia, Panel C: PBS injection resulted in 4.78±0.27 µg of DA/g. Hemolymph, Panel A: PBS incubation resulted in 10.13±0.34 µg of DA/mL. Hemolymph, Panel B: Tyramine (100 µg/mL) and quinidine (10 µg/mL) exposure to pedal ganglia resulted in 10.24 µg of DA/mL. Hemolymph, Panel C: Tyramine (100 µg/mL) incubation resulted in 16.47±2.28 µg of DA/mL.

FIG. 20A is a graph plotting the level of DA detected in ganglia or hemolymph from untreated animals or animals treated with tyramine ($10^{-6}$ M) or tyramine ($10^{-6}$ M) plus quinidine ($10^{-6}$ M). Quinidine blocked the increase in endogenous ganglionic and hemolymph DA levels caused by the exposure of the pedal ganglia to tyramine alone (P<0.001). FIG. 20B is a graph plotting the level of morphine detected in ganglia from untreated animals or animals treated with codiene ($10^{-6}$ M) or codiene plus quinidine ($10^{-6}$ M). Quinidine blocked the increase in endogenous ganglionic morphine levels stimulated by codeine exposure (T-test, P<0.001). FIG. 20C is a graph plotting the level of morphine detected in ganglia from untreated animals or animals treated with norlaudanosoline (THP; $10^{-6}$ M), reticuline ($10^{-6}$ M), or DA ($10^{-6}$ M) alone or in combination with quinidine ($10^{-6}$ M). Quinidine blocked the increase in endogenous ganglionic morphine levels stimulated by norlaudanosoline, reticuline, or DA exposure (T-test, P<0.001).

FIG. 21 is a sequence alignment of a partial sequence of nucleic acid amplified from *Mytilus* tissue (bottom strand; SEQ ID NO:1) aligned with nucleotide position 843 to position 1107 of the sequence set forth in GenBank accession number M20403 (top strand; SEQ ID NO:2). The bold letters represent mismatches, n's, and gaps.

Figure 22:
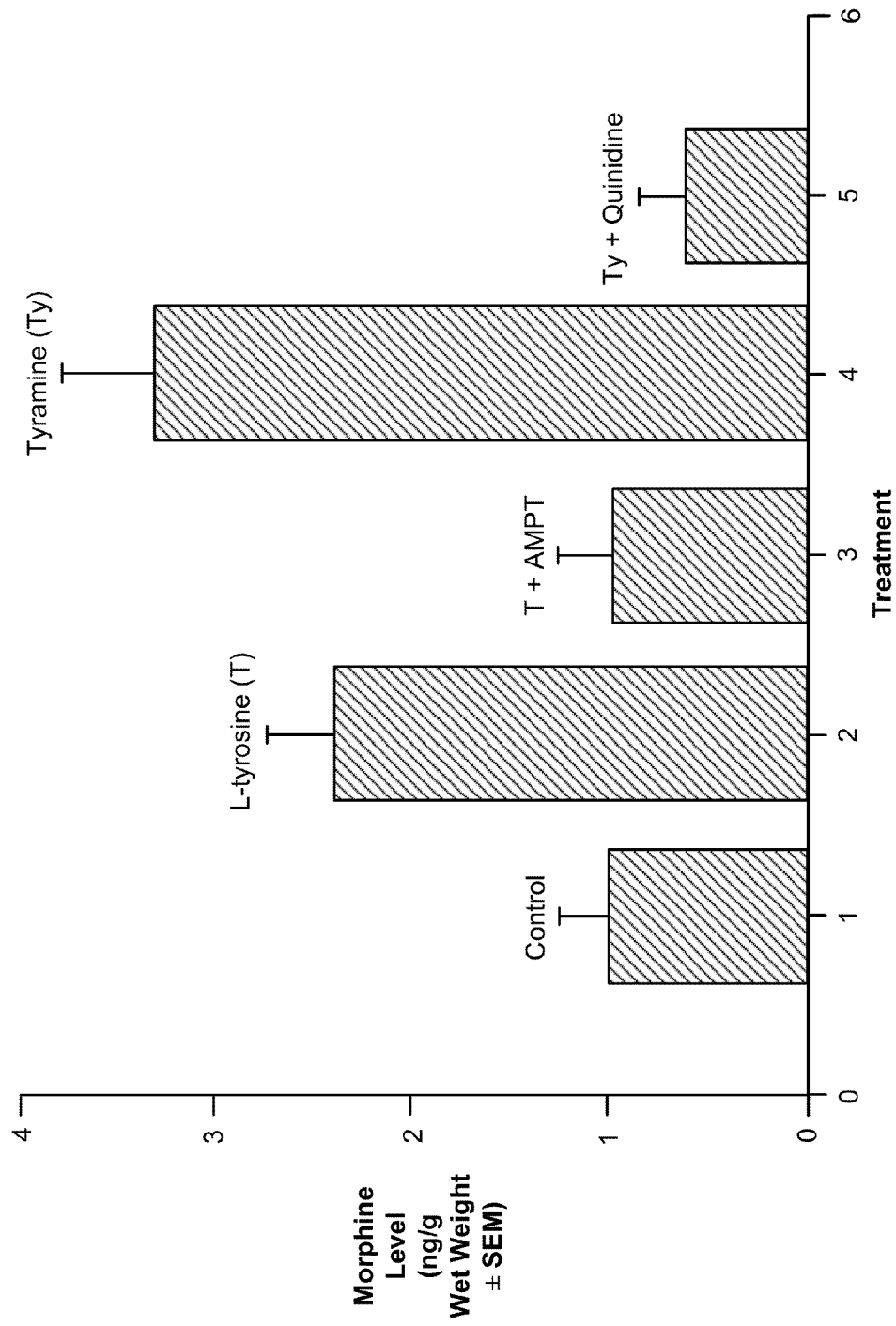

FIG. 22 is a graph plotting the amount of morphine in *Mytilus edulis* pedal ganglia following injection of tyrosine (T; $10^{-5}$ M) or tyramine (Ty; $10^{-5}$ M) into the foot of healthy, untreated animals or healthy animals having had their pedal ganglia exposed to AMPT ($10^{-4}$ M) or quinidine ($10^{-4}$ M) 15 minutes post injection.

Figure 23:
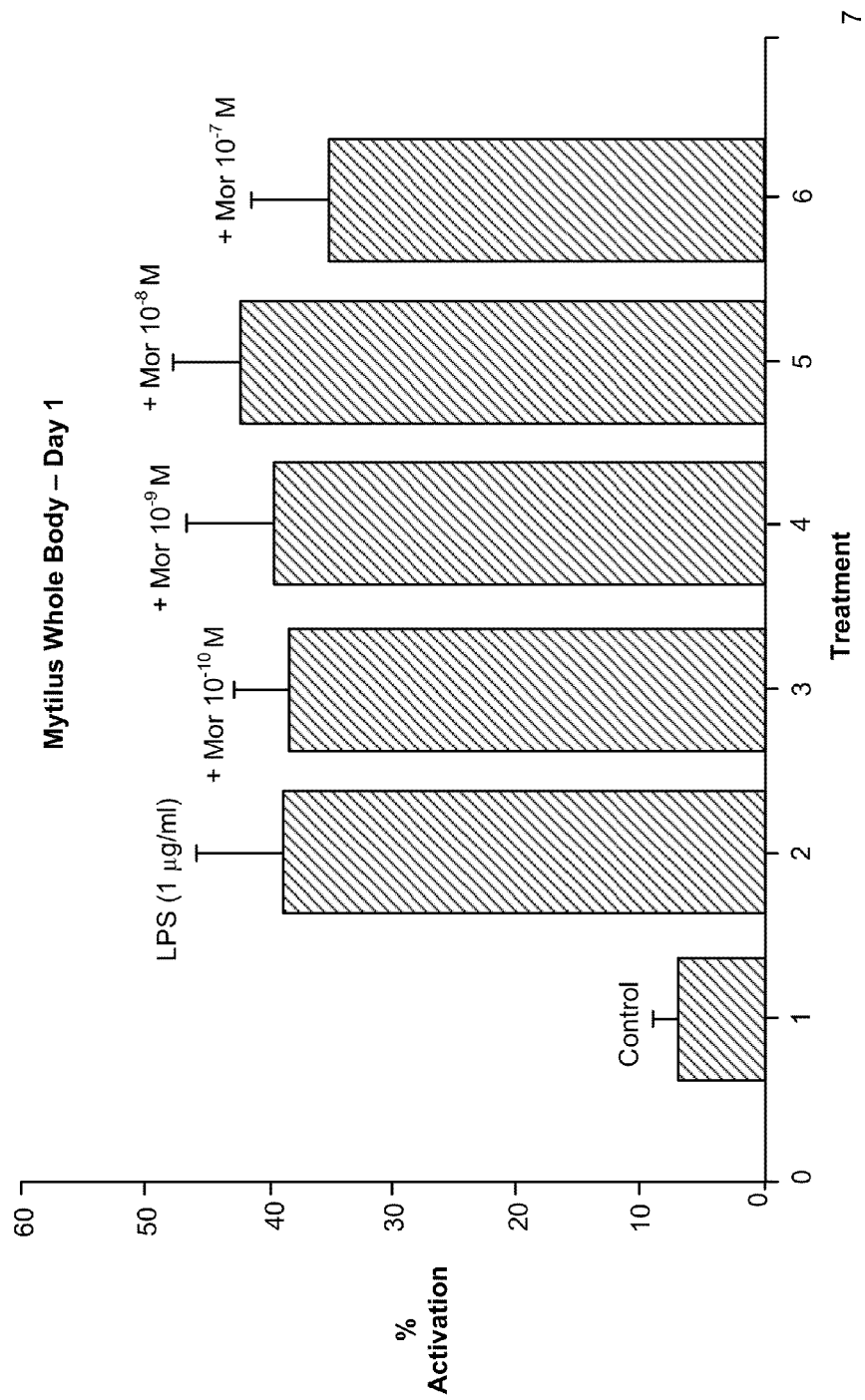

FIG. 23 is a graph plotting the percent of LPS-activated cells from animals pre-treated once with or without the indicated amount of morphine.

Figure 24:
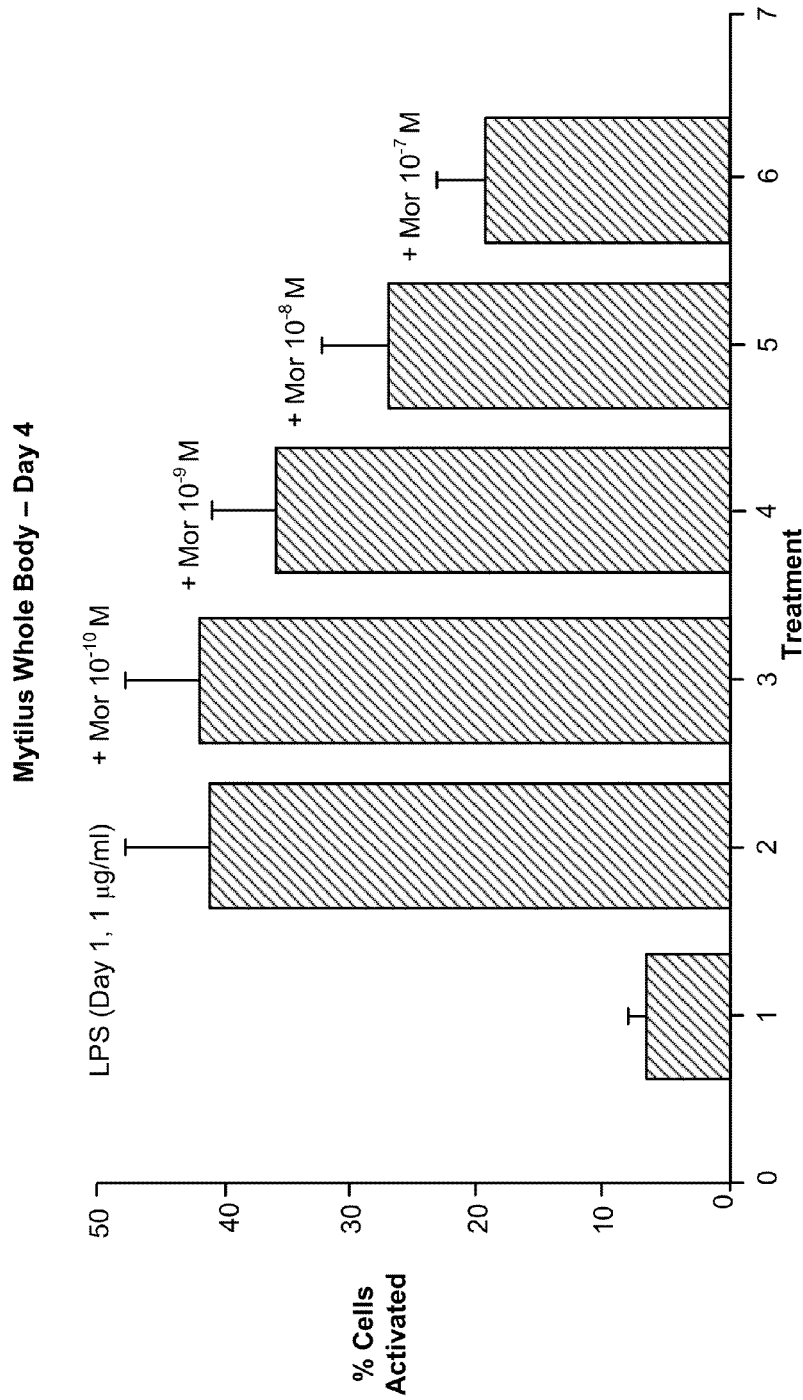

FIG. 24 is a graph plotting the percent of LPS-activated cells from animals pre-treated daily for 4 days with or without the indicated amount of morphine.

Figure 25:
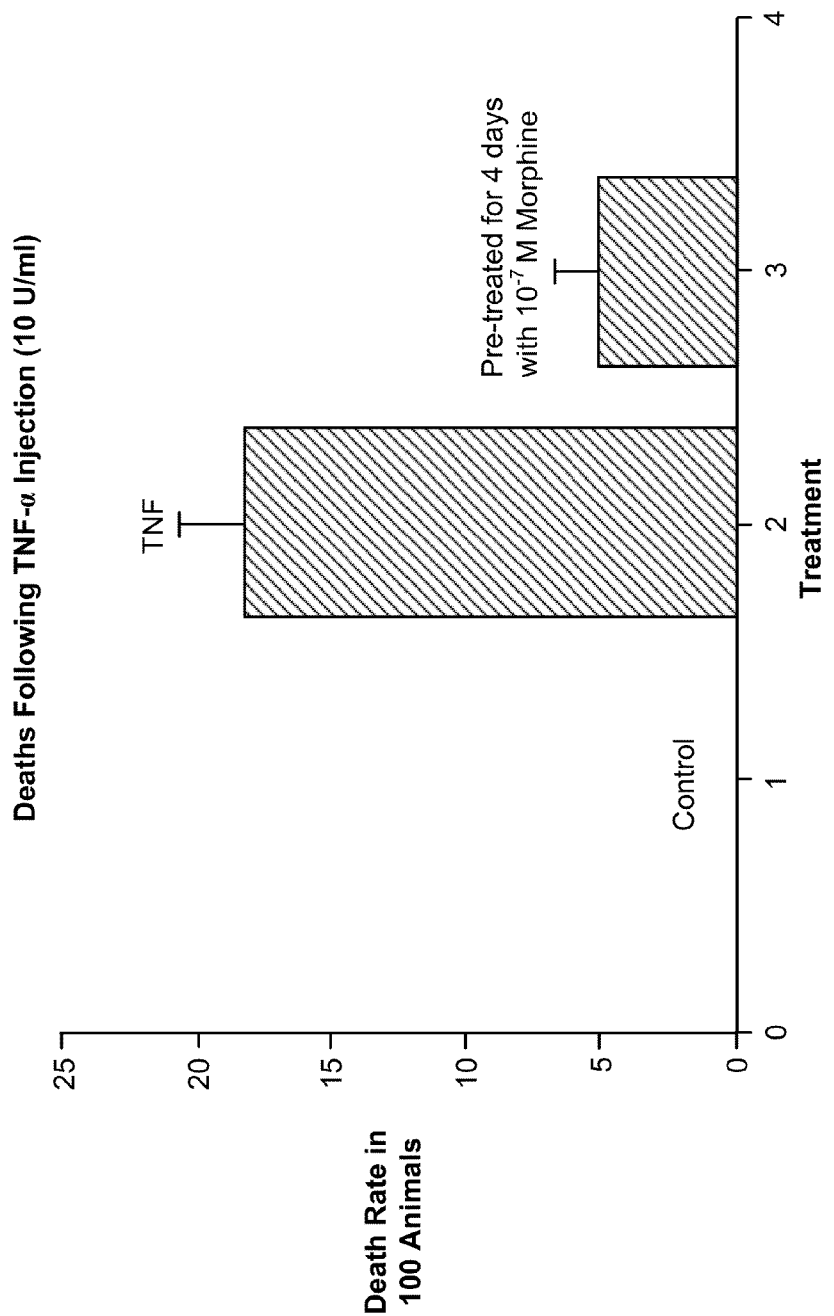

FIG. 25 is a graph plotting the death rate of TNF-α-treated animals pre-treated daily for 4 days with or without morphine ($10^{-7}$ M).

Figure 26:
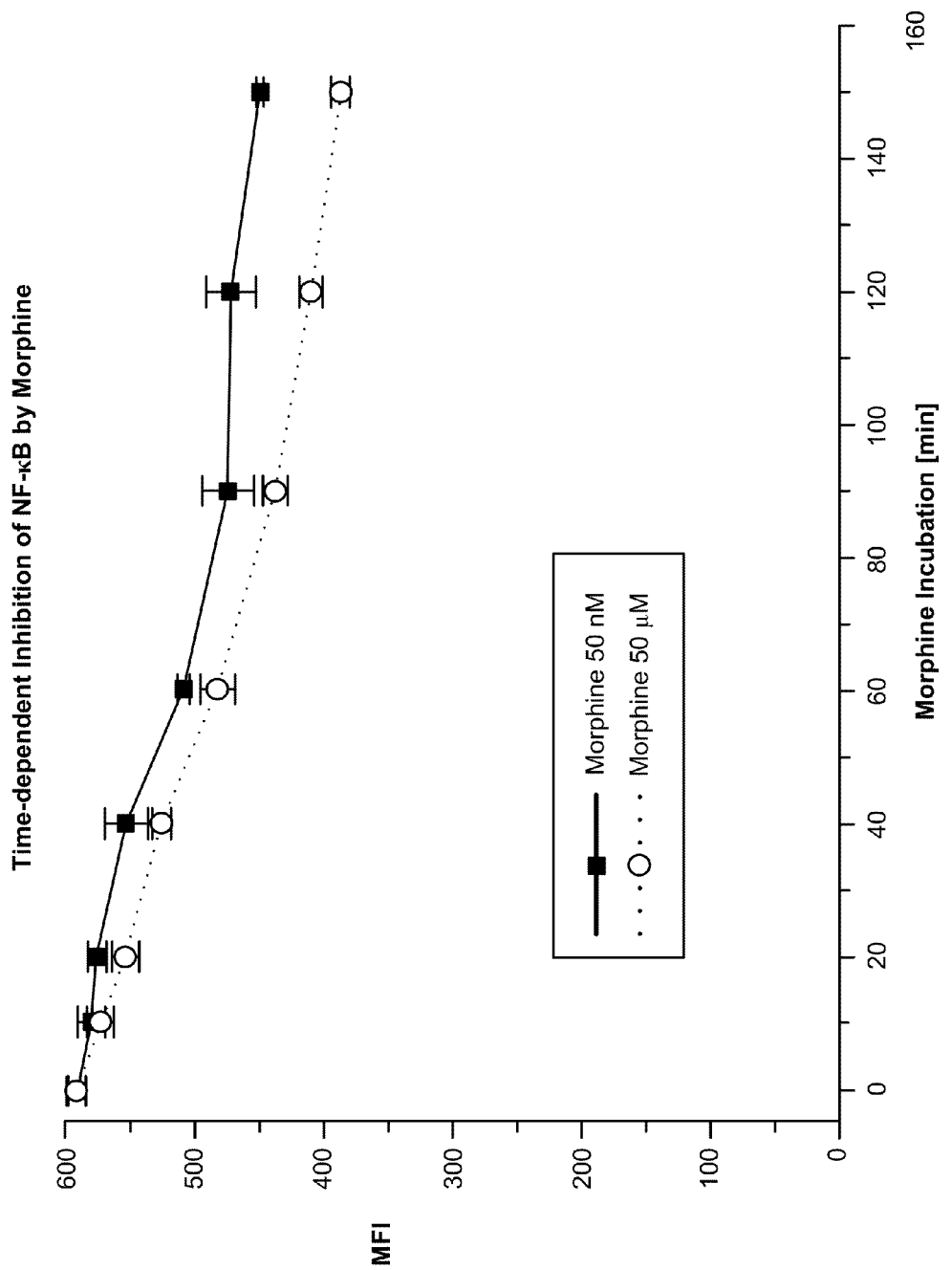

FIG. 26 is a graph plotting the median of channel fluorescence of blood samples pre-incubated with 50 nM (solid line) or 50 μM (dashed line) of morphine for the indicated times prior to LPS stimulation. Statistical analysis revealed a significant effect of morphine on NF-κB nuclear binding at any time interval when compared with LPS stimulation alone (O-min morphine).

Figure 27:
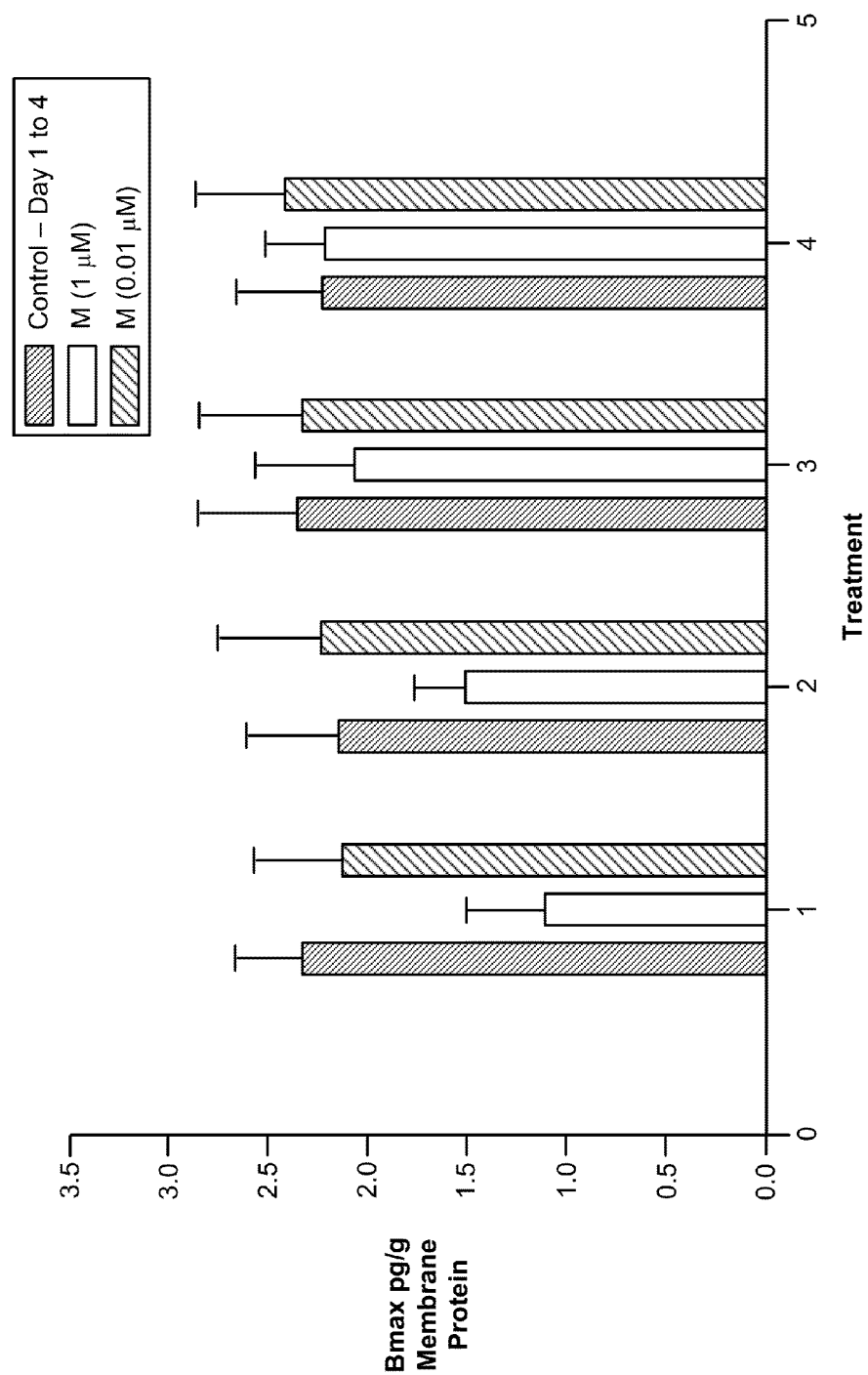

FIG. 27 is a graph plotting mu3 opiate receptor activity per gram of membrane protein (Bmax pg/g of membrane tissue) on the indicated day for animals treated with saline (control), 1 μM morphine, or 0.01 μM morphine.

Figure 28:
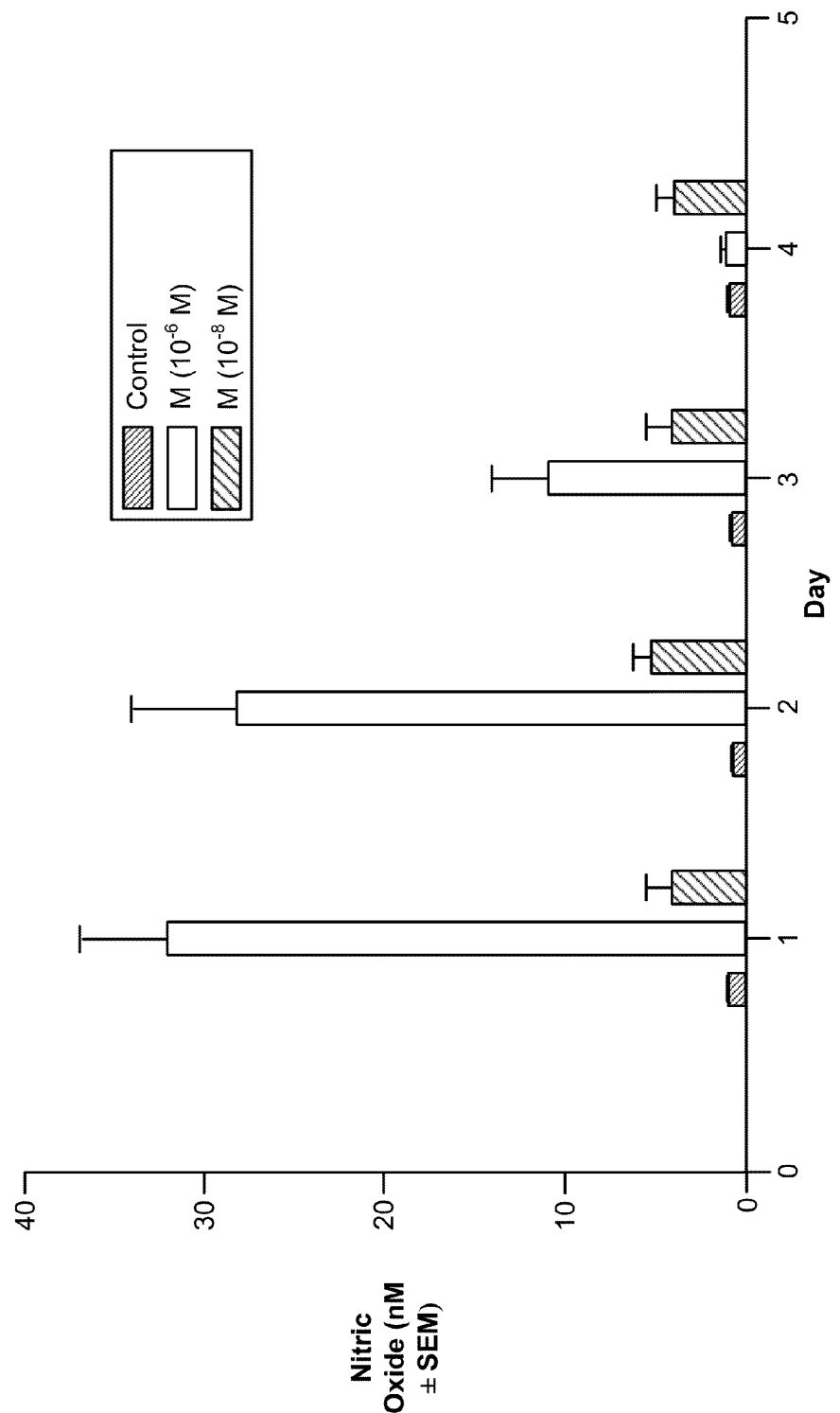

FIG. 28 is a graph plotting nitric oxide release from pedal ganglia on the indicated day for animals treated with saline (control), $10^{-6}$ M morphine, or $10^{-8}$ M morphine.

Figure 29:
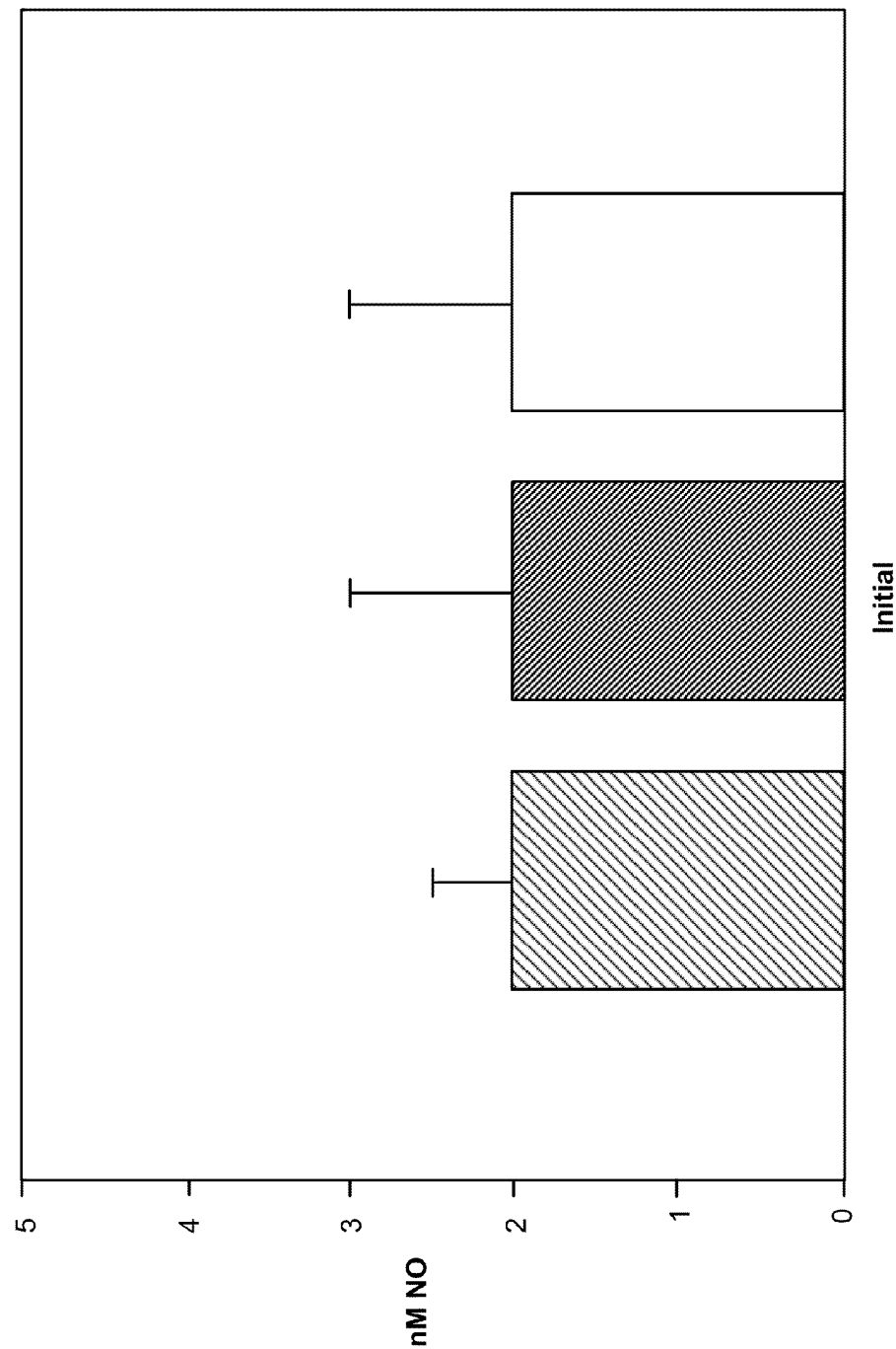

FIG. 29 is a graph plotting nitric oxide release from SH-SY5Y cells treated with $10^{-6}$ M morphine (grey bar), $10^{-6}$ M morphine (black bar), or $10^{-8}$ M morphine (white bar).

Figure 30:
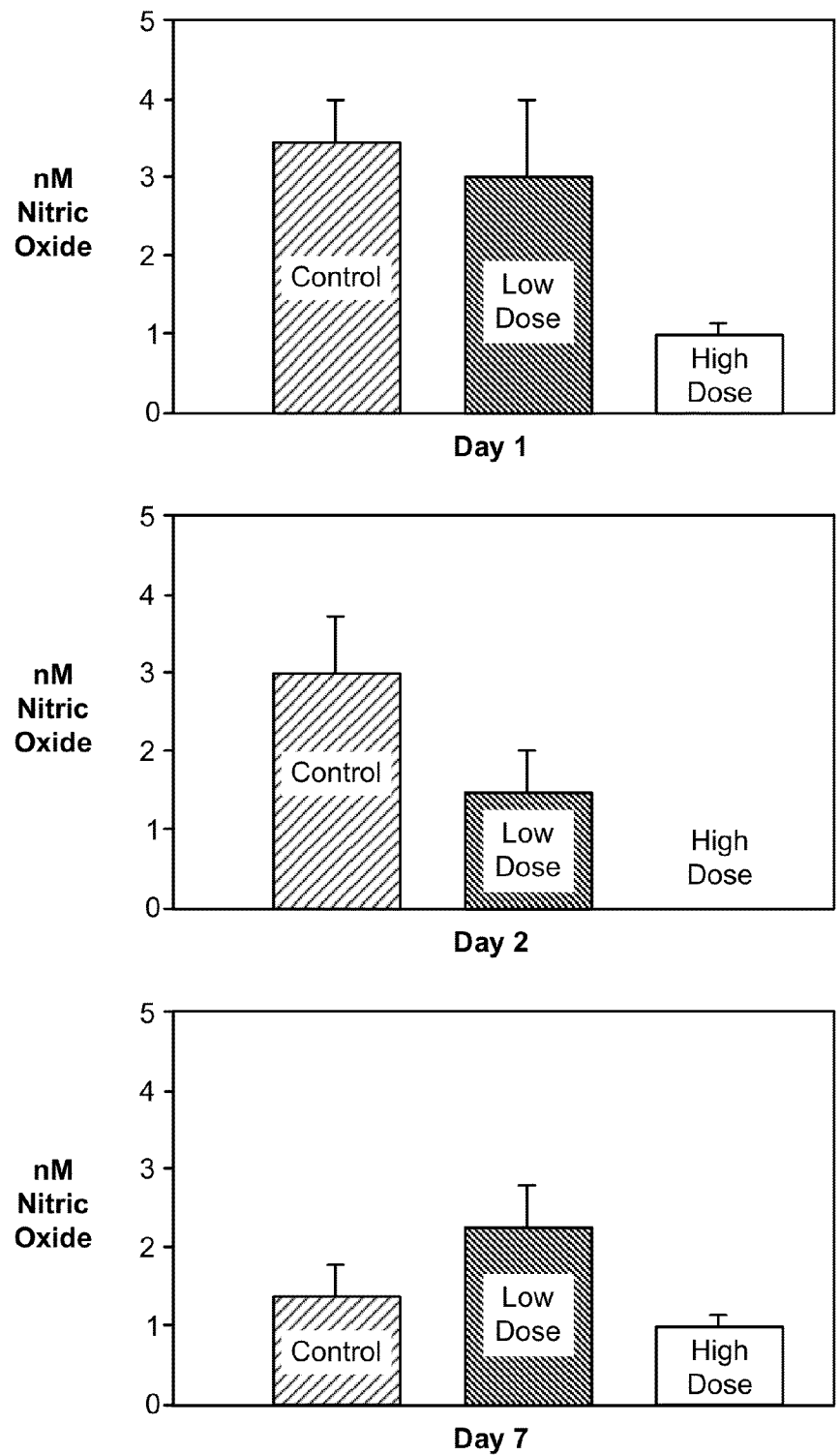

FIG. 30 contains graphs plotting nitric oxide release from untreated SH-SY5Y cells challenged with $10^{-6}$ M morphine (grey bar) prior to measuring nitric oxide release or from SH-SY5Y cells treated with $10^{-6}$ M morphine (black bar) or $10^{-8}$ M morphine (white bar). The results in the top, middle, and bottom panels were for cells treated as indicated for one, two, or seven days, respectively.

Figure 31:
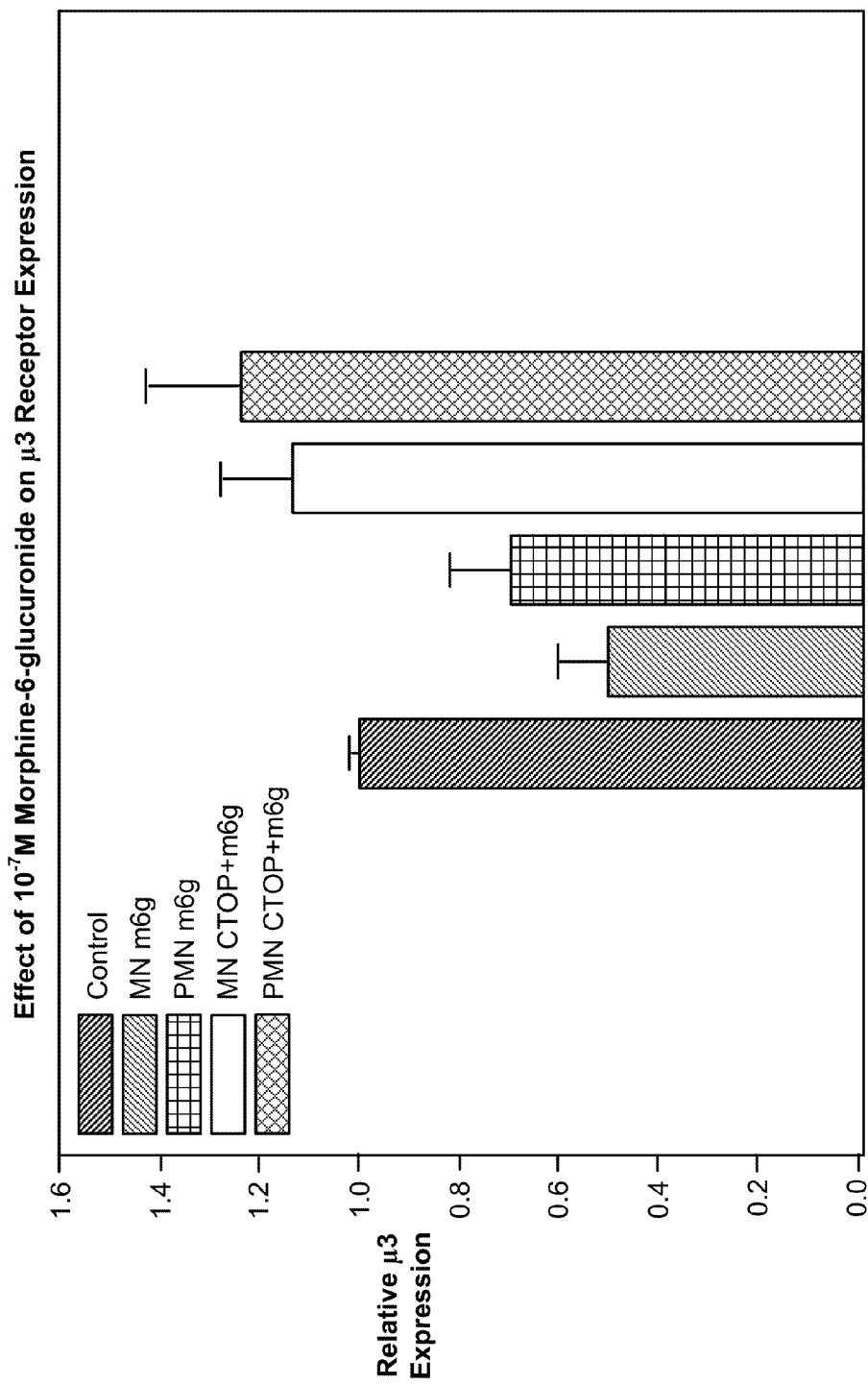

FIG. 31 is a graph plotting the relative mu3 opiate receptor gene expression in mononuclear cells (MN) and polymorphonuclear cells (PMN) treated with $10^{-7}$ M morphine-6-glucuronide alone or $10^{-7}$ M morphine-6-glucuronide and $10^{-6}$ M CTOP.

Figure 32:
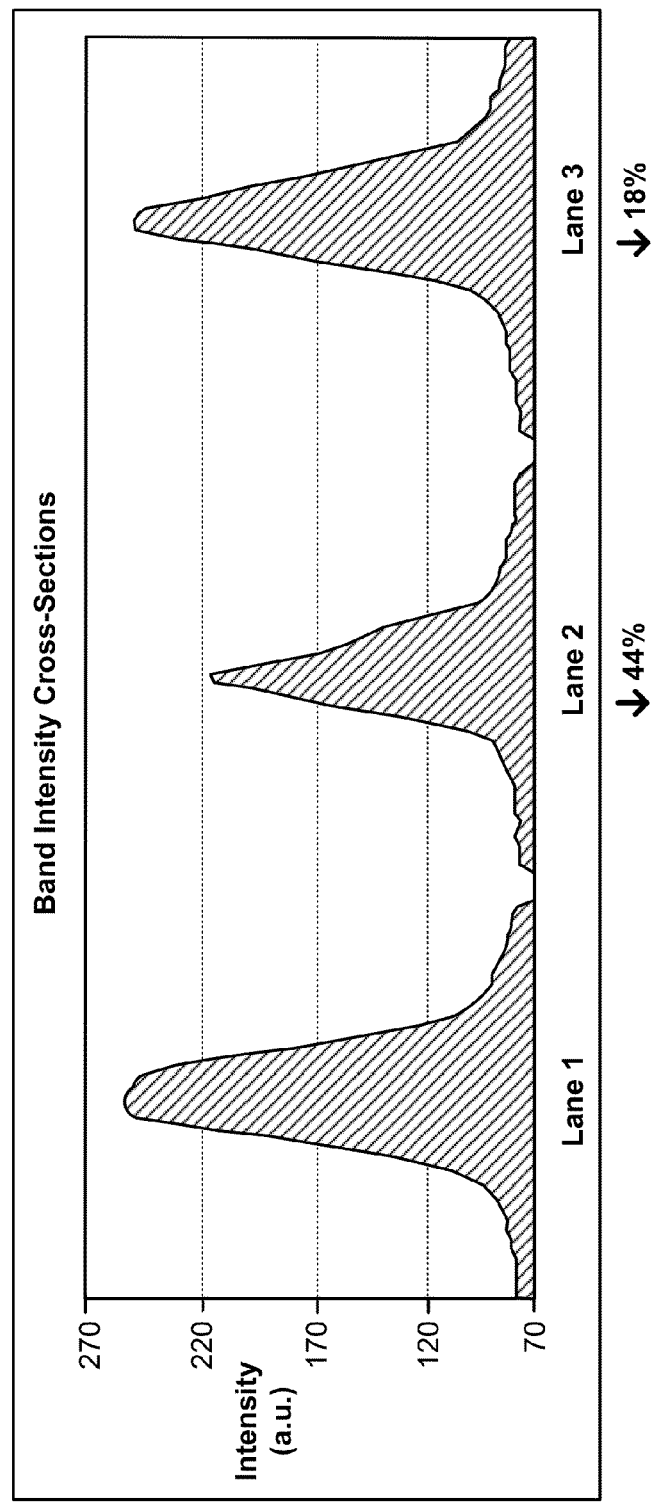

FIG. 32 is a graph plotting band intensities for BACE-1 gene expression in HTB-11 neuroblastoma cells. Lane 1: untreated cells; lane 2: 24-hour treatment with 1 μM morphine; lane 3: 24-hour treatment with 5 μM morphine.

Figure 33:
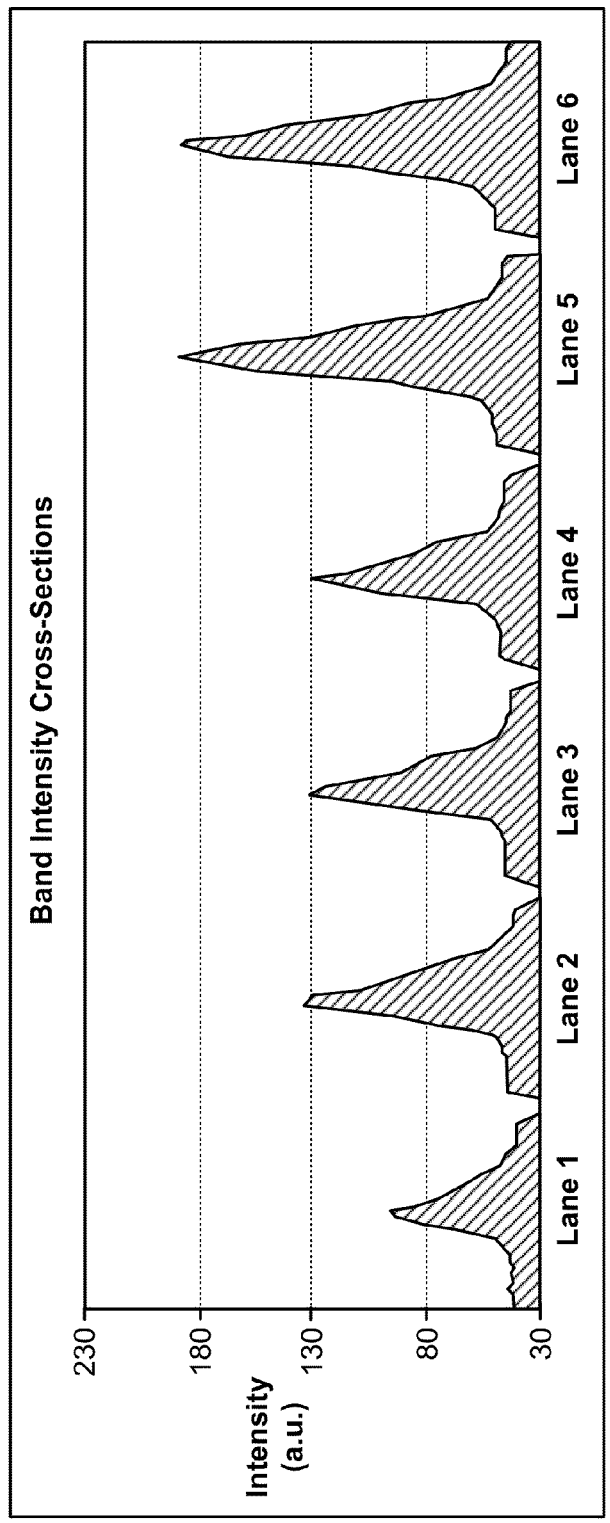

FIG. 33 is a graph plotting band intensities for BACE-2 gene expression in HTB-11 neuroblastoma cells treated as follows for 24 hours. Lane 1: untreated; lane 2: 1 μM morphine; lanes 3 and 4: 10 μM and 25 μM $A\beta_{1-42}$; lanes 5 and 6: 1 μM morphine with 10 μM and 25 μM $A\beta_{1-42}$.

FIG. 34 (top) is a graph plotting band intensities for BACE-1 and BACE-2 gene expression in HTB-11 neuroblastoma cells treated as follows for 24 hours. Lanes 1 and 4: untreated; lane 2 and 5: 1 μM morphine; lane 3 and 6: 1 μM morphine pre-treated with 10 μM naloxone for twenty minutes. Lanes 1-3 contain products amplified with primers specific for BACE-1, while lanes 4-6 contain products amplified with primers specific for BACE-2. FIG. 34 (bottom) is a graph plotting BACE expression levels standardized against cyclophilin expression.

FIG. 35 (top) is a graph plotting band intensities for BACE-1 and BACE-2 gene expression in HTB-11 neuroblastoma cells treated as follows for 24 hours. Lanes 1 and 4: untreated; lane 2 and 5: 1 μM morphine; lane 3 and 6: 1 μM morphine pre-treated with 10 μM L-NAME for twenty minutes. Lanes 1-3 contain products amplified with primers specific for BACE-1, while lanes 4-6 contain products amplified with primers specific for BACE-2. FIG. 35 (bottom) is a graph plotting BACE expression levels standardized against cyclophilin expression.

Figure 36:
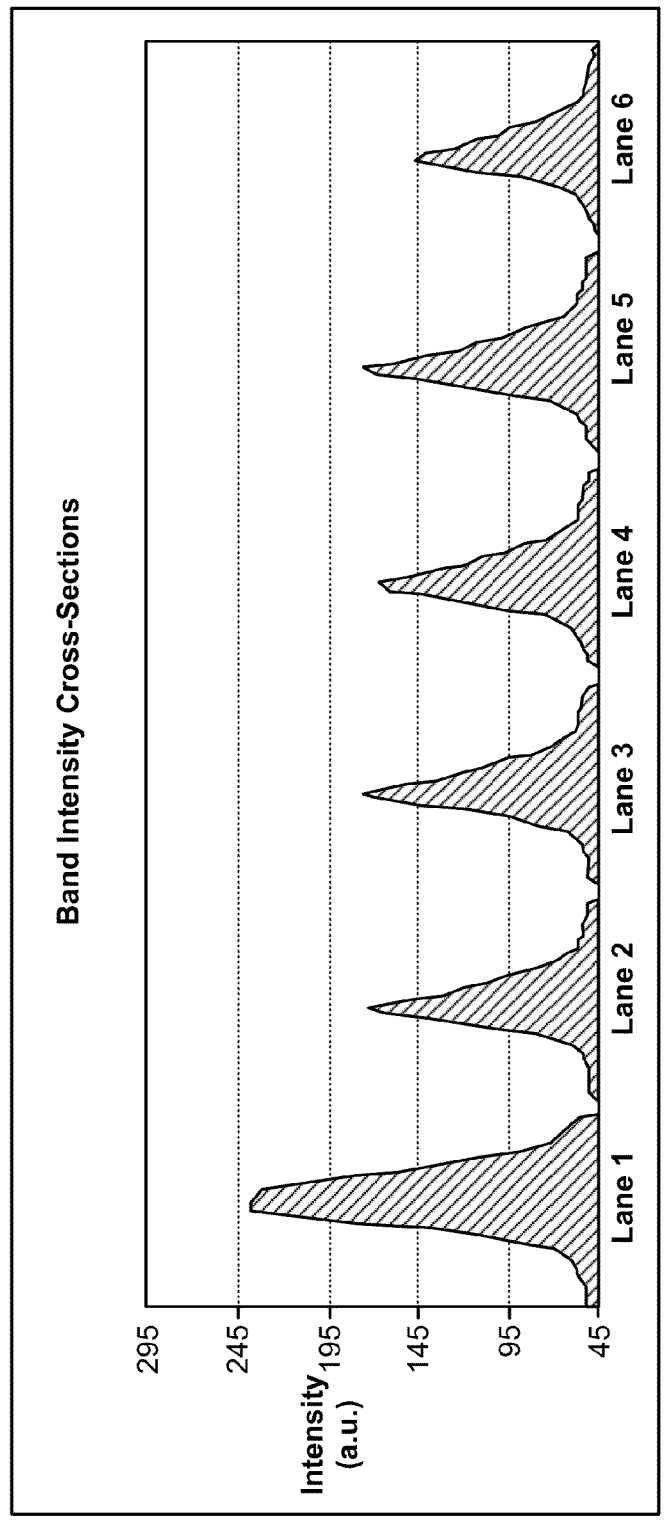

FIG. 36 is a graph plotting band intensities for BACE-1 gene expression in HTB-11 neuroblastoma cells treated as follows for 4 hours. Lane 1: untreated; lane 2, 3, and 4: 1 μM, 5 μM, and 10 μM SNAP; lane 5: 25 μM $A\beta_{1-42}$ with 1 μM SNAP; lane 6: 25 μM $A\beta_{1-42}$ with 10 μM SNAP.

Figure 37:
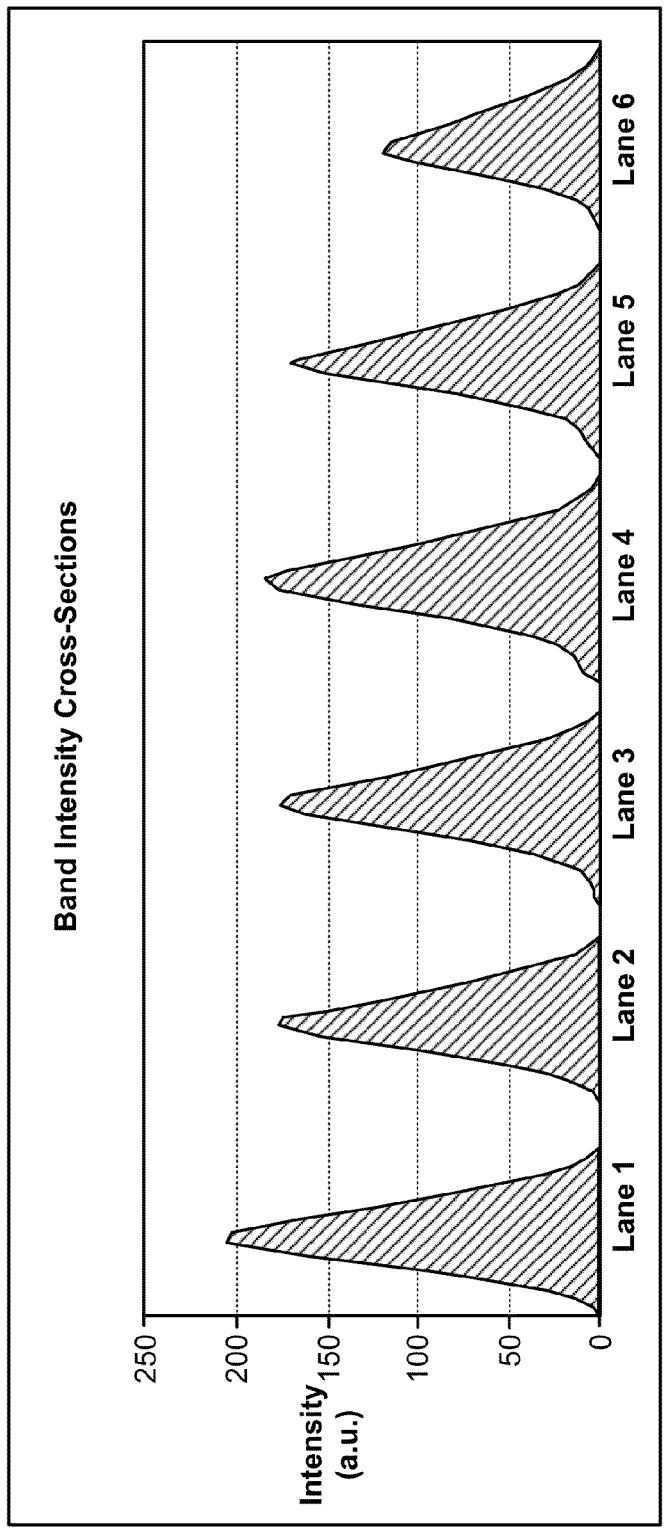

FIG. 37 is a graph plotting band intensities for BACE-1 gene expression in HTB-11 neuroblastoma cells treated as follows for 24 hours. Lane 1: untreated; lane 2, 3, and 4: 1 μM, 5 μM, and 10 μM SNAP; lane 5: 25 μM $A\beta_{1-42}$ with 1 μM SNAP; lane 6: 25 μM $A\beta_{1-42}$ with 10 μM SNAP.

Figure 38:
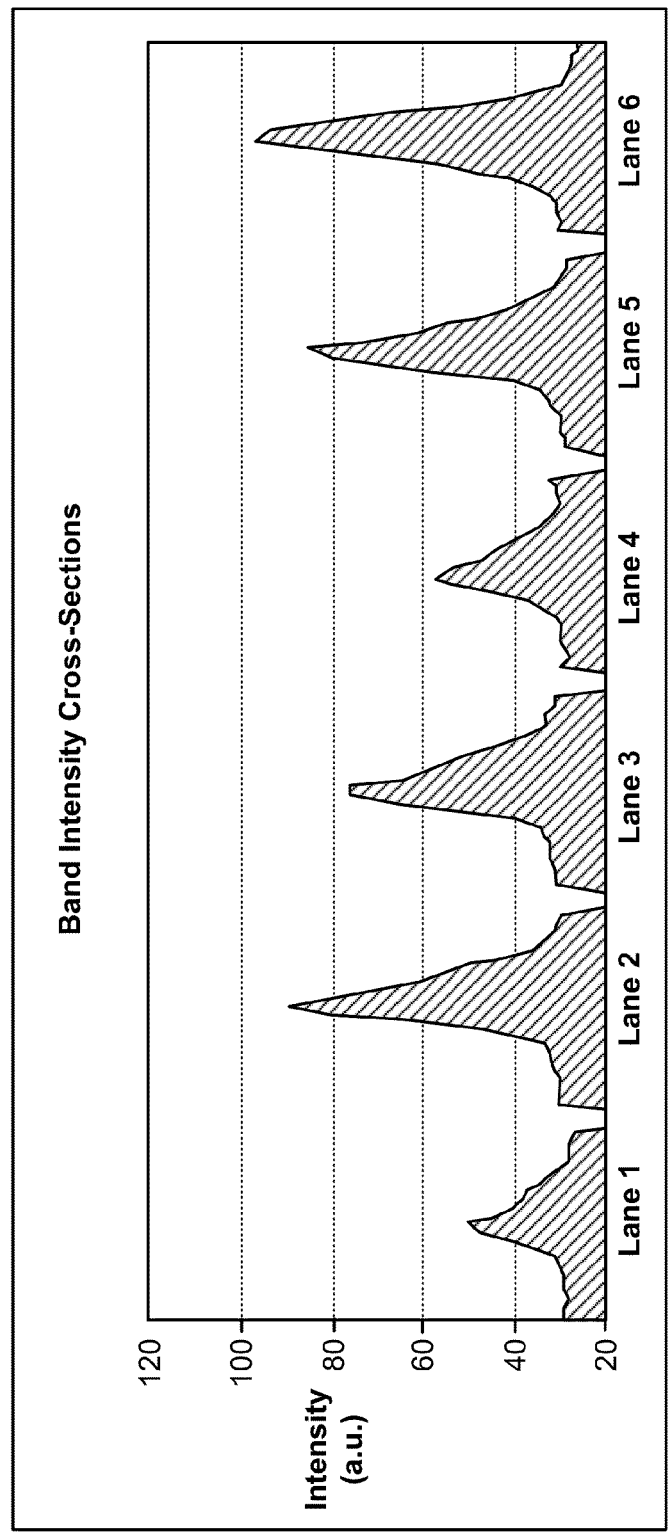

FIG. 38 is a graph plotting band intensities for BACE-2 gene expression in HTB-11 neuroblastoma cells treated as follows for 4 hours. Lane 1: untreated; lane 2, 3, and 4: 1 μM, 5 μM, and 10 μM SNAP; lane 5: 25 μM $A\beta_{1-42}$ with 1 μM SNAP; lane 6: 25 μM $A\beta_{1-42}$ with 10 μM SNAP.

Figure 39:
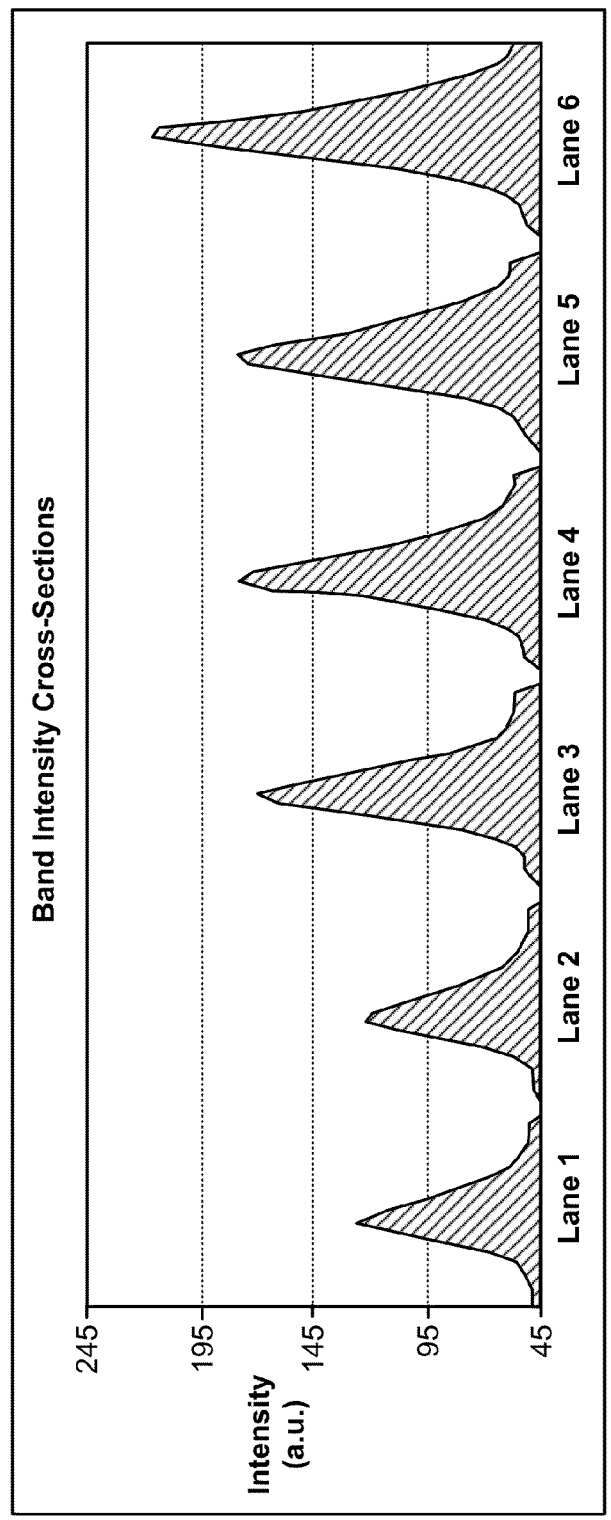

FIG. 39 is a graph plotting band intensities for BACE-2 gene expression in HTB-11 neuroblastoma cells treated as follows for 24 hours. Lane 1: untreated; lane 2, 3, and 4: 1 μM, 5 μM, and 10 μM SNAP; lane 5: 25 μM $A\beta_{1-42}$ with 1 μM SNAP; lane 6: 25 μM $A\beta_{1-42}$ with 10 μM SNAP.

Figure 40:
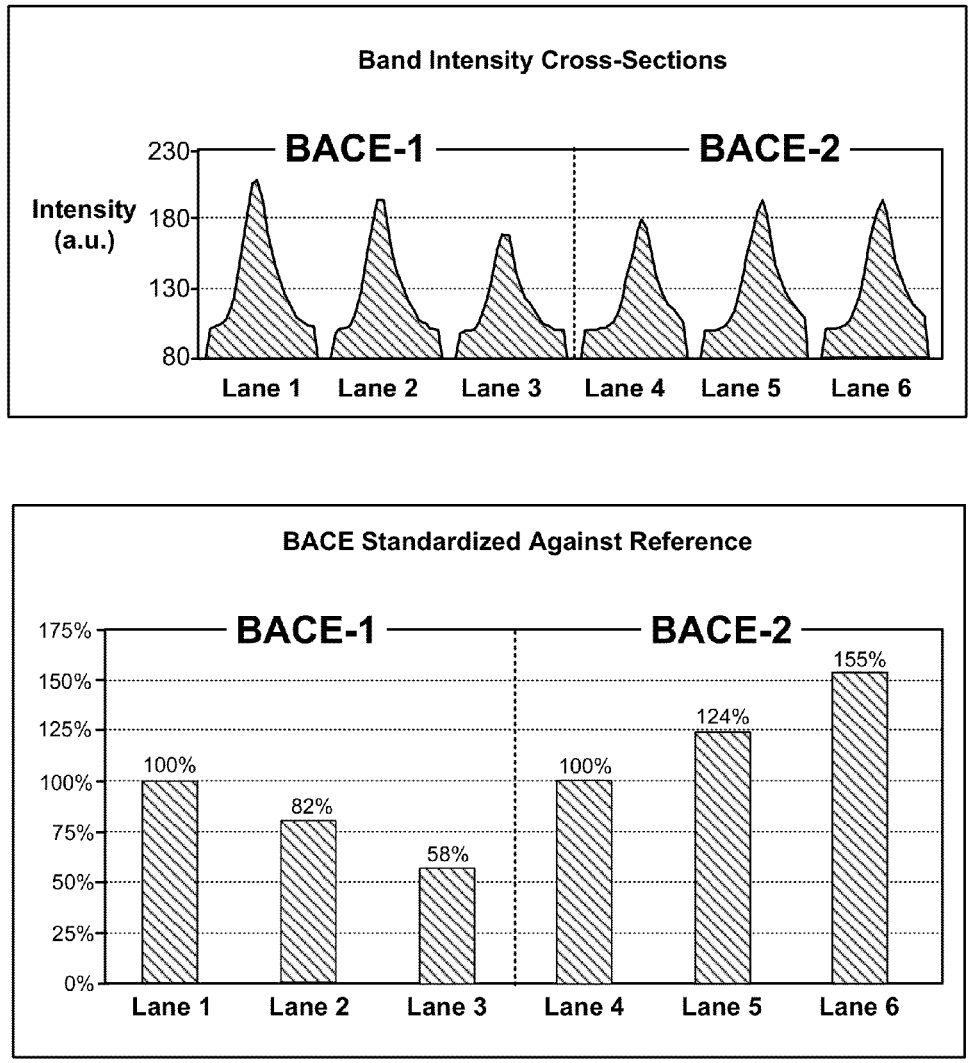

FIG. 40 is a graph plotting band intensities for BACE-1 and BACE-2 gene expression in HTB-11 neuroblastoma cells treated as follows for 2 hours. Lanes 1 and 4: untreated; lane 2 and 5: 1 μM SNAP; lane 3 and 6: 5 μM SNAP. Lanes 1-3 contain products amplified with primers specific for BACE-1, while lanes 4-6 contain products amplified with primers specific for BACE-2. FIG. 40 (bottom) is a graph plotting BACE expression levels standardized against β-actin expression.

Figure 41:
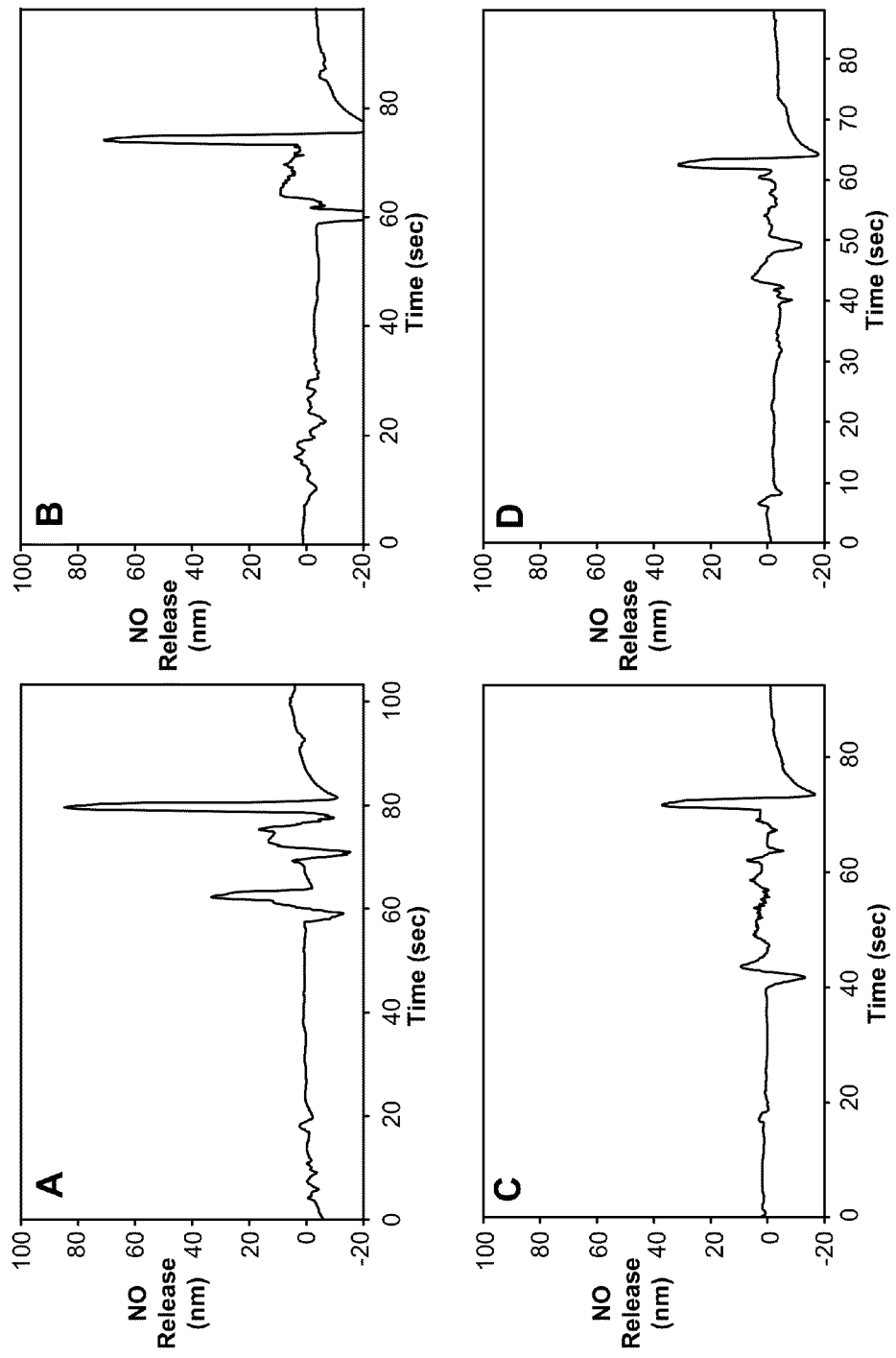

FIG. 41 contains graphs plotting real-time NO release from SH-SY5Y neuroblastoma cells pre-treated for 1 hour with the following amounts of $A\beta_{1-42}$ and then stimulated using 1 μM M6G at t=0. Panel A: control, 0 $A\beta_{1-42}$; Panel B: 1μ $A\beta_{1-42}$; Panel C: 5 μM $A\beta_{1-42}$; Panel D: 10 μM $A\beta_{1-42}$; Panel E: 15 μM $A\beta_{1-42}$; Panel F: 25 mM $A\beta_{1-42}$; Panel G: control with L-NAME added 4 minutes before M6G.

Figure 42:
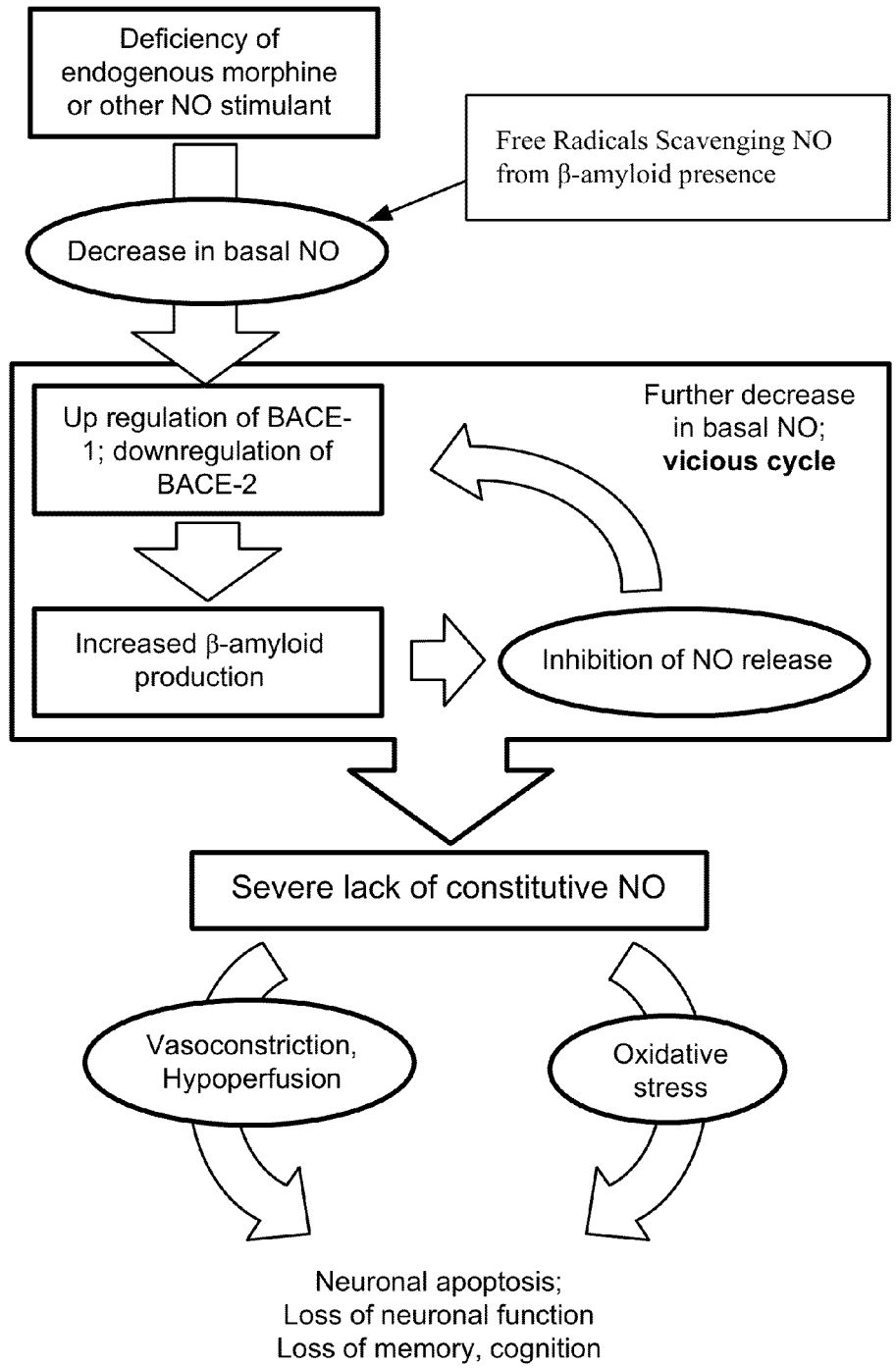

FIG. 42 is a diagram of the possible role of NO in Alzheimer's disease.

Figure 43:
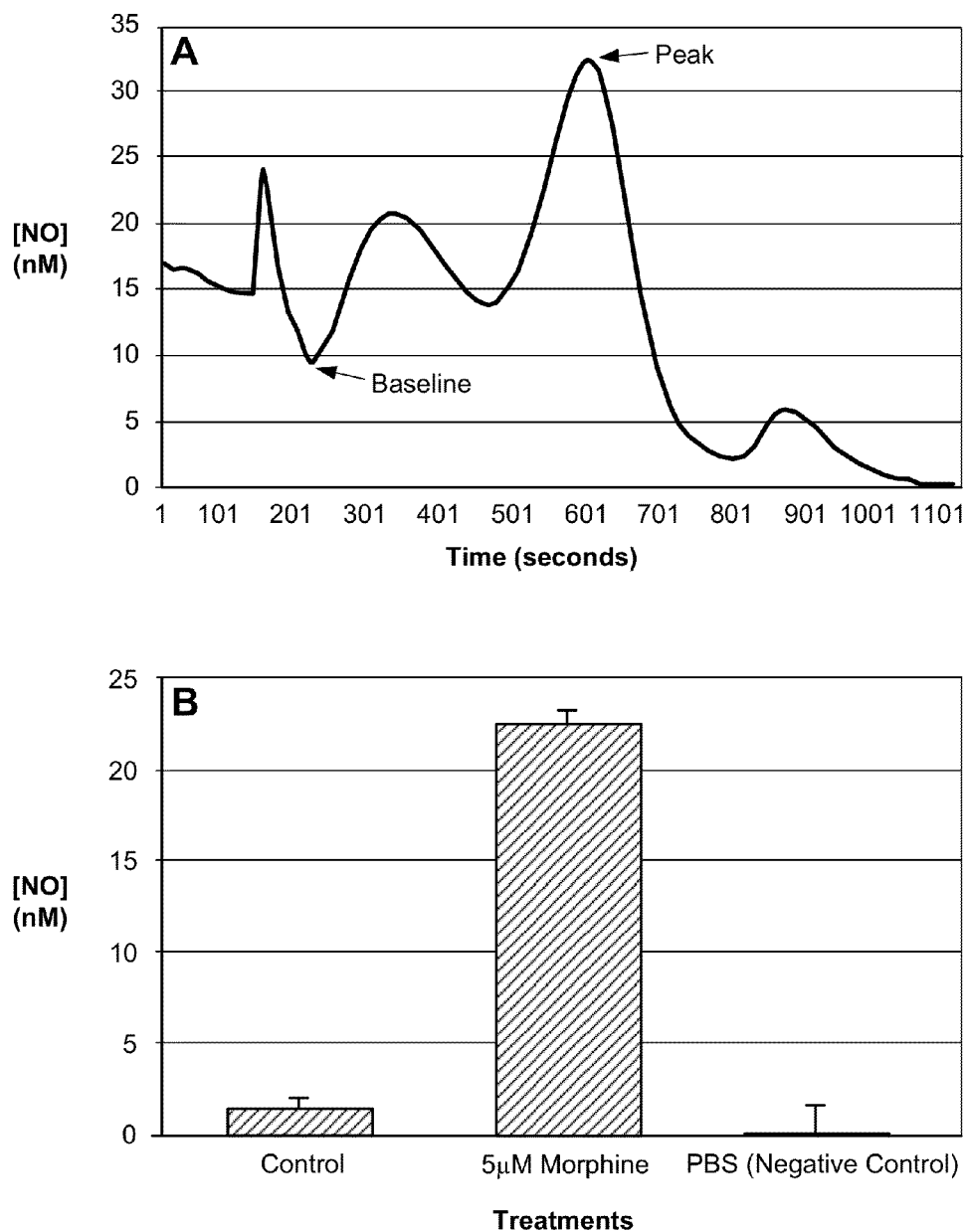

FIG. 43A is a graph plotting NO release from human neuroblastoma cells treated with morphine sulfate (5 µM) versus time. FIG. 43B is a bar graph plotting the peak NO release for human neuroblastoma cells treated with morphine sulfate (5 µM) or PBS. The control is the peak value of NO release from cells prior to adding morphine (i.e., basal NO release). The peak value is 22.3 nM±0.85 ($p<0.001$ when compared to control).

Figure 44:
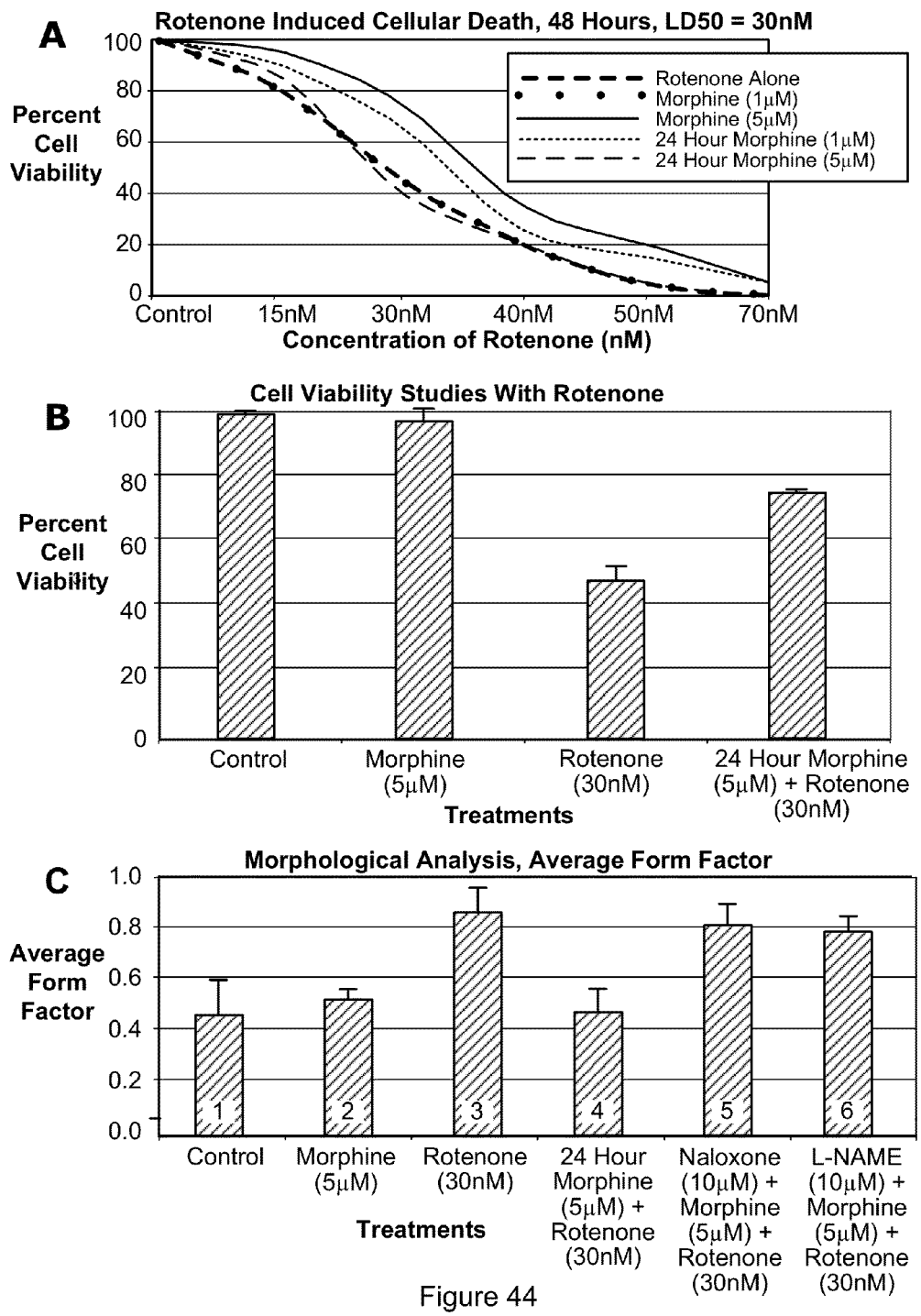
Figure 44:
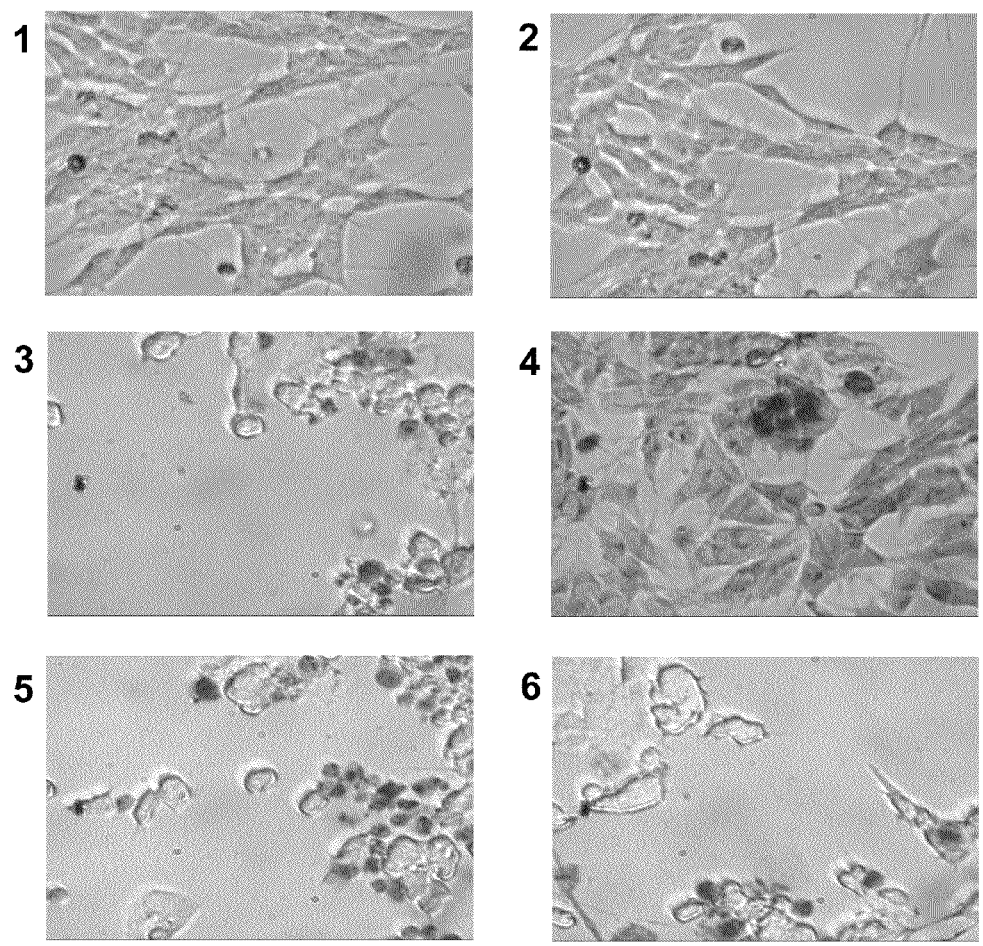

FIG. 44A is a graph plotting percent cell viability for cells receiving the indicated treatment and either 0, 15, 30, 40, 50, or 70 µM of rotenone for 48 hours. FIG. 44B is a bar graph plotting cell viability for cells treated as indicated. FIG. 44C is a graph plotting the average form factor measurement for cells treated as indicated. Photographs 1-6 of FIG. 44 are pictures of cells corresponding to the treatments indicated in FIG. 44C.

Figure 45:
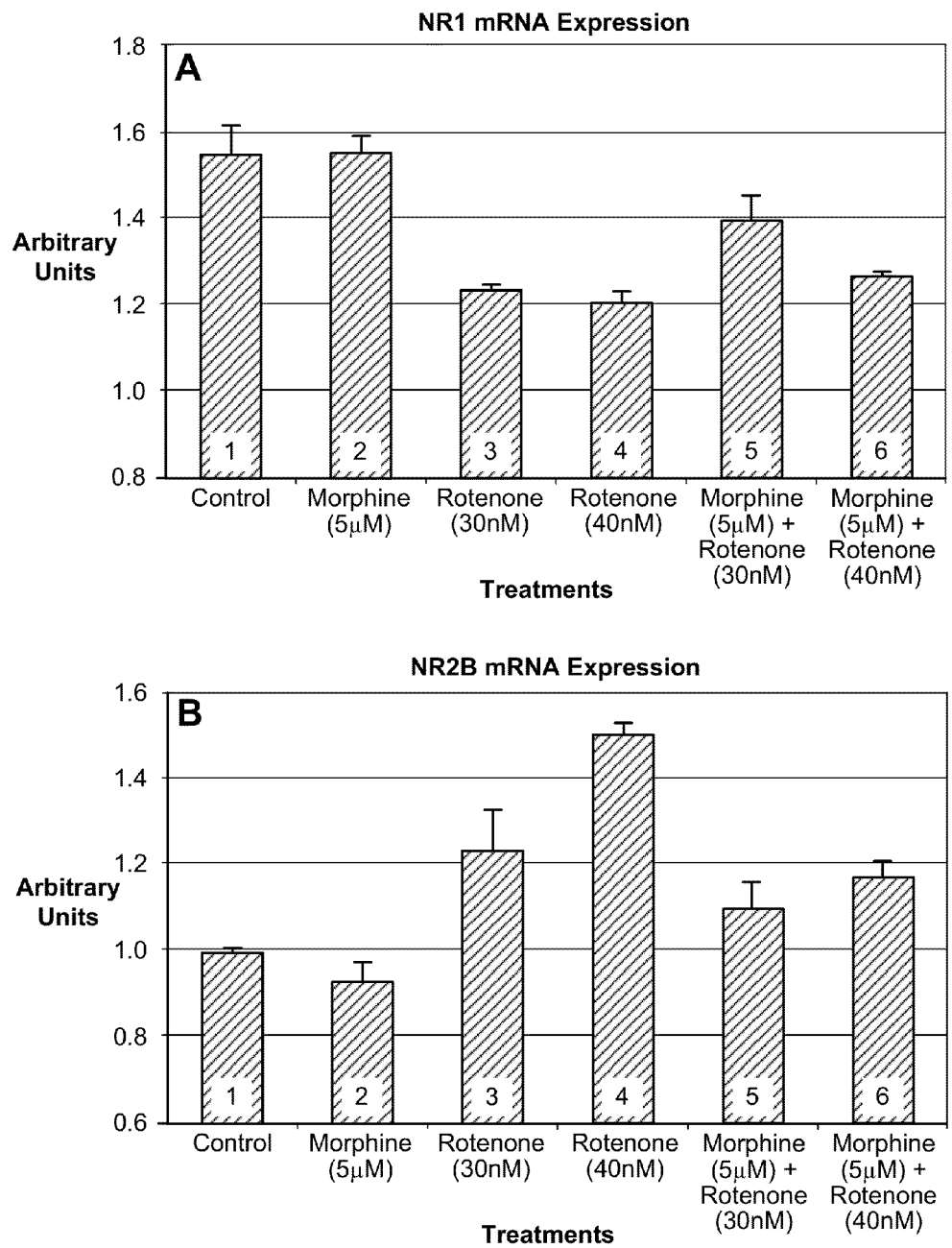

FIG. 45A is a graph plotting NR1 expression levels, while FIG. 45B is a graph plotting NR2B expression levels for the following treatments: treatment #1: control; treatment #2: morphine (5 µM); treatment #3: rotenone (30 nM, $LD_{50}$); treatment #4: rotenone (40 nM); treatment #5: morphine+rotenone (30 nM); and treatment #6: morphine+rotenone (40 nM). Rotenone treatment caused a dose dependent decrease in NR1 expression ($p<0.003$, both 3 and 4 compared to 1). Morphine increased NR1 expression at $LD_{50}$ ($p<0.035$, 5 compared to 3). Rotenone caused a dose dependent increase in NR2B expression ($p<0.001$, 3 compared to 1). Morphine decreased NR2B expression and counteracted the effects of rotenone in a dose dependent manner ($p<0.042$, 5 compared to 3, and $p<0.018$, 6 compared to 4, respectively).

Figure 46:
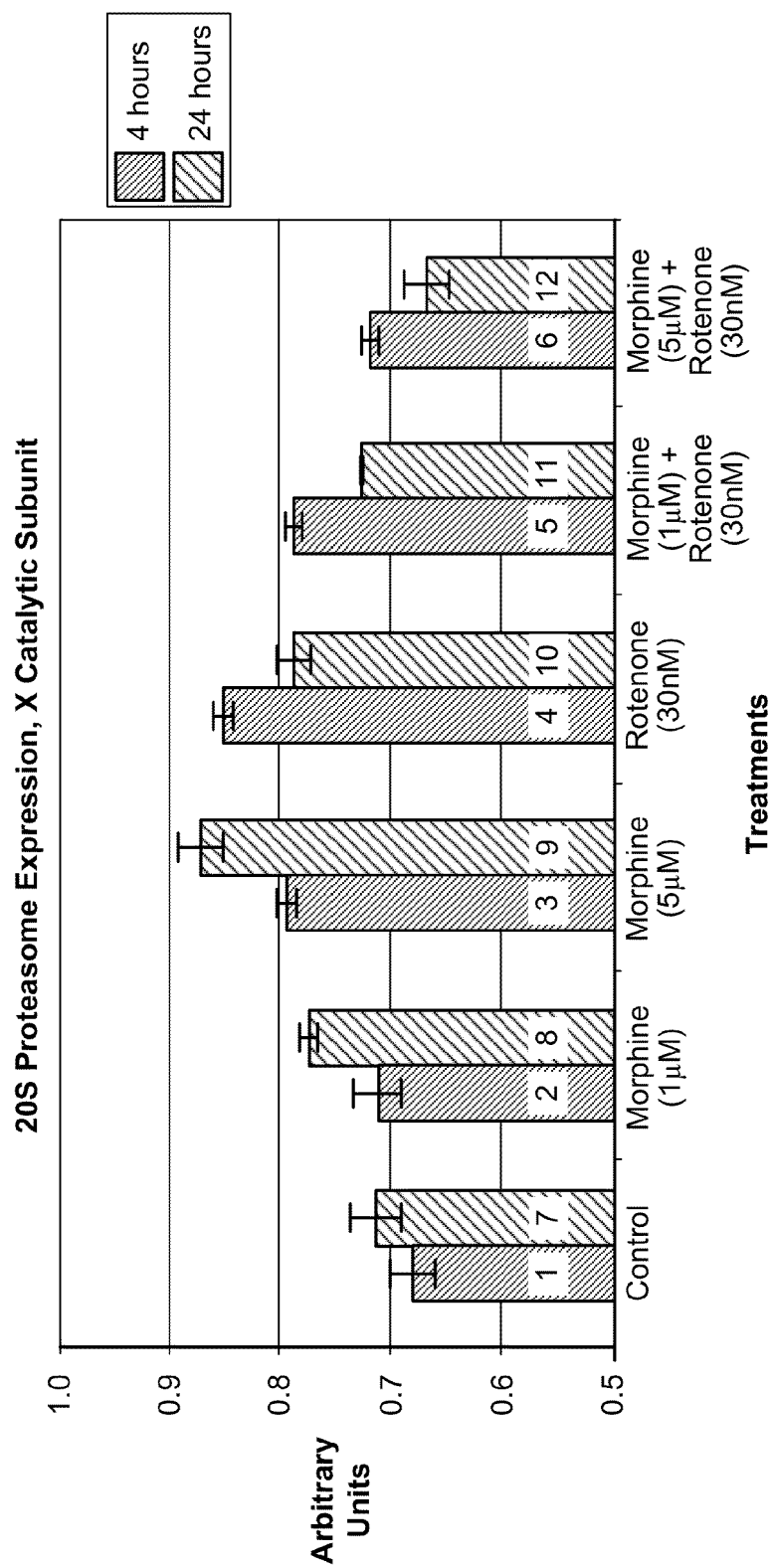

FIG. 46 is a graph plotting proteasomal catalytic X subunit expression levels in cells treated as indicated for 4 or 24 hours. Morphine increased the level of expression of the X subunit in a dose dependent manner. The 5 nM morphine treatment in the presence of rotenone significantly decreases the expression of the X subunit and was significant when compared to rotenone alone, $p<0.014$ at 4 hours, and $p<0.009$ at 24 hours. Rotenone also increased the level of X subunit expression ($p<0.006$ at 4 hours) and ($p<0.033$ at 24 hours). Neuroprotection was observed with the dose dependent decrease in the level of proteasomal catalytic X subunit expression being significant at 5 nM of morphine when compared to treatments with rotenone alone ($p<0.01$ at 4 hours and $p<0.012$ at 24 hours). The values obtained with 5 µM of morphine plus 30 nM retenone were not statistically different from control values.

Figure 47:
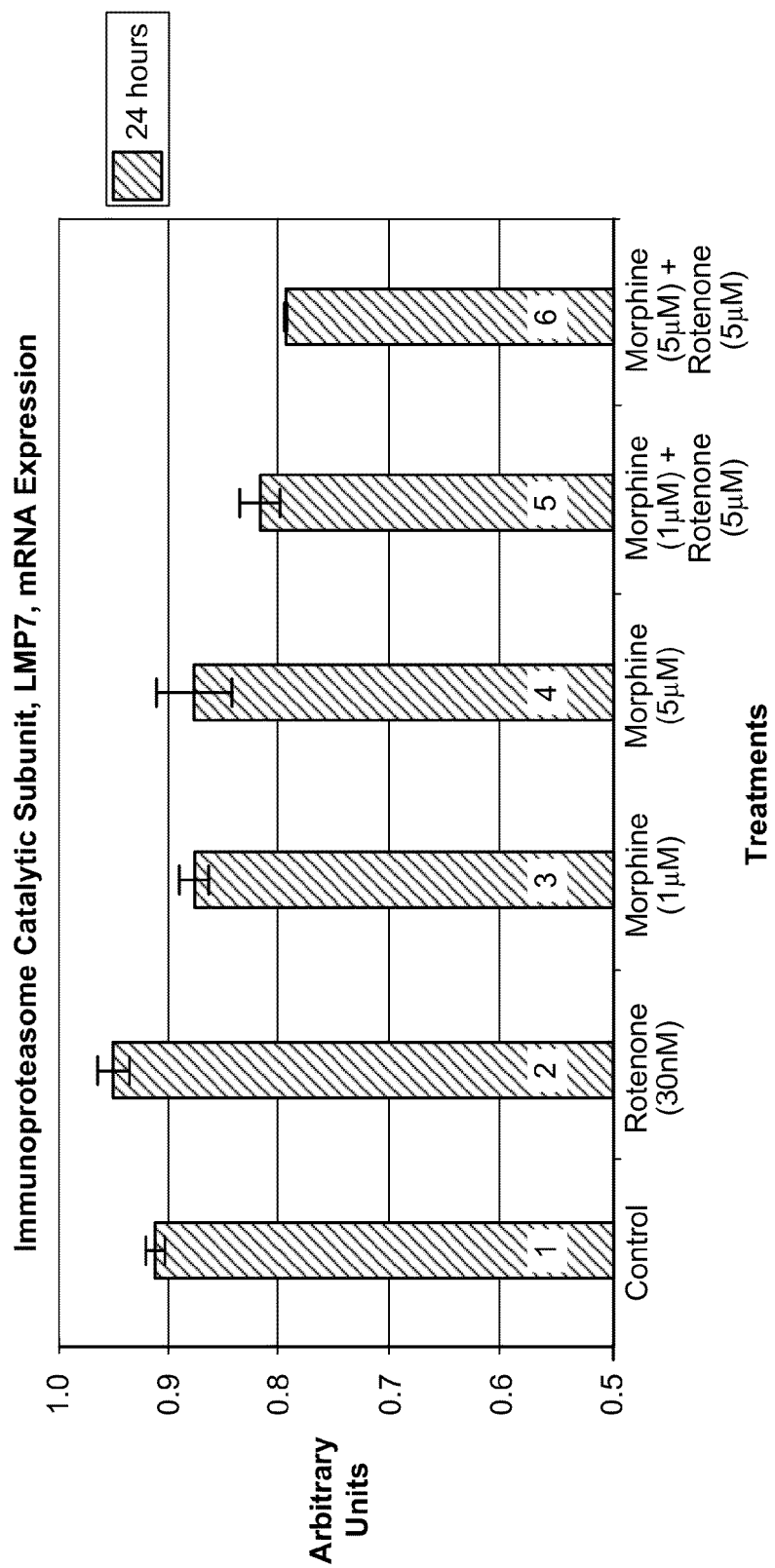

FIG. 47 is a graph plotting mRNA expression of the LMP7 immunoproteasome subunit in cells treated as indicated for 24 hours. Although rotenone did not cause significant increase in expression ($p<0.068$), there was a significant, dose dependent decrease in LMP7 expression with morphine administration when rotenone values were compared to morphine+rotenone values: $p<0.026$ with 1 µM morphine and $p<0.018$ with 5 µM morphine.

Figure 48:
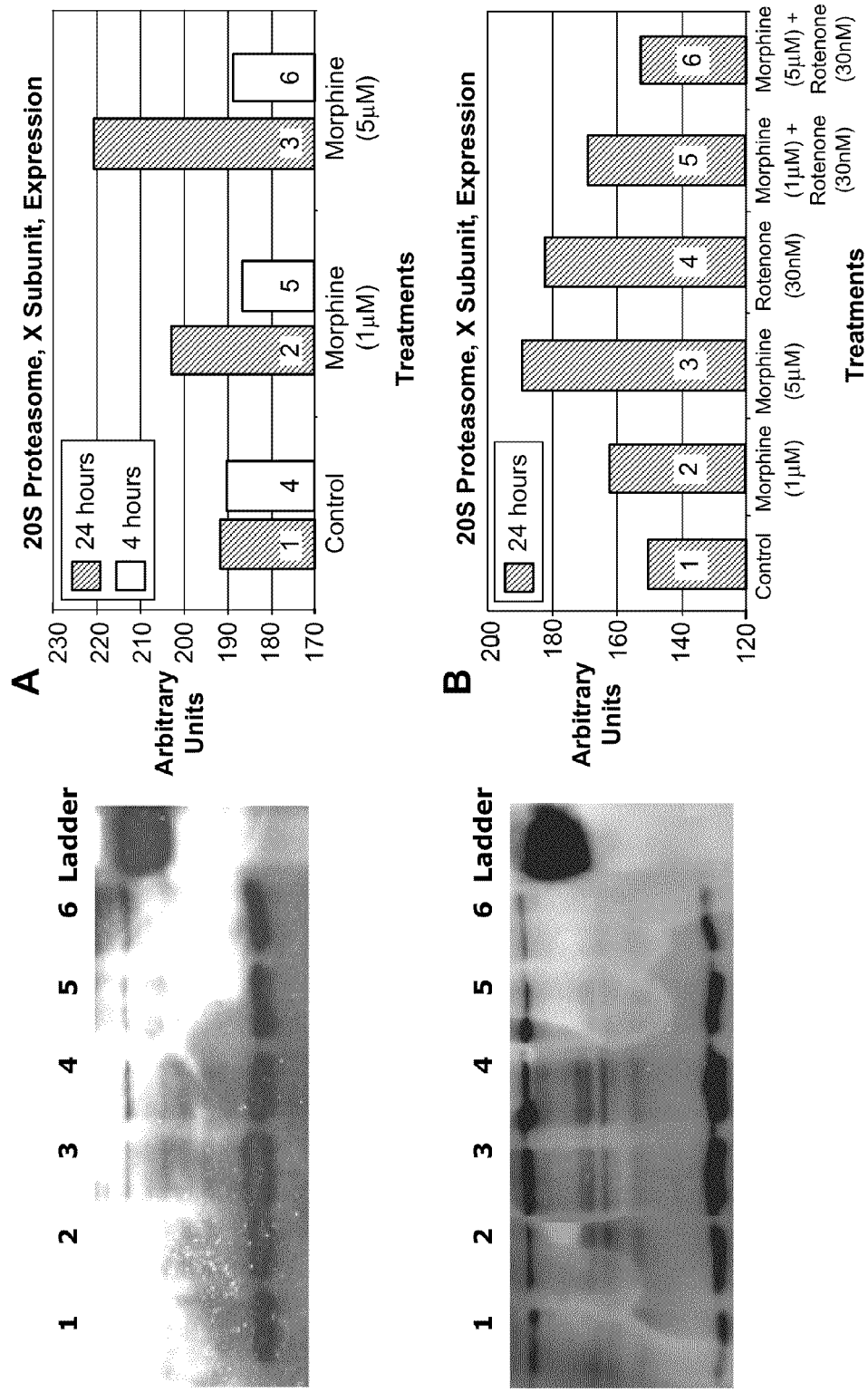

FIG. 48 contains photographs of Western blots and graphs plotting the expression levels of 20S proteasome X subunit polypeptides in cells treated as indicated. Morphine induced a significant dose dependent increase in expression of X subunit after 24 hours of treatment, $p<0.01$ (1 µM morphine compared to control) and $p<0.001$ (5 µM morphine compared to control). Significant neuroprotection was observed with 5 µM morphine when compared to rotenone control ($p<0.028$). Furthermore, this treatment, 5 µM morphine+30 nM rotenone, was not statistically different from the control ($p<0.065$).

Figure 49A:
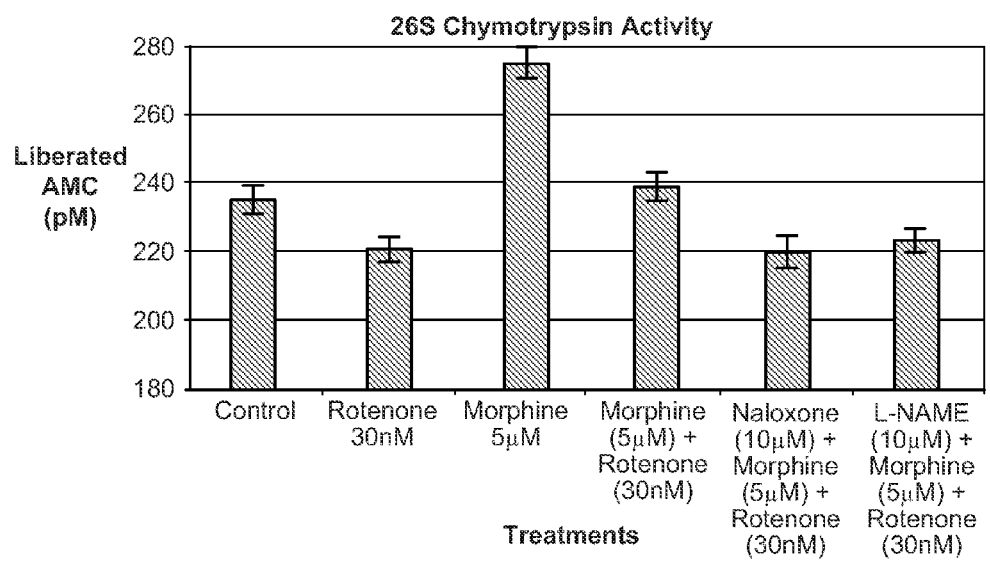
Figure 49B:
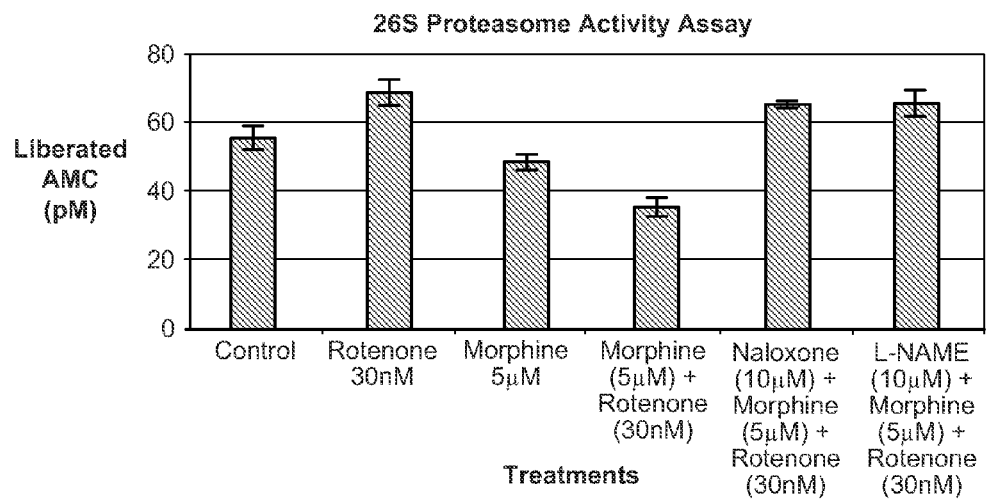

FIG. 49A is a graph plotting 26s chymotrypsin activity, while FIG. 49B is a graph plotting 20S proteasome activity. Cells were treated with or without morphine (5 µM), rotenone (30 nM), naloxone (10 µM), and L-NAME (10 µM). A significant decrease in chymotrypsin 26S activity was caused by rotenone ($p<0.043$). A significant increase in chymotrypsin activity was caused by morphine (5 µM) ($p<0.021$). Concomitant treatment of morphine and rotenone resulted in a restoring of chymotrypsin activity to the point where it was statistically insignificant to the control. Significant increase in activity of the 20S proteasome upon exposure to rotenone was observed ($p<0.046$). Coupled with the morphine induced decrease in 20S proteasomal function ($p<0.050$), there was a significant decrease in 20S activity ($p<0.034$).

Figure 50:
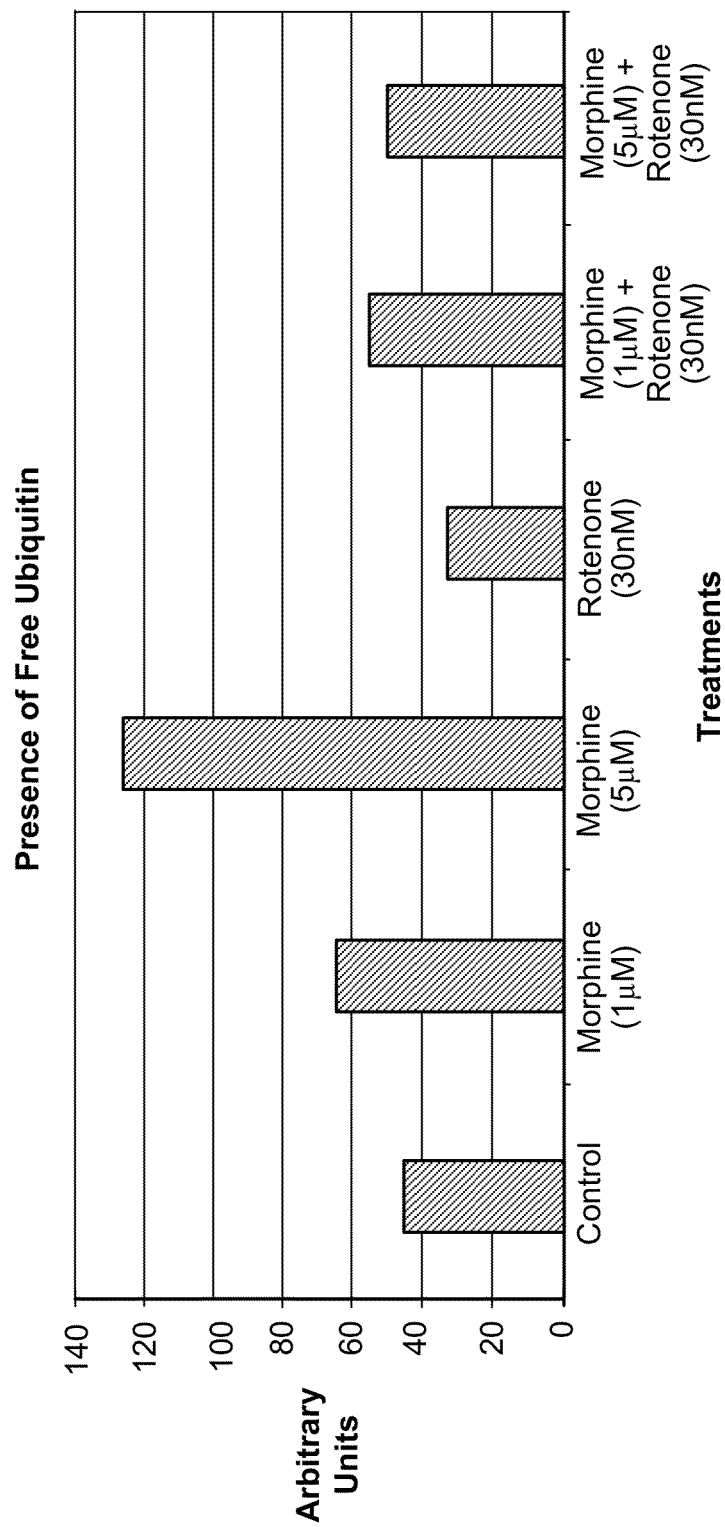

FIG. 50 is a graph plotting the level of free ubiquitin in cells treated as indicated using Western blot analysis. A significant dose dependent increase in the level of free ubiquitin was observed with morphine treatment ($p<0.001$ with 5 µM morphine). A decrease was observed in the level of ubiquitin with rotenone treatment ($p<0.064$), and this was reversed with the administration of morphine ($p<0.039$ when compared to rotenone treatment).

Figure 51:
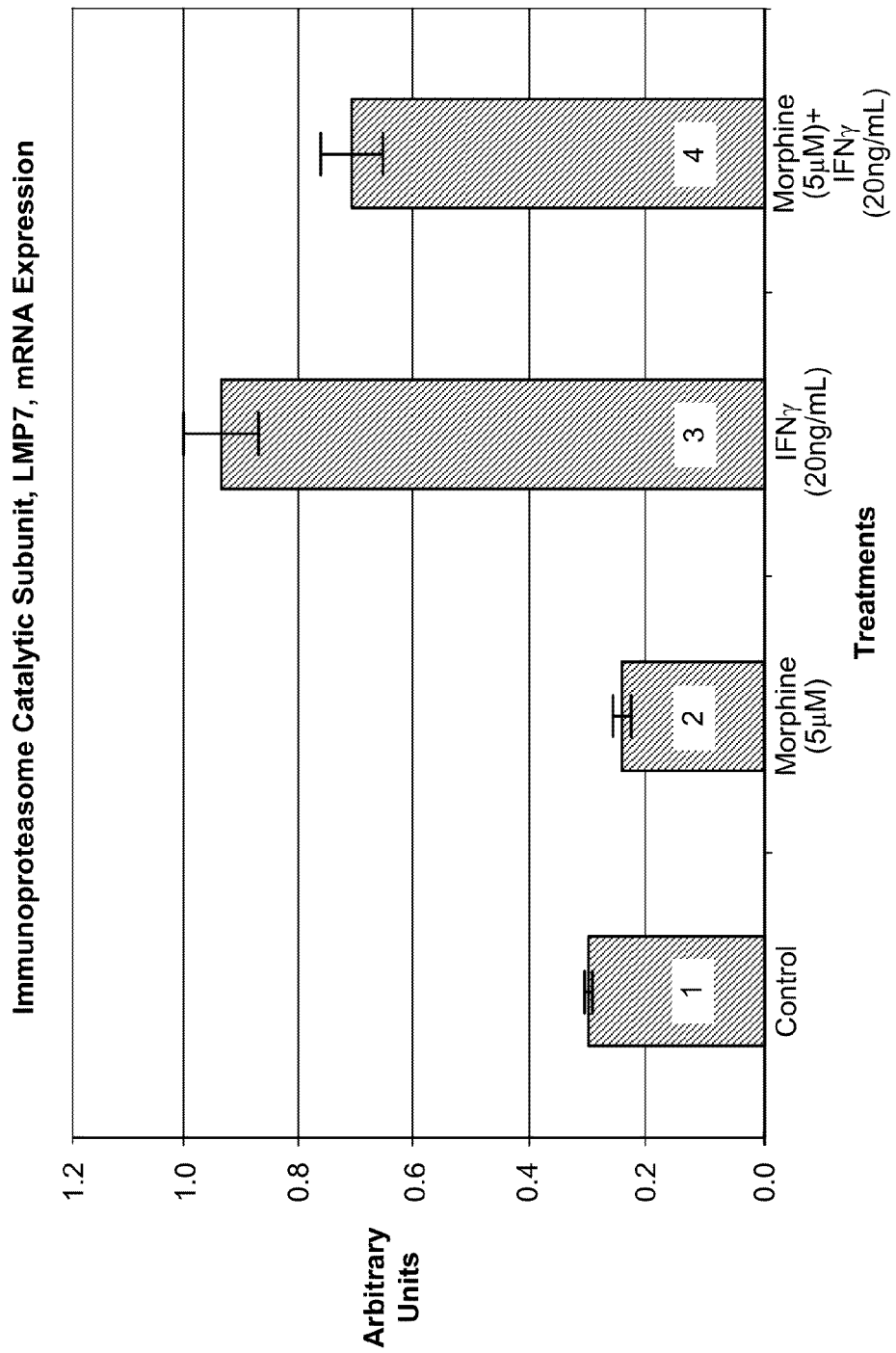

FIG. 51 is a graph plotting the level of LMP7 mRNA expression in cells treated as indicated. IFNγ (20 ng/mL) caused in increase in expression of the LMP7 immunoproteasome subunit ($p<0.001$). Concomitant morphine administration with IFNγ produced significant neuroprotection ($p<0.034$).

Figure 52:
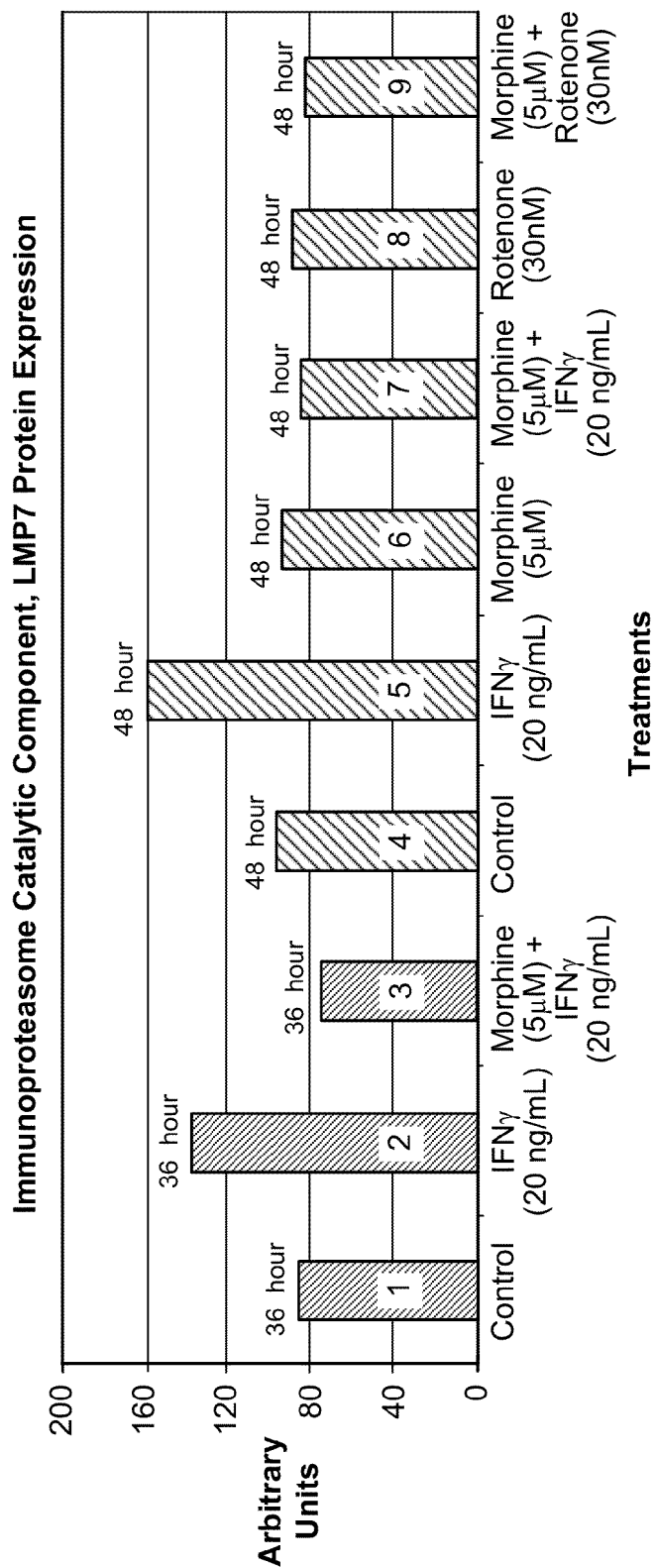

FIG. 52 is a graph plotting the level of LMP7 polypeptide expression in cells treated as indicated. IFNγ caused an increase in LMP7 polypeptide expression ($p<0.001$). Morphine was able to counteract this effect in concomitant treatment with IFNγ ($p<0.001$ compared to IFNγ at both 36 hours and 48 hours).

DETAILED DESCRIPTION

This document provides methods and materials related to using morphine, morphine precursors (e.g., tyrosine, tyramine, phenyl alanine, 3,4 dihydroxyphenyl pyruvate, dihydroxyphenyl acetaldehyde, dopamine, L-DOPA, reticuline, norlaudanosoline, salutaridine, thebaine, or codeine), morphine-6β-glucuronide, inhibitors of morphine synthesis or activity, and inhibitors of dopamine synthesis to treat diseases, to reduce inflammation, or to restore normal function. For example, this document provides compositions containing morphine, morphine precursors, morphine-6β-glucuronide, inhibitors of morphine synthesis, inhibitors of morphine activity, inhibitors of dopamine synthesis, or combinations thereof. This document also provides methods for using such compositions.

This document provides compositions containing morphine, morphine precursors, morphine-6β-glucuronide, or combinations thereof. Morphine or morphine-6β-glucuronide can be formulated into compositions designed to deliver a low dose of morphine or morphine-6β-glucuronide to a mammal. Typically, a low dose of morphine is a dose that is below that which is given to relieve a mammal of pain. For example, a low dose of morphine can be between 0.5 and 10 µg (e.g., between 1 and 9 µg, between 1 and 8 µg, between 1 and 7 µg, between 1 and 6 µg, between 1 and 5 µg, between 2 and 10 µg, between 3 and 10 µg, between 4 and 10 µg, or between 5 and 10 µg) per kg of body weight per day. A low level of morphine-6β-glucuronide can be similar to those of morphine. For example, a low dose of morphine-6β-glucuronide can be between 1 and 10 µg (e.g., between 1 and 9 µg, between 1 and 8 µg, between 1 and 7 µg, between 1 and 6 µg, between 1 and 5 µg, between 2 and 10 µg, between 3 and 10 µg, between 4 and 10 µg, or between 5 and 10 µg) per kg of body weight per day. In some cases, morphine or morphine-6β-glucuronide can be formulated to deliver between 35 and 700 µg of morphine or morphine-6β-glucuronide for a 70 kg individual. In some cases, a low dose can be any amount that is high enough to cause cells within the mammal to release nitric oxide yet low enough to not cause the mammal to experience analgesia. Such a dose can be, without limitation, about 5 µg per kg of body weight per day.

When given orally, morphine or morphine-6β-glucuronide can be formulated into a pill or tablet that contains between 10 and 1000 µg (e.g., between 10 and 900 µg, between 10 and 800 µg, between 10 and 700 µg, between 10 and 600 µg, between 10 and 500 µg, between 30 and 1000 µg, between 35 and 1000 µg, between 40 and 1000 µg, between 50 and 1000 µg, between 35 to 700 µg, or between 35 and 500 µg) of morphine or morphine-6β-glucuronide. For example, a tablet can be designed to contain 100 µg of morphine. In these cases, a mammal weighing about 70 kg can be instructed to take between one and three pills or tablets per day. Mammals weighing more or less than 70 kg can be instructed to take the appropriate number of pills or tablets to achieve a similar final concentration. The term "morphine" as used herein includes dihydromorphine, morphine sulfate, morphine hydrochloride, and morphine acetate.

The compositions provided herein can contain one or more than one (e.g., two, three, four, five, or more) morphine precursors without containing morphine or morphine-6β-glucuronide. Examples of morphine precursors include, without limitation, tyrosine, tyramine, dopamine, L-DOPA, 3,4 dihydroxyphenyl pyruvate, dihydroxyphenyl acetaldehyde, phenylalanine, reticuline, norlaudanosoline, salutaridine, thebaine, and codeine. As described herein, a composition can be designed to contain tyrosine, tyramine, dopamine, L-DOPA, 3,4 dihydroxyphenyl pyruvate, dihydroxyphenyl acetaldehyde, phenylalanine, reticuline, norlaudanosoline, salutaridine, thebaine, codeine, or combinations thereof. Such compositions can contain any amount of the morphine precursors such as an amount between 1 and 10 mg per person weighing about 70 kg. For example, a composition can contain between 1 and 10 mg of reticuline.

The compositions provided herein can contain one or more (e.g., two, three, four, five, or more) morphine precursors in addition to morphine or morphine-6β-glucuronide or in addition to a combination of morphine and morphine-6β-glucuronide. In some cases, a composition can contain morphine and reticuline. Compositions containing morphine and a morphine precursor as well as compositions containing morphine-6β-glucuronide and a morphine precursor can contain any amount of the morphine precursor such as between 0.1 and 100 mg (e.g., between 0.1 and 90 mg, between 0.1 and 75 mg, between 0.1 and 50 mg, between 0.1 and 25 mg, between 0.1 and 10 mg, between 0.5 and 100 mg, between 1 and 100 mg, between 1 and 50 mg, or between 1 and 10 mg) of the morphine precursor. For example, a composition can contain between 10 and 100 µg of morphine, between 10 and 100 µg of morphine-6β-glucuronide, and between 1 and 10 mg of reticuline.

A composition (e.g., pill or tablet) designed to deliver a low dose of morphine, designed to deliver a low dose of morphine-6β-glucuronide, designed to contain one or more morphine precursors, or designed to contain any combination thereof (e.g., both morphine and one or more morphine precursors) can be formulated to contain additional components such as L-arginine, selenium, and $Ca^{++}$. L-arginine can be included to promote a cell's ability to release nitric oxide in response to morphine via nitric oxide synthesis from L-arginine metabolism. Selenium can be added to enhance mu3 opiate receptor gene expression. Calcium sources such as calcium citrate or $CaCO_3$ can be added to help facilitate the metabolism of L-arginine into nitric oxide via a calcium-dependent constitutive nitric oxide synthase. To reduce acid reflux problems in oral applications, $CaCO_3$ can be used as a calcium source. In some cases, a pill or tablet designed to deliver a low dose of morphine can be formulated to contain 35 to 700 µg morphine (e.g., 0.1 mg morphine), 1 mg to 500 mg L-arginine (e.g., 300 mg L-arginine), 55 µg to 200 µg selenium (e.g., 100 µg selenium), and 1000 to 1300 mg $Ca^{++}$ (e.g., 1000 mg $Ca^{++}$). In some cases, a pill or tablet can be formulated to contain 1 to 10 mg reticuline (e.g., 5 mg reticuline), 1 mg to 500 mg L-arginine (e.g., 300 mg L-arginine), 55 µg to 200 µg selenium (e.g., 100 µg selenium), and 1000 to 1300 mg $Ca^{++}$ (e.g., 1000 mg $Ca^{++}$). Other components that can be included in a composition provided herein include, without limitation, pharmaceutically acceptable aqueous vehicles, pharmaceutically acceptable solid vehicles, steroids, antibacterial agents, anti-inflammatory agents, immunosuppressants, dilators, vaso-constrictors, anti-cholinergics, anti-histamines, antioxidant, and combinations thereof.

In some cases, a composition (e.g., pill or tablet) designed to deliver a low dose of morphine, designed to deliver a low dose of morphine-6β-glucuronide, designed to contain one or more morphine precursors, or designed to contain any combination thereof (e.g., both morphine and one or more morphine precursors) can be formulated to contain one or more inhibitors of morphine synthesis (e.g., a CYP2D6 or CYP2D7 inhibitor) or activity (e.g., naloxone), one or more inhibitors of dopamine synthesis or activity, or combinations thereof. Examples of CYP2D6 inhibitors include, without limitation, amiodarone, chloroquine, cimetidine, clomipramine, diphenhydramine, duloxetine, fluoxetine, hydroxychloroquin, paroxetine, propafenone, propoxyphene, and quinidine, terbinafine.

A pharmaceutically acceptable aqueous vehicle can be, for example, any liquid solution that is capable of dissolving morphine or a morphine precursor (e.g., reticuline) and is not toxic to the particular individual receiving the composition. Examples of pharmaceutically acceptable aqueous vehicles include, without limitation, saline, water, and acetic acid. Typically, pharmaceutically acceptable aqueous vehicles are sterile. A pharmaceutically acceptable solid vehicle can be formulated such that morphine or a morphine precursor is suitable for oral administration. For example, capsules or tablets can contain reticuline in enteric form. The dose supplied by each capsule or tablet can vary since an effective amount can be reached by administrating either one or multiple capsules or tablets. Any well known pharmaceutically acceptable material such as gelatin and cellulose derivatives can be used as a pharmaceutically acceptable solid vehicle. In addition, a pharmaceutically acceptable solid vehicle can be a solid carrier including, without limitation, starch, sugar, or bentonite. Further, a tablet or pill formulation of morphine or a morphine precursor can follow conventional procedures that employ solid carriers, lubricants, and the like.

Steroids can be any compound containing a hydrocyclopentanophenanthrene ring structure. Examples of steroids include, without limitation, prednisone, dexamethasone, and hydrocortisone. An antibacterial agent can be any compound that is active against bacteria, such as penicillin, erythromycin, neomycin, gentamicin, and clindamycin. An anti-inflammatory agent can be any compound that counteracts inflammation, such as ibuprofen and salicylic acid. An immunosuppressant can be any compound that suppresses or interferes with normal immune function, such as cyclosporine. A dilator can be any compound that causes the expansion of an orifice, such as albuterol. A vaso-constrictor can be any compound that constricts or narrows blood vessels, such as phenylephrine hydrochloride, cocaine, and epinephrine. An anti-cholinergic can be any compound that blocks parasympathetic nerve impulses, such as ipratropium bromide. An anti-histamine can be any compound that opposes the action of histamine or its release from cells (e.g., mast cells), such as terfenadine and astemizole.

Any method can be used to obtain morphine, morphine-6β-glucuronide, morphine precursors, or any additional component of a composition provided herein. In some cases, the components of the compositions provided herein can be obtained using common chemical extraction, isolation, or synthesis techniques. For example, reticuline can be obtained as described elsewhere (Brochmann-Hanssen and Nielsen, *Tetrahedron Lett.*, 18:1271-4 (1965) and U.S. Pat. No. 3,894,027). In some cases, the components of the compositions provided herein can be obtained from commercial vendors. For example, morphine, morphine-6β-glucuronide, codeine, norlaudanosoline, and salutaridine can be ordered from Sigma, Inc.

Any method can be used to formulate a composition provided herein. For example, common formulation mixing and preparation techniques can be used to make a composition having the components described herein. In addition, the compositions provided herein can be in any form. For example, a composition provided herein can be in the form of a solid, liquid, and/or aerosol including, without limitation, powders, crystalline substances, gels, pastes, ointments, salves, creams, solutions, suspensions, partial liquids, sprays, nebulae, mists, atomized vapors, tinctures, pills, capsules, tablets, and gelcaps. In some cases, the composition can be a dietary supplement. In some embodiments, a composition containing morphine, one or more morphine precursors, or a combination thereof can be prepared for oral administration by mixing the components with one or more of the following: a filler, a binder, a disintegrator, a lubricant, and a coloring agent. Lactose, corn starch, sucrose, glucose, sorbitol, crystalline cellulose, silicon dioxide, or the like can be used as the filler. Polyvinyl alcohol, polyvinyl ether, ethyl cellulose, methyl cellulose, acacia, tragacanth, gelatin, shellac, hydroxypropyl cellulose, hydroxypropylmethyl cellulose, calcium citrate, dextrin, or pectin can be used as the binder. Magnesium stearate, talc, polyethylene glycol, silica, or hardened plant oil can be used as the lubricant. A pharmaceutically acceptable coloring agent can be used as the coloring agent. Cocoa powder, mentha water, aromatic acid, mentha oil, borneol, or powdered cinnamon bark also can be added. In some cases, a composition containing morphine, one or more morphine precursors, or a combination thereof can be prepared for injection by mixing the components with one or more of the following: a pH adjusting agent, a buffer, a stabilizer, and a solubilizing agent.

The compositions provided herein can be administered to any mammal (e.g., rat, mouse, dog, cat, horse, cow, goat, pig, monkey, or human). In addition, any route of administration (e.g., oral or parenteral administration) can be used to administer a composition provided herein to a mammal. For example, a composition containing morphine or reticuline can be administered orally or parenterally (e.g., a subcutaneous, intramuscular, intraorbital, intracapsular, intraspinal, intrasternal, or intravenous injection).

While not being limited to any particular mode of action, the compositions provided herein can be used to increase or maintain a basal level of nitric oxide release by cells (e.g., cells expressing mu3 opiate receptors). The administration of morphine precursors such as reticuline to a mammal can lead to the conversion of the morphine precursor into morphine. The morphine produced from the morphine precursor or the morphine provided directly by a composition containing morphine or the morphine-6β-glucuronide provided directly by a composition containing morphine-6β-glucuronide can activate mu3 opiate receptors, which are coupled to nitric oxide release, and can down regulate the activated state of tissues within the mammal making them less excitable. For example, administering morphine or reticuline can limit undesired excitation and restore basal activity levels within a mammal. In addition, certain mammals may not produce enough endogenous morphine to fulfill the needs of processes normally using this material to down regulate their excitatory state (e.g., a run-away pro-inflammatory state, mental disorders, vascular disorders). Administering a morphine precursor such as reticuline can provide mammals with the morphine needed to down regulate excitatory states without administering a controlled substance. Administering morphine or morphine-6β-glucuronide directly at a low dose can provide mammals with the morphine needed to down regulate excitatory states without triggering tolerance to the administered morphine or morphine-6β-glucuronide. For example, as described herein, morphine can be administered chronically (e.g., a long duration) at a low dose without observing a reduction of morphine's effects (e.g., nitric oxide release) over time. In addition, administering morphine-6β-glucuronide can provide mammals with nitric oxide release in the periphery as opposed to the brain since morphine-6β-glucuronide exhibits a limited ability to cross the blood brain barrier.

The compositions provided herein can be administered to a mammal in any amount, at any frequency, and for any duration. Typically, a composition provided herein can be administered to a mammal in an amount, at a frequency, and for a duration effective to induce nitric oxide release in the mammal. In some cases, a composition provided herein can be administered to a mammal in an amount, at a frequency, and for a duration effective to reduce the severity of a symptom of a disease or condition (e.g., schizophrenia, mania, depression, psychosis, chronic pain, paranoia, autism, stress, Alzheimer's disease, Parkinson's disease, pro-inflammatory diseases, autoimmune disorders, histolytic medullary reticulosis, lupus, arthritis, atherosclerosis, neuronal vasculopathy, or addiction).

An effective amount of a composition provided herein or of morphine or of a morphine precursor (e.g., reticuline) can be any amount that induces cells to release nitric oxide without producing significant toxicity to the mammal. In some cases, an effective amount of a composition provided herein or of morphine or of a morphine precursor (e.g., reticuline) can be any amount that reduces, prevents, or eliminates a symptom of a disease or condition upon administration to a mammal without producing significant toxicity to the mammal. In some cases involving morphine precursors, an effective amount can be any amount that results in the production of detectable amounts of morphine within a tissue sample.

Again, a composition provided herein can be administered to a mammal in any amount. In some embodiments, the amount of a composition provided herein or of morphine or of a morphine precursor (e.g., reticuline) can be greater than 0.01 mg/kg of body weight. In some cases, the amount of a composition provided herein or of morphine or of a morphine precursor (e.g., reticuline) can be between about 0.01 and about 50 mg/kg (e.g., between about 0.01 and about 45 mg/kg; between about 0.1 and about 25 mg/kg; or between about 1 and about 5 mg/kg) of body weight. The effective amount can vary depending upon the disease to be treated (if any), the site of administration, and the mammal to be treated. Such effective amounts can be determined using the methods and materials provided herein. For example, the level of morphine production can be assessed using routine experimentation in vitro or in vivo. For example, a patient having a particular condition can receive 5 mg/kg body weight of reticuline. If the patient fails to respond or produce morphine, then the amount can be increased by, for example, ten fold. After receiving this higher concentration, the patient can be monitored for both responsiveness to the treatment and toxicity symptoms, and adjustments made accordingly.

Various factors can influence the actual amount used for a particular application. For example, the frequency of administration, duration of treatment, combination of other agents, site of administration, stage of disease (if present), and the anatomical configuration of the treated area may require an increase or decrease in the actual amount administered.

The frequency of administration of a composition provided herein can be any frequency. For example, the frequency of administration can be from about four times a day to about once a month, or more specifically, from about twice a day to about once a week. In addition, the frequency of administration can remain constant or can be variable during the duration of treatment. As with the amount administered, various factors can influence the actual frequency of administration used for a particular application. For example, the amount, duration of treatment, combination of agents, site of administration, stage of disease (if present), and the anatomical configuration of the treated area may require an increase or decrease in administration frequency. In one embodiment, a composition containing reticuline can be administered daily at a dose of about 1 to about 5 mg of reticuline per kg of body weight.

The duration of administration of a composition provided herein can be any duration. For example, a duration of administration of a composition provided herein can be longer than a week, month, three months, six months, nine months, a year, two years, or three years. In some cases, an effective duration can be any duration that reduces, prevents, or eliminates a symptom of a disease upon administration to a mammal without producing significant toxicity to the mammal. Such an effective duration can vary from several days to several weeks, months, or years. In general, an effective duration for the treatment of an acute disease can range in duration from several days to several months. Once administration of the composition is stopped, however, disease symptoms may return. In such cases, an effective duration for the prevention of certain conditions can last for as long as the individual is alive.

Multiple factors can influence the actual duration used for a particular treatment or prevention regimen. For example, an effective duration can vary with the frequency of administration, the amount administered, combination of multiple agents, site of administration, state of disease (if present), and anatomical configuration of the treated area.

If the administration of a composition provided herein (e.g., a composition containing reticuline) is toxic, the mammal can be treated with a combination of L-DOPA and dopamine to inhibit the production of morphine that results from the administered composition. For example, a combination of L-DOPA and dopamine can be used to reduce that amount of morphine produced from a composition containing a morphine precursor such that only 95, 90, 80, 70, 60, 50, 40, 30, 20, 10, or less percent of the morphine normally produced following administration of the composition is actually produced.

This document also provides methods for inducing nitric oxide release from cells. Such cells can be in vitro or in vivo. In addition, the cells can be any type of cell including, without limitation, neuronal, vascular, respiratory, immune, or digestive cells. To induce nitric oxide release from cells, the compositions provided herein can be administered as described herein. For example, a composition containing morphine can be administered to a mammal in an amount and at a frequency such that the mammal receives between 0.5 µg and 10 µg of morphine per kg of body weight per day for a duration of more than one month (e.g., more than two, three, four, five, six, seven, eight, nine, or more months).

In addition, this document provides methods for treating a mammal having a disease or condition using a composition provided herein. Examples of diseases or conditions that can be treated using the compositions provided herein include, without limitation, rheumatoid arthritis, systemic lupus erythematosus, systemic scleroderma, Behcet disease, periarteritis, ulcerative colitis, Crohn's disease, active chronic hepatitis, glomerular nephritis, autoimmune diseases, osteoarthritis, gout, atherosclerosis, psoriasis, atopic dermatitis, pulmonary diseases with granuloma, encephalitis, endotoxin shock, sepsis, inflammatory colitis, diabetes, acute myelocytic leukemia, pneumonia, heart transplantation, encephalomylitis, anorexia, acute hepatitis, chronic hepatitis, drug-induced hepatic injury, alcoholic hepatitis, viral hepatitis, jaundice, hepatic cirrhosis, hepatic insufficiency, atrial myxoma, Castleman syndrome, multiple myeloma, Rennert T lymphomatosis, mesangial nephritis, renal cell carcinoma, cytomegaloviral hepatitis, cytomegaloviral retinopathy, adenoviral cold syndrome, adenoviral pharyngoconjunctival fever, adenoviral ophthalmia, AIDS, atherosclerosis, arteriosclerosis, vasculopathy associated with diabetes, mania, depression, chronic pain, schizophrenia, psychosis, and paranoia. To treat a mammal having such a disease or condition, the compositions provided herein can be administered as described herein. For example, a composition containing morphine can be administered to a mammal in an amount and at a frequency such that the mammal receives between 0.5 µg and 10 µg of morphine per kg of body weight per day for a duration of more than one month (e.g., more than two, three, four, five, six, seven, eight, nine, or more months). In some cases, the compositions provided herein can be used to reduce the severity of a symptom of the disease or condition, or to prevent the development or onset of the disease or condition.

The invention will be further described in the following examples, which do not limit the scope of the invention described in the claims.

EXAMPLES

Example 1

Reticuline Exposure to Invertebrate Ganglia Increases Endogenous Morphine Levels The following experiments were performed to determine if exposing tissues to an opiate alkaloid precursor, reticuline, would result in increasing endogenous morphine levels.

Material and Methods

*Mytilus edulis* collected from the local waters of Long Island Sound were maintained under laboratory conditions for at least 14 days prior using in experiments. Mussels were kept in artificial seawater (Instant Ocean, Aquarium Systems, Mentor, Ohio) at a salinity of 30 PSU and at a temperature of 18° C. as previously described (Stefano et al., *Electro-Magnetobiol.*, 13:123-36 (1994)).

For reticuline exposure, 400 animals were placed and maintained in artificial seawater at 24° C., whereas control animals (100) were exposed to vehicle (PBS). For the biochemical analysis, groups of 20 animals had their pedal ganglia excised at different time periods after incubation with reticuline.

The extraction protocol, using internal or external morphine standards, was performed in a room where the animals were not maintained to avoid morphine contamination. Single use siliconized tubes were used to prevent the loss of morphine. *Mytilus edulis* pedal ganglia also were extensively washed (3 times) with PBS (0.01 M NaCl 0.132 mM, $NH_4HCO_3$ 0.132 mM; pH 7.2) prior to extraction (3 times centrifugation at 1000 rpm, 1 minute, followed by discarding the PBS) to avoid exogenous morphine contamination. Tissues were dissolved in 1N HCl and sonicated using a Fisher scientific sonic dismembrator 60 (Fisher Scientific, USA). The resulting homogenates were extracted with 5 mL chloroform/isopropanol 9:1.

After 5 minutes at room temperature, homogenates were centrifuged at 3000 rpm for 15 minutes. The three phases were separated in the following order: 1) The lowest layer corresponding to the organic phase; 2) The intermediate phase corresponding to precipitated proteins; and 3) The top aqueous supernatant phase containing morphine. The supernatant was collected and dried with a Centrivap Console (Labconco, Kansas City, Mo.). The dried extract was then dissolved in 0.05% trifluoroacetic acid (TFA) water before solid phase extraction. Samples were loaded on a Waters Sep-Pak Plus C-18 cartridge previously activated with 100% acetonitrile and washed with 0.05% TFA-water. Morphine elution was performed with a 10% acetonitrile solution (water/acetonitrile/TFA, 89.5%:10%:0.05%, v/v/v). The eluted sample was dried with a Centrivap Console and dissolved in water prior to high pressure liquid chromatography (HPLC) analysis.

The morphine radioimmuno-assay (RIA) determination was a solid phase, quantitative RIA, wherein $^{125}$I-labeled morphine competes for a fixed time with morphine in the test sample for the antibody binding site. The commercial kit employed was from Diagnostic Products Corporation (USA). Because the antibody was immobilized on the wall of a polypropylene tube, simply decanting the liquid phase to terminate the competition and to isolate the antibody-bound fraction of radiolabeled morphine was sufficient. The material was then counted in a Wallac, 3", 1480 gamma counter (Perkin Elmer, USA). Comparison of the counts to a calibration curve yielded a measure of the morphine present in the test sample, expressed as nanograms of morphine per milliliter. The calibrators contained, respectively, 0, 2.5, 10, 25, 75, and 250 nanograms of morphine per milliliter (ng/mL) in PBS. Reticuline and salutaridine did not cross-react with the antibody. The detection limit was 0.5 ng/mL.

The HPLC analyses were performed with a Waters 626 pump (Waters, Milford, Mass.) and a C-18 Unijet microbore column (BAS). A flow splitter (BAS) was used to provide the low volumetric flow-rates required for the microbore column. The split ratio was 1/9. Operating the pump at 0.5 mL/minute, yielded a microbore column flow-rate of 50 µL/minute. The injection volume was 5 mL. Morphine detection was performed with an amperometric detector LC-4C (BAS, West Lafayette, Ind.). The microbore column was coupled directly to the detector cell to minimize the dead volume. The electrochemical detection system used a glassy carbon-working electrode (3 mm) and a 0.02 Hz filter (500 mV; range 10 nA). The cell volume was reduced by a 16-nm gasket. The chromatographic system was controlled by Waters Millennium[32] Chromatography Manager V3.2 software, and the chromatograms were integrated with Chromatograph software (Waters).

Morphine was quantified in the tissues as described elsewhere (Zhu et al., *Brain Res. Mol. Brain Res.*, 88:155-60 (2001)). Briefly, the mobile phases were: Buffer A: 10 mM sodium chloride, 0.5 mM EDTA, 100 mM sodium Acetate, pH 5.0; Buffer B: 10 mM sodium chloride, 0.5 mM EDTA, 100 mM sodium Acetate, 50% acetonitrile, pH 5.0. The injection volume was 5 mL. The running conditions were: from 0 min 0% buffer B; 10 min, 5% buffer B; at 25 min 50% buffer B; at 30 min 100% buffer B. Both buffers A and B were filtered through a Waters 0.22 nm filter, and the temperature of the whole system was maintained at 25° C. Several HPLC purifications were performed between each sample to prevent residual morphine contamination remaining on the column. Furthermore, mantle tissue was run as a negative control, demonstrating a lack of contamination (Zhu et al., *Mol. Brain Res.*, 117:83-90 (2003)).

For the nitric oxide assay, ten pedal ganglia (per determination) dissected from *M. edulis* were bathed in 1 mL sterile phosphate buffered saline (PBS). Experiments used morphine at a final concentration of $10^{-6}$ M, naloxone at $10^{-6}$ M, and 1 µg of reticuline. For the opiate receptor antagonist experiments, ganglia were pretreated with naloxone for 10 minutes prior to reticuline addition. NO release was monitored with an NO-selective microprobe manufactured by World Precision Instruments (Sarasota, Fla.). The sensor was positioned approximately 100 µm above the respective tissue surface. Calibration of the electrochemical sensor was performed by use of different concentrations of a nitrosothiol donor S-nitroso-N-acetyl-DL-penicillamine (SNAP) as described elsewhere (Liu et al., *Brain Res.*, 722:125-31 (1996)). The NO detection system was calibrated daily. The probe was allowed to equilibrate for 10 minutes in the incubation medium free of tissue before being transferred to vials containing the ganglia for another 5 minutes. Manipulation and handling of the ganglia was only performed with glass instruments. Data was acquired using the Apollo-4000 free radical analyzer (World Precision Instruments, Sarasota, Fla.). The experimental values were then transferred to Sigma-Plot and -Stat (Jandel, Calif.) for graphic representation and evaluation. For binding experiments, human monocytes served as a positive control since the mu3 opiate receptor subtype, which is coupled to NO release, was identified by RT-PCR and Northern blot analysis in these cells (Cadet et al., *J. Immunol.*, 170:5118-23 (2003)). The monocytes were obtained from the Long Island Blood Center (Melville, Long Island) and processed as described elsewhere (Stefano et al., *Proc. Natl. Acad. Sci.*, 90:11099-103 (1993); Bilfinger et al., *Adv. Neuroimmunol.*, 3:277-88 (1993); and Magazine et al., *J. Immunol.* 156:4845-50 (1996)).

An additional 100 excised pedal ganglia and the human monocytes were separately washed and homogenized in 50 volumes of 0.32 M sucrose, pH 7.4, at 4° C. using a Brinkmann polytron (30 seconds, setting no. 5). The crude homogenate was centrifuged at 900×g for 10 minutes at 4° C., and the supernatant was reserved on ice. The whitish crude pellet was resuspended by homogenization (15 seconds, setting no. 5) in 30 volumes of 0.32 M sucrose/Tris-HCl buffer, pH 7.4, and centrifuged at 900×g for 10 minutes. The extraction procedure was repeated one more time, and the combined supernatants were centrifuged at 900×g for 10 minutes. The resulting supernatants (S1') were used immediately. Prior to the binding experiment, the S1' supernatant was centrifuged at 30,000×g for 15 minutes, and the pellet (P2) was washed once by centrifugation in 50 volumes of the sucrose/Tris-HCl. The P2 pellet was then re-suspended with a Dounce hand-held homogenizer (10 strokes) in 100 volumes of buffer. Binding analysis was then performed on the cell membrane suspensions.

Aliquots of membrane suspension (0.2 mL, 0.12 mg of membrane protein) were incubated in triplicate at 22° C. for 40 minutes with the appropriate radiolabeled ligand in the presence of dextrorphan (10 mM) or levorphanol (10 mM) in 10 mM Tris-HCl buffer, pH 7.4, containing 0.1% BSA and 150 mM KCl. Free ligand was separated from membrane-bound labeled ligand by filtration under reduced pressure through GF/B glass fiber filters (Whatman); filters were pre-soaked (45 minutes, 4° C.) in buffer containing 0.5% BSA. The filters were rapidly washed with 2.5 mL aliquots of the incubation buffer (4° C.), containing 2% polyethylene glycol 6000 (Baker). They were assayed by liquid scintillation spectrometry (Packard 460). Stereospecific binding was defined as binding in the presence of 10 mM dextrorphan minus binding in the presence of 10 mM levorphanol. Protein concentration was determined in membrane suspensions (prepared in the absence of BSA).

For $IC_{50}$ determination (defined as the concentration of drug which elicits half-maximal inhibition of specific $^3$H-dihydromorphine binding (for mu3), an aliquot of the respective tissue-membrane suspension was incubated with non-radioactive opioid compounds at 6 different concentrations for 10 minutes at 22° C. and then with $^3$H-dihydromorphine for 60 minutes at 4° C. as described elsewhere (Stefano et al., Proc. Natl. Acad. Sci., 90:11099-103 (1993)). The mean+/−S.E.M. for three experiments was recorded for each compound. Tyr-D-Pen-Gly-Phe-D-Pen (DPDPE) and naltrexone were obtained from Sigma Chemical Co. (St. Louis, Mo.).

Results

Figure 1:
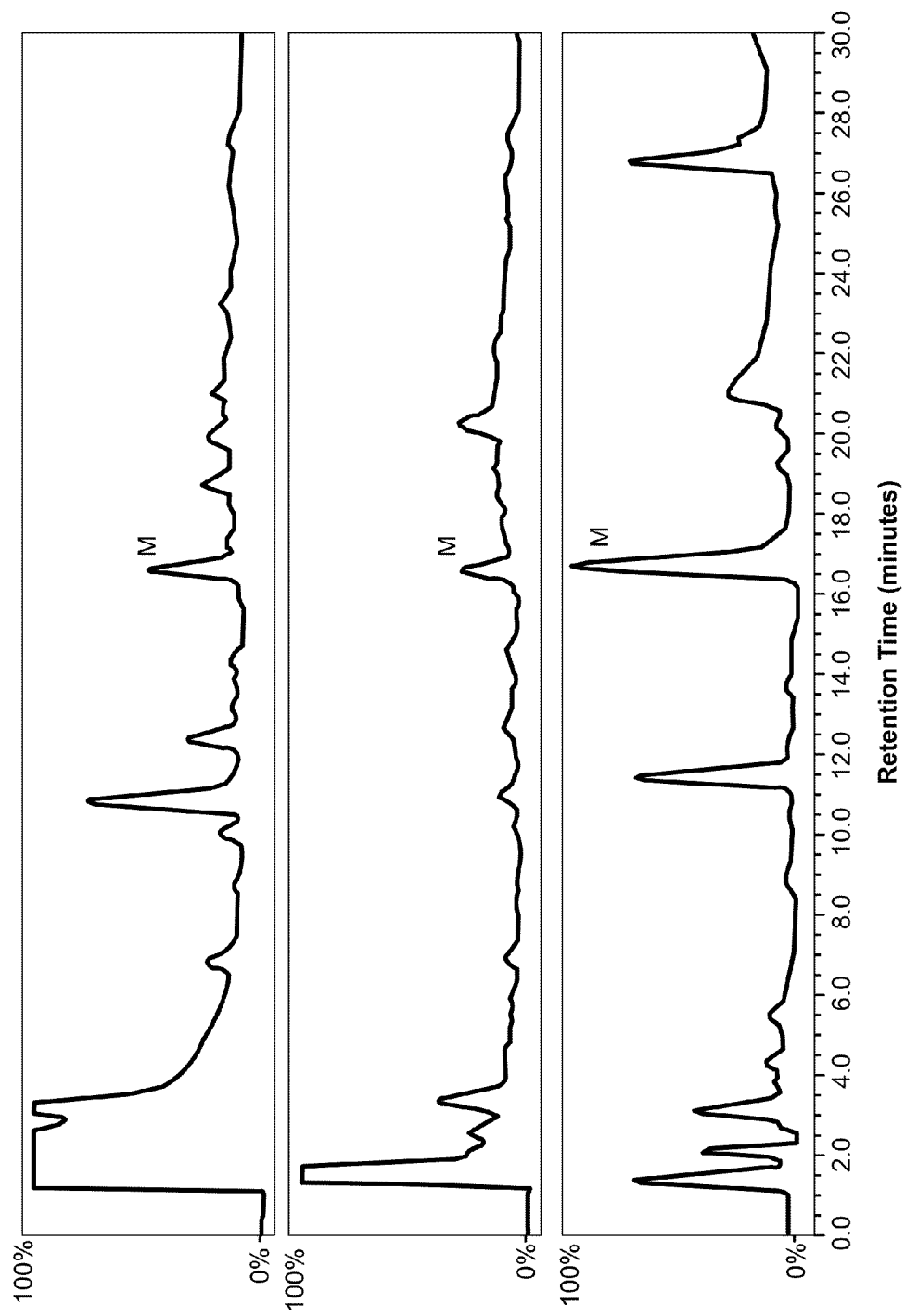
FIG. 1 is an HPLC chromatogram of ganglia extraction. The top chromatogram of ganglia incubated with 0.5 μg of reticuline for 1 hour demonstrates a level of 5 ng/mg morphine tissue wet weight. The middle chromatogram is for control ganglia. The bottom chromatogram is for a morphine standard (15 ng).

Morphine was identified in the ganglionic extraction by reverse phase HPLC using a gradient of acetonitrile following liquid and solid extraction, and was compared to an authentic standard (FIG. 1). The material exhibited the same retention time as authentic morphine. The electrochemical detection sensitivity of morphine was 80 picograms. The concentration of morphine was 1.43±0.41 ng/mg±SEM ganglionic wet weight as determined by the Chromatogram Manager 3.2 commercial software (Millemmium$^{32}$, Waters, Milford, Mass.) extrapolated from the peak-area calculated for the external standard. Ganglia incubated with 50 ng of reticuline for 1 hour exhibited a statistical increase in their endogenous morphine levels (6.7±0.7 ng/mg tissue wet weight; P<0.01; FIG. 1).

Figure 2:
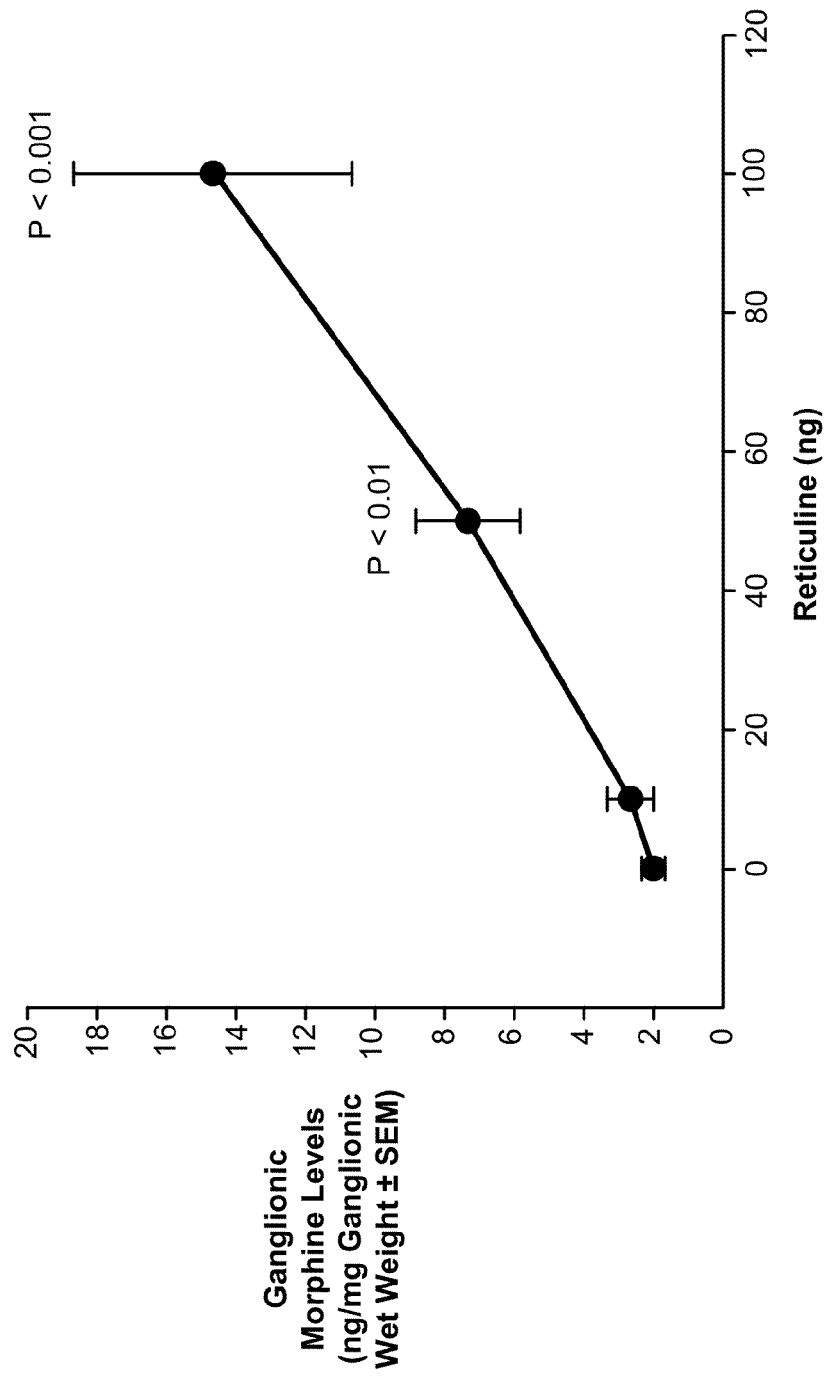
FIG. 2 is a graph plotting morphine levels for the amount of reticuline incubated with *Mytilus edulis* ganglia. Ganglia were incubated with 1.0, 10, 50, or 100 ng (per ganglion) of reticuline for 60 minutes. Morphine concentrations were obtained by RIA. One Way ANOVA analysis demonstrated that the morphine levels in ganglion incubated with reticuline were significantly higher than control at 50 and 100 ng of reticuline. One ganglion weighs about 1.7 mg.
Figure 3:
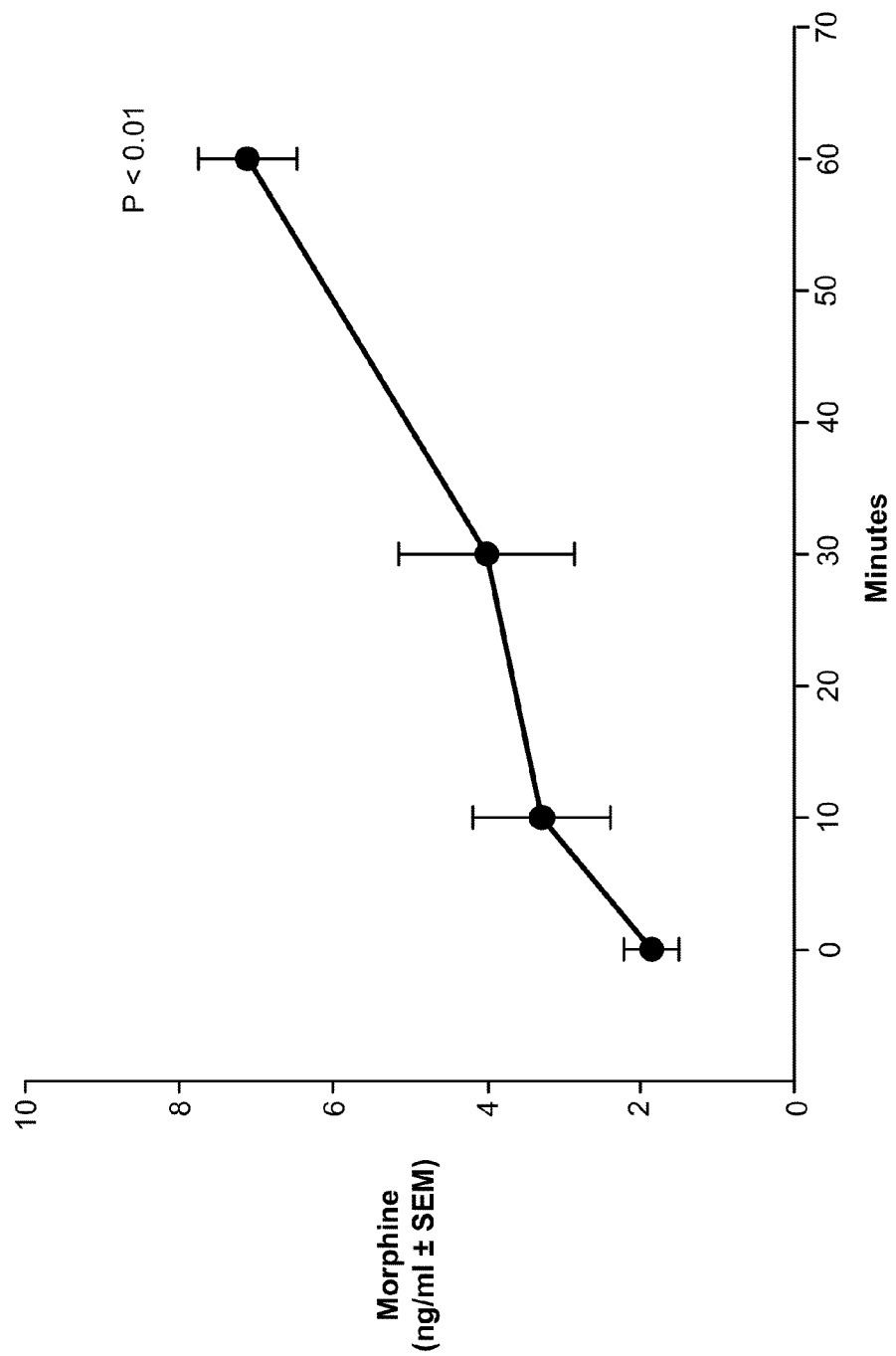
FIG. 3 is a graph plotting morphine levels versus the time *Mytilus edulis* ganglia were incubated with reticuline (50 ng/ganglion). The results of morphine concentration were obtained by RIA. One Way ANOVA analysis demonstrated that the morphine level in ganglia incubated with reticuline was significantly higher than control at 60 minutes.

The electrochemical results are compatible with the RIA quantification (FIG. 2), which yields a control ganglionic level of morphine at 1.33±0.61 ng/mg tissue wet weight±SEM. Incubation with various concentrations of reticuline increases ganglionic morphine levels after one hour in a concentration dependent manner (FIG. 2). Exposure of excised ganglia to 100 ng of reticuline yields about 14.53±4.6 ng/mg morphine (FIG. 2; P<0.001). The increase in ganglionic morphine levels occurred gradually over the 60-minute incubation period, beginning 10 minutes post reticuline addition (FIG. 3). From these studies, about 24 percent of the added reticuline was converted to morphine. Blank runs between morphine HPLC determinations did not show a morphine residue with RIA, nor did any signs of its presence occur with mantle tissue. Incubation of 50 ng of reticuline with mantle tissues did not produce detectable morphine.

Pedal ganglia, which contain mu opiate receptors, respond to morphine exposure by releasing constitutive nitric oxide synthase derived NO in a naloxone and L-NAME sensitive manner (Stefano et al., Brain Res., 763:63-8 (1997) and Cadet et al., Mol. Brain Res., 74:242-6 (1999)). In an attempt to substantiate the identity of newly synthesized morphine further, ganglia were examined for their ability to release NO in response to reticuline exposure (FIG. 4; Table 1). Reticuline ($10^{-7}$ M) did not stimulate ganglionic NO release in a manner resembling that of morphine ($10^{-6}$ M), which releases NO seconds after its application to the ganglia and lasts for 5 minutes (FIG. 4; Table 1). Instead, with reticuline, there was a three-minute delay, which was followed by an extended release period occurring over 17 minutes (FIG. 4). This reticuline-stimulated release occurred because reticuline was being converted to morphine and the newly synthesized morphine was responsible for the detected NO release, as indicated by the time course of morphine increase following reticuline exposure (FIG. 3).

TABLE 1

NO release from pedal ganglia.

| LIGAND | NO Peak Level (nM) | NO Peak Time (min) |
|---|---|---|
| Control | 0.9 ± 0.1 | None |
| Morphine ($10^{-7}$M) | 24.3 ± 3.1 | 0.8 ± 0.2 |
| Reticuline ($10^{-7}$M) | 17.6 ± 3.8 | 9.2 ± 1.5 |
| Salutaridine ($10^{-7}$M) | 18.5 ± 3.3 | 8.9 ± 1.3 |
| Dihydromorphine ($10^{-7}$M) | 23.2 ± 3.7 | 0.9 ± 0.3 |

The reticuline and salutaridine NO peak time and latency before NO production rose at 10 nM were statistically different (P<0.01) from those values recorded for morphine and dihydromorphine.

Neither reticuline nor salutaridine exhibited binding affinity for the pedal ganglia mu3 opiate receptor subtype (Table 2). This finding was further substantiated using the positive control of human monocytes from which the mu3 opiate receptor subtype was cloned. This result indicates that the pre-treatment of the ganglia with naloxone ($10^{-6}$ M) blocking the reticuline ($10^{-7}$ M) stimulated release of NO (FIG. 4) occurs by way of this precursor being converted to morphine since reticuline does not have an affinity for the mu3 opiate receptor (Table 2).

TABLE 2

Displacement of $^3$H-dihydromorphine (DHM; nmol·L$^{-1}$) by opioid ligands in various tissue membrane suspensions.

| LIGAND | Pedal Ganglia ($IC^{50}$; nM) | Monocytes ($IC^{50}$; nM) |
|---|---|---|
| δ-agonists | | |
| DPDPE | >1000 | >1000 |
| μ-agonists | | |
| Reticuline | >1000 | >1000 |
| Salutaridine | >1000 | >1000 |
| Dihydromorphine | 22 ± 2.3 | 19.1 ± 3.3 |
| Antagonists | | |
| Naltrexone | 31 ± 7.1 | 34.6 ± 8.2 |

DPDPE = (D-Pen$^2$, D-Pen$^5$)-enkephalin.

The results provided herein demonstrate that (1) morphine is present in Mytilus pedal ganglia; (2) exposing pedal ganglia to reticuline results in significant increases in ganglionic morphine levels in a concentration and time dependent manner; (3) reticuline stimulates ganglionic NO production, following a latency period, in a manner consistent with it being converted to morphine; and (4) reticuline does not exhibit an affinity for the mu3 opiate receptor, also suggesting that NO release occurs because of the conversion of reticuline into morphine.

Example 2

Mammalian Cells Produce Morphine from Reticuline

Human cells (NCI-H295R) were adapted from the NCI-H295 pluripotent adrenocortical carcinoma cell line (ATCC CRL-10296), which is from a carcinoma of the adrenal cortex. The original cells were adapted to a culture medium that decreased the population doubling time from 5 days to 2 days. While the original cells grew in suspension, the adapted cells were selected to grow in a monolayer. These cells retained the ability to produce adrenal androgens and were responsive to angiotensin II and potassium ions. To propagate these cells, the culture medium was a 1:1 mixture of Dulbecco's modified Eagle's medium and Ham's F12 medium containing 15 mM HEPES, 0.00625 mg/mL insulin, 0.00625 mg/mL transferrin, 6.25 ng/mL selenium, 1.25 mg/mL bovine serum albumin, and 0.00535 mg/mL linoleic acid, 97.5%; Nu-Serum I, 2.5%. See, e.g., Rainey et al., *Mol. Cell. Endocrinol.*, 100:45-50 (1994); Gazdar et al., *Cancer Res.*, 50:5488-5496 (1990); and Bird et al., *Endocrinology*, 133:1555-1561 (1993)).

The cells were subcultured in 6 well cell culture cluster (Corning Inc.) 24 hours before the experiment. The amount of cells was determined by Microscope (Nickon inc). Various amounts of reticuline were added to the cells, and the cells were cultured with an NAPCO incubator. The incubation was terminated after 24 hours by adding 10 NHCl. Morphine in the cells and culture medium was detected with an RIA kit purchased from Diagnostic Products Cooperation, CA, USA.

The morphine levels in the cells were significantly higher when incubated with reticuline. One half million cells incubated with 100 ng of reticuline produced about 28±5.4 ng of morphine. Control cells only produced about 9.6±3.5 ng of morphine. Culture media were negative in the test. These results demonstrate that human cells can produce morphine from reticuline.

Example 3

The Combination of L-DOPA and Dopamine Inhibits Endogenous Morphine Production

*Mytilus* pedal ganglia were obtained and incubated with 10 μg L-DOPA alone, 10 μg dopamine alone, or 10 μg L-DOPA plus 10 μg dopamine. The control ganglia were not incubated with L-DOPA or dopamine and exhibited 11.9 ng/mL morphine. The ganglia incubated with either L-DOPA alone or dopamine alone exhibited 9.31 and 8.82 ng/mL morphine, respectively. In contrast, ganglia incubated with both L-DOPA and dopamine exhibited 5.52 ng/mL of morphine. These results demonstrate that treatment with both L-DOPA and dopamine can reduce morphine production.

Example 4

L-DOPA Increase Production of Morphine

*M. edulis* collected from the local waters of Long Island Sound were maintained at a salinity of 30 PSU and at a temperature of 18° C. in marine aquaria as described elsewhere (Stefano et al., *Electro-Magnetobiol.*, 13:123-36 (1994)). For in vitro ganglionic assays, groups of 10 animals had their pedal ganglia excised and examined for their morphine levels at different time periods following the addition of L-DOPA or reticuline and at different concentrations of these morphine precursors. In vitro incubation with reticuline served as a positive control since the results provided in Example 1 demonstrate that reticuline increases endogenous ganglionic morphine levels. L-DOPA was incubated with ganglia at concentrations ranging from 1 to 100 ng/mL and at different times.

For in vivo precursor injection experiments, the animal's foot was injected with either reticuline or L-DOPA (0.1 and 1 ng/injection, respectively). Chemicals were injected by BD 1 cc syringes with 26 G needles. Each needle was inserted into that base of the foot just above the pedal ganglia.

Morphine Determination, Solid Phase Extraction

The morphine extraction protocol was performed using dissected and pooled ganglia, obtained from in vitro and in vivo experiments and run separately, as described herein.

The dried extract was then dissolved in 0.05% trifluoroacetic acid (TFA) water before solid phase extraction. Samples were loaded on a Waters Sep-Pak Plus C-18 cartridge previously activated with 100% acetonitrile and washed with 0.05% TFA-water. Morphine elution was performed with a 10% acetonitrile solution (water/acetonitrile/TFA, 89.5%:10%:0.05%, v/v/v). The eluted sample was dried with a Centrivap Console and dissolved in water prior to HPLC analysis.

Radioimmuno-Assay (RIA) Determination

The morphine RIA determination was a solid phase, quantitative RIA, wherein $^{125}$I-labeled morphine competes for a fixed time with morphine in the test sample for the antibody binding site. The commercial kit used was obtained from Diagnostic Products Corporation (USA). The detection limit was 0.5 ng/mL.

HPLC and Electrochemical Detection of Morphine in Samples

The HPLC analyses were performed with a Waters 626 pump (Waters, Milford, Mass.) and a C-18 Unijet microbore column (BAS). A flow splitter (BAS) was used to provide the low volumetric flow-rates required for the microbore column. The split ratio was 1/9. Operating the pump at 0.5 mL/min, yielded a microbore column flow-rate of 50 μL/min. The injection volume was 5 mL. Morphine detection was performed with an amperometric detector LC-4C (BAS, West Lafayette, Ind.). The microbore column was coupled directly to the detector cell to minimize the dead volume. The electrochemical detection system used a glassy carbon-working electrode (3 mm) and a 0.02 Hz filter (500 mV; range 10 nA). The cell volume was reduced by a 16-nm gasket. The chromatographic system was controlled by Waters Millennium$^{32}$ Chromatography Manager V3.2 software, and the chromatograms were integrated with Chromatograph software (Waters).

Morphine was quantified in the tissues using methods described elsewhere (Zhu et al., *Brain Res. Mol. Brain Res.*, 88:155-60 (2001)). Several HPLC purifications were performed between each sample to prevent residual morphine contamination remaining on the column. Mantle tissue was run as a negative control, demonstrating a lack of contamination. Morphine was not found in any of the solutions used in these experiments. Furthermore, animals injected with 5-hydroxytryptophan or ganglia incubated with this serotonin precursor did not exhibit any changes in their endogenous ganglionic morphine levels.

Results

Incubation of pedal ganglia in vitro with various concentrations of L-DOPA or reticuline increased ganglionic morphine levels in a time and concentration dependent manner (FIGS. 5 and 6). Control ganglia, exposed to vehicle or 5-hydroxytryptophan (1 μg/gm tissue), a serotonin precursor, exhibited 2.1±0.44 and 2.1±0.41 ng morphine per ganglion wet weight, respectively, whereas those exposed to L-DOPA exhibited 3.6±0.45 ng morphine per ganglion, representing a statistically significant increase ($P<0.05$). Exposure of excised ganglia to 100 ng of reticuline resulted in about 5.0±0.47 ng morphine per mg ganglion (FIGS. 5 and 6; $P<0.001$). The increase in ganglionic morphine levels, after L-DOPA exposure, occurs gradually over the 60 minute incubation period, beginning 10 minutes post exposure (FIG. 6). From these results, about 5% of L-DOPA appears to be converted to morphine. Blank runs between morphine HPLC determinations as well as running negative tissue controls, i.e., mantle, did not reveal a morphine residue with RIA. Analysis of the marine water and various chemicals used in the protocol also lacked morphine.

The following was performed to determine if injection of these same precursors into intact healthy animals would yield an increase in morphine levels. Injecting animals with either reticuline or L-DOPA significantly increased pedal ganglionic morphine levels after one hour (FIG. 7), demonstrating that morphine synthesis occurred. Injection of 5-hydroxytryptaphan failed to increase ganglionic morphine levels. These results demonstrate that reticuline and L-DOPA can be administered to an animal so that the animal can produce additional morphine.

The results provided herein also demonstrate that L-DOPA can be used in both morphinergic as well as dopaminergic pathways. About 5 percent of L-DOPA, which occurs early in the synthesis scheme in both pathways, appears to be used for morphine synthesis, compared to about 25 percent of reticuline, which is closer to the end product morphine and therefore more dedicated to morphine synthesis.

In addition, these results together with the results from Example 4 appear to indicate that high doses of L-DOPA can inhibit morphine production, while low doses of L-DOPA can result in increased morphine production. One possible mechanism is that high doses of L-DOPA exceeded an inhibitory threshold thereby leading to inhibition of morphine production. Low L-DOPA doses can by-pass this inhibitory threshold.

Example 5

Norlaudanosoline Increases Production of Morphine

*Mytilus edulis* collected from the local waters of Long Island Sound were maintained as described elsewhere (Stefano et al., *Electro-Magnetobiol.*, 13: 123-36 (1994)). For the biochemical analysis, groups of 20 animals had their pedal ganglia excised at different time periods and incubated with different concentrations of norlaudanosoline, ranging from 1 to 100 ng/mL.

Morphine Determination, Solid Phase Extraction

The morphine extraction protocol was performed in pooled ganglia as described herein. The dried extract was then dissolved in 0.05% trifluoroacetic acid (TFA) water before solid phase extraction. Samples were loaded on a Waters Sep-Pak Plus C-18 cartridge previously activated with 100% acetonitrile and washed with 0.05% TFA-water. Morphine elution was performed with a 10% acetonitrile solution (water/acetonitrile/TFA, 89.5%:10%:0.05%, v/v/v). The eluted sample was dried with a Centrivap Console and dissolved in water prior to HPLC analysis.

Radioimmuno-Assay (RIA) Determination

The morphine RIA determination was a solid phase, quantitative RIA, wherein $^{125}$I-labeled morphine competes for a fixed time with morphine in the test sample for the antibody binding site. The commercial kit used was obtained from Diagnostic Products Corporation (USA). The detection limit was 0.5 ng/mL.

HPLC and Electrochemical Detection of Morphine in the Sample

The HPLC analyses were performed with a Waters 626 pump (Waters, Milford, Mass.) and a C-18 Unijet microbore column (BAS). A flow splitter (BAS) was used to provide the low volumetric flow-rates required for the microbore column. The split ratio was 1/9. Operating the pump at 0.5 mL/minute, yielded a microbore column flow-rate of 50 μL/minute. The injection volume was 5 μL. Morphine detection was performed with an amperometric detector LC-4C (BAS, West Lafayette, Ind.). The microbore column was coupled directly to the detector cell to minimize the dead volume. The electrochemical detection system used a glassy carbon-working electrode (3 mm) and a 0.02 Hz filter (500 mV; range 10 nA). The cell volume was reduced by a 16-nm gasket. The chromatographic system was controlled by Waters Millennium32 Chromatography Manager V3.2 software, and the chromatograms were integrated with Chromatograph software (Waters).

Morphine was quantified in the tissues using methods described elsewhere (Zhu et al., *Brain Res. Mol. Brain Res.*, 88:155-60 (2001)). Several HPLC purifications were performed between each sample to prevent residual morphine contamination remaining on the column. Furthermore, mantle tissue was run as a negative control, demonstrating a lack of contamination.

Results

Incubation of the ganglia in vitro with various concentrations of norlaudanosoline (also called tetrahydropapoverine (THP)) increased ganglionic morphine levels after one hour in a concentration and time dependent manner (FIGS. 8 and 9; $P<0.01$). The increase in in vitro ganglionic morphine levels, after norlaudanosoline exposure, occurred gradually over the 60 minute incubation period (FIG. 9). About 20 percent of norlaudanosoline appears to be converted into morphine. Blank runs between morphine HPLC determinations as well as running negative tissue controls, i.e., mantle, did not reveal a morphine residue with RIA. Analysis of the marine water and various chemicals used in the protocol also demonstrated a lack of morphine.

Example 6

Producing Morphine in Human Cells

Human peripheral blood cells were obtained from the Long Island Blood Services (Melville, N.Y.). ACK lysis buffer (8.29 g NH$_4$Cl, 0.15 M; 1 g KHCO$_3$, 1.0 mM, 37.2 mg Na$_2$EDTA, 0.1 mM, adding 800 mL H$_2$O and adjusting the pH to 7.2-7.4 with 1 N HCl; filter sterilized through a 0.2 nm filter and stored at room temp) was used to remove any red blood cells from the buffy coat containing leukocytes. Cells were incubated for 5 minutes at room temperature in lysis buffer, and RPMI media (ATCC) used to stop the lysis reaction, followed by centrifugation for 10 minutes at 200 g. The supernatant was decanted, and the pellet washed with RPMI media. The leukocytes were resuspended in RPMI media by pipetting.

Polymorphonuclear cells (PMNs) were isolated (Ficoll-Hypaque density of 1.077-1.080 g/mL) as described elsewhere (Magazine et al., *J. Immunol.*, 156:4845 (1996); Stefano et al., *Proc. Natl. Acad. Sci. USA*, 89:9316 (1992); and Makman et al., *J. Immunol.*, 154:1323 (1995)), and the cells were examined microscopically. Greater than 95 percent of the cells were viable as determined by trypan blue exclusion.

A two-way ANOVA was used for statistical analysis after precursor exposure to the cells. Each experiment was performed 4 times. The mean value was combined with the mean value taken from 4 other replicates. The SEM represents the variation of the mean of the means. All drugs were purchased from Sigma Chemical CO. (St. Louis, Mo.), except bufuralol, which was purchased from BD Biosciences Clontech (Mountain View, Calif.).

The medium containing the PMNs was then separated after and before precursor exposure at varying concentrations for 1 hour. Cells were washed, and the endogenous morphine content was determined. The medium, devoid of cells, was also examined for the presence of morphine.

Morphine Determination

The morphine extraction protocol was performed upon washed and pelleted WBC and PMN after the incubation period as described elsewhere (Zhu et al., *Brain Res. Mol. Brain Res.*, 88:155 (2001); Zhu et al., *Eur. J. Mass Spect.*, 7:25 (2001); Zhu et al., *Neuroendocrinol. Lett.*, 23:329 (2002); Zhu et al., *Mol. Brain Res.*, 117:83 (2003); and Zhu and Stefano, *Neuro. Endocrinol. Lett.*, 25:323 (2004)). The dried extract was dissolved in 0.05% trifluoroacetic acid (TFA) water before solid phase extraction. Samples were loaded on a Waters Sep-Pak Plus C-18 cartridge previously activated with 100% acetonitrile and washed with 0.05% TFA-water. Morphine elution was performed with a 10% acetonitrile solution (water/acetonitrile/TFA, 89.5%:10%:0.05%, v/v/v). The eluted sample was dried with a Centrivap Console and dissolved in water prior to HPLC analysis.

The HPLC analyses were performed with a Waters 626 pump (Waters, Milford, Mass.) and a C-18 Unijet microbore column (BAS). A flow splitter (BAS) was used to provide the low volumetric flow-rates required for the microbore column. The split ratio was 1/9. Operating the pump at 0.5 mL/min yielded a microbore column flow-rate of 50 µL/minute. The injection volume was 5 µL. Morphine detection was performed with an amperometric detector LC-4C (BAS, West Lafayette, Ind.). The microbore column was coupled directly to the detector cell to minimize the dead volume. The electrochemical detection system used a glassy carbon-working electrode (3 mm) and a 0.02 Hz filter (500 mV; range 10 nA). The cell volume was reduced by a 16-µm gasket. The chromatographic system was controlled by Waters Millennium$^{32}$ Chromatography Manager V3.2 software, and the chromatograms were integrated with Chromatograph software (Waters).

The level of morphine in the PMN was quantified as described elsewhere (Zhu et al., *Brain Res. Mol. Brain Res.*, 88:155 (2001)). Several blank HPLC purifications were performed between each sample to prevent residual morphine contamination remaining on the column. Furthermore, mantle tissue was run as a negative control, demonstrating a lack of contamination. All solutions, media, etc. were also examined for any presence of morphine. The results of these tests revealed a lack of morphine contamination.

Radioimmuno-Assay (RIA) Determination

The morphine RIA determination was a solid phase, quantitative RIA, wherein $^{125}$I-labeled morphine competes for a fixed time with morphine in the test sample for the antibody binding site. The commercial kit used was obtained from Diagnostic Products Corporation (USA). The detection limit was 0.5 ng/mL.

CYP2D6 Molecular Demonstration

Human heparinized whole blood obtained from volunteer blood donors (Long Island Blood Services; Melville, N.Y.) was immediately separated using 1-Step Polymorphs (Accurate Chemical and Scientific Corporation, Westbury, N.Y.) gradient medium. Five mL of heparinized blood was layered over 5 mL of polymorphs in a 14 mL round-bottom tube and then centrifuged for 35 minutes at 500×g in a swinging-bucket rotor at 18° C. After centrifugation, the top band at the sample/medium interface consisting of mononuclear cells (MN) and the lower band consisting of polymorphonuclear cells (PMN) were harvested in 14 mL tubes and then washed with PBS (Invitrogen, Carlsbad, Calif.) by centrifugation for 10 minutes at 400×g.

Isolation of Total RNA

MN and PMN cells ($5 \times 10^6$) were pelleted by centrifugation, and total RNA was isolated with the RNeasy Protect Mini Kit (Qiagen, Stanford, Calif.). Pelleted cells were resuspended in buffer RLT and homogenized by passing the lysate 5 times through a 20-gauge needle fitted to a syringe. The samples were then processed following the manufacturer's instructions. In the final step, the RNA was eluted with 50 µL of RNase-free water by centrifugation for 1 minute at 10,000 rpm.

Reverse Transcription-Coupled Polymerase Chain Reaction (RT-PCR)

First-strand cDNA synthesis was performed using random primers (Invitrogen, Carlsbad, Calif.). 1 µg of total RNA was denatured at 95° C. and reverse transcribed at 40° C. for 1 hour using Superscript III Rnase H-RT (Invitrogen, Carlsbad, Calif.). Ten microliters of the RT product was added to the PCR mix containing specific primers for the CYP2D6 gene and Platinum Taq DNA polymerase (Invitrogen, Carlsbad, Calif.). The forward primer sequence was 5'-AGGTGT-GTCTCGAGGAGCCCATTTGGTA-3' (SEQ ID NO:3) and reverse primer was 5'-GCAGAAAGCCCGACTCCTCCT-TCA-3' (SEQ ID NO:4). The PCR reaction was denatured at 94° C. for 5 minutes followed by 40 cycles at 95° C. for 1 minute, 60° C. for 1 minute, and 72° C. for 1 minute, and then an extension step cycle at 72° C. for 10 minutes. PCR products were analyzed on a 2% agarose gel (SIGMA, St. Louis, Mo.) stained with ethidium bromide. The expected sizes of the PCR products were 700 bp, 300 bp, and others as described elsewhere Zhuge and Yu, *World J. Gastroenterol.*, 10:3356 (2004).

Computer-Assisted Cell Activity Analysis

PMNs, obtained as described herein, were also processed for image analysis of cell conformation as described elsewhere (Schon et al., *Adv. Neuroimmunol.*, 1:252 (1991)). The morphological measurements of PMNs were based on cell area and perimeter determinations by the use of image analysis software (Compix, Mars, Pa.). Form-factor (FF) calculations were performed as described elsewhere (Stefano et al., *Proc. Natl. Acad. Sci. USA*, 89:9316 (1992); Stefano et al., *Proc. Natl. Acad. Sci. USA*, 90:11099 (1993); and Stefano et al., *J. Neuroimmunol.*, 47:189 (1993)). The observational area used for measurement determinations and frame-grabbing was 0.4 nm in diameter. The computer-assisted image analysis system (Zeiss Axiophot fitted with Nomarski and phase contrast optics) was the same as described elsewhere (Stefano et al., *Proc. Natl. Acad. Sci. USA,* 89:9316 (1992); Stefano et al., *Proc. Natl. Acad. Sci. USA,* 90:11099 (1993); and Stefano et al., *J. Neuroimmunol.,* 47:189 (1993)).

The cells were analyzed for conformational changes indicative of either activation (amoeboid and mobile) or inhibition (round and stationary) ((Stefano et al., *Proc. Natl. Acad. Sci. USA,* 89:9316 (1992); Stefano et al., *Proc. Natl. Acad. Sci. USA,* 90:11099 (1993); and Stefano et al., *J. Neuroimmunol.,* 47:189 (1993)). The lower the FF number, the longer the perimeter and the more amoeboid the cellular shape. The proportion of activated cells was determined as described elsewhere ((Stefano et al., *Proc. Natl. Acad. Sci. USA,* 89:9316 (1992); Stefano et al., *Proc. Natl. Acad. Sci. USA,* 90:11099 (1993); and Stefano et al., *J. Neuroimmunol.,* 47:189 (1993)).

All pharmacological agents were purchased from Research Biochemicals Incorporated (Natick, Mass.) or Sigma (St. Louis, Mo.).

Results

In control (vehicle exposed) white blood cells (WBC), morphine was identified at a level of 12.33±5.64 pg/million cells±SEM (FIG. 10). These cells were extensively washed in serum-free RPMI medium, limiting any plasma morphine that may be found on the cells. It, however, is possible that the cells nonspecifically accumulated morphine from plasma. In order to determine if WBC contain morphine due to endogenous synthesis, cells were incubated with specific morphine precursors, including the amino acid tyramine Tyramine, norlaudanosoline (THP), reticuline, and L-DOPA significantly increased WBC morphine concentrations above those found in untreated cells (ANOVA test, P<0.001; FIG. 11). Morphine concentrations in cells incubated with precursors were 90.25±10.42 pg, 136.04±8.71 pg, and 136.5±12.43 pg/million cells after a one-hour treatment with THP, reticuline, and L-DOPA, respectively. Furthermore, morphine concentrations increased with exposure to precursors in a concentration-dependent manner (FIG. 11). These results demonstrate that WBC contain low but physiologically significant quantities of morphine and that exposure of these cells to morphine precursors can increase morphine synthesis.

To identify a specific population of WBC capable of synthesizing morphine, PMNs were examined. Morphine was found in these cells at a level of 11.2±4.21 pg/million cells (FIG. 12). Exposing PMNs to morphine precursors including tyramine, at levels that increased morphine production in WBC, resulted in a statistically significant increase in morphine concentrations in PMNs (FIGS. 12 and 13).

To determine if CYP2D6 is involved in morphine synthesis in PMNs, PMNs were incubated with tyramine and a CYP2D6 substrate (bufuralol). Treatment with both tyramine and bufuralol resulted in significantly diminished synthesis of morphine (P<0.001 compared to precursor augmentation levels; FIG. 12). In addition, the CYP2D6 inhibitor, quinidine, blocked morphine synthesis when PMNs were treated with tyramine, THP, or codeine, further demonstrating that CYP2D6 is involved in the synthesis of morphine (FIG. 13). Further, CYP2D6 was found to be expressed in PMNs as evidenced by RT-PCR expression analysis that resulted in an amplified 306 bp fragment corresponding to the enzyme. Sequence analysis of this fragment revealed 100 percent homology with human CYP2D6. These results demonstrate that CYP2D6 is expressed in human PMNs and that it is involved in morphine synthesis.

PMN incubation medium was evaluated to determine if morphine found in PMNs would also be found in the PMN incubation medium following exposure to morphine precursors. The levels of morphine detected in media from PMNs ($3 \times 10^6$ cells) treated with THP (100 ng), reticuline (50 ng), L-DOPA (100 ng), or L-tyrosine (100 ng) were significantly (One-way ANOVA, P<0.05) higher than the levels detected in media from untreated cells (Table 3).

TABLE 3

Morphine levels in media after the cells were removed.

| Control Medium | THP | Reticuline | L-DOPA | L-tyrosine |
|---|---|---|---|---|
| 0.726 ± 0.13 | 2.028 ± 0.42 | 2.112 ± 0.33 | 1.234 ± 0.26 | 2.223 ± 0.38 |

To examine a possible physiologic role of PMN-derived morphine, precursor-treated PMNs were incubated with other PMNs that had been exposed to different experimental protocols. After this incubation, the PMNs were evaluated for their activity level via computer-assisted image analysis. Untreated PMNs exhibited a 7.3±2.1% level of activation (FF>0.6) compared to a 43.4±5.7% level of activation for cells treated with IL-1β (2 ng/mL) after one hour. PMNs incubated with L-DOPA ($10^{-6}$ M; $10^6$ cells) exhibited a 3.7±0.4% level of activation. After washing PMNs separately and mixing the populations (L-DOPA treated and IL-1β treated) in a 1:1 ratio, the percent of activated cells decreased to 12.5±3.7% in the mixed PMN population (FIG. 14). In performing the same experiment but co-treating the IL-IP-treated cells with naloxone and then mixing them with the L-DOPA-treated PMNs, the cells exhibited a 35.2±6.3% level of activation, indicating that morphine mediated the reduced level of activation since naloxone significantly blocked morphine's action.

Taken together, these results demonstrate that normal, human white blood cells such as PMNs contain endogenous morphine, have the ability to synthesize morphine, and can release morphine into their environment. In addition, cells such as PMNs exposed to morphine precursors can release morphine into their environment, which can influence the activity state of the same cells as well as other cells not exposed to the precursors. These results also demonstrate that WBC express CYP2D6, an enzyme capable of synthesizing morphine from tyramine, norlaudanosoline, and codeine. In addition, the results provided herein demonstrate that morphine can be synthesized by another pathway, via L-DOPA, indicating that the dopamine and morphine biosynthesis pathways are coupled (FIG. 15). Taken together, the results provided herein demonstrate that morphine can be made from two starting points, and that inhibiting either pathway separately results in continued morphine synthesis apparently because the other pathway can compensate for the inhibition.

Example 7

Tyrosine and Tyramine Increase Morphine and Dopamine Levels In Vitro and In Vivo

*Mytilus edulis* collected from the local waters of Long Island Sound were maintained as described herein. For the biochemical in vitro analysis of either dopamine (DA) or morphine, groups of 20 animals had their pedal ganglia excised on ice at different time periods and incubated with different concentrations of tyrosine or tyramine, ranging from 1 to 100 ng/mL. Ganglia were maintained in a 50:50 mixture of boiled cell-free artificial sea water and Instant Ocean (Boston, Mass.). The pedal ganglia were incubated with and without tyrosine or tyramine in the presence of quinidine, a CYP2D6 inhibitor, and alpha methyl para tyrosine (AMPT), which inhibits tyrosine hydroxylase.

For in vivo treatments, the animal's foot (20 animals per treatment) was injected with tyrosine ($10^{-5}$ M), tyramine ($10^{-5}$ M), or saline. Other animals were exposed to the enzyme inhibitors AMPT or quinidine alone or immediately following the respective foot injection. After a 1-hour incubation in seawater at room temperature, ganglionic morphine levels were determined via the HPLC and RIA methods described herein. All chemicals were purchased from Sigma (St. Louis, Mo.).

Extraction and HPLC UV Detection of DA

Dopamine was extracted from both ganglia (20 pedal ganglia per treatment; replicated 4 times) and hemolymph (10 mL per treatment; replicated 4 times). After ganglionic dissection, ganglia were pooled into one eppendorf tube, 1 ml of 1 N HCl was added, and the tissue was sonicated by sonic dismemberator (Fisher scientific, USA). Homogenized tissue was then transferred to a 15 mL polypropylene centrifuge tube (Fisher Scientific, PA, USA). 5 mL of chloroform/isopropanol (9:1, v/v) was added, and the contents of the tube vigorously vortexed for 5 minutes at room temperature. Tubes were centrifuged at 4000 rpm for 15 minutes at 4° C. Supernatant (water soluble layer) was dispatched into pre-siliconized 1.5 tubes (Midwest Scientific) and kept at 4° C. for immediate use for HPLC determination or stored at $-80$° C. for further analysis.

HPLC was performed with waters 626 pump and 2487 dual 2, absorbance detector. A Xterra RP18 column with 5 n size particle was used to purify dopamine Isocratic mobile phase was applied with one buffer (1 mM $CH_3COONH_4$, 98% distilled water and 2% HPLC grade of acetonitrile (Fisher Scientific). Follow rate was set at 0.5 mL/minute. A concentration curve was obtained by running different contractions of dopamine. The detection limit was 0.5 µg/mL.

CYP2D6 Molecular Demonstration and Isolation of Total RNA

Pedal ganglia (100) were immediately processed after dissection. The ganglia were placed in 1.5 mL tubes and then washed with PBS (Invitrogen, Carlsbad, Calif.). Total RNA was isolated using the RNeasy mini kit (Qiagen, Valencia, Calif.). Ganglia were homogenized in 600 µL buffer RLT. The samples were processed following the manufacturer's instructions. In the final step, the RNA was eluted with 50 µL of RNase-free water by centrifugation for 1 minute at 10,000 rpm.

Reverse Transcription-Coupled Polymerase Chain Reaction (RT-PCR)

First-strand cDNA synthesis was performed using random primers (Invitrogen, Carlsbad, Calif.). 1 µg of total RNA was denatured at 95° C. and reverse transcribed at 40° C. for 1 hour using Superscript III Rnase H-RT (Invitrogen, Carlsbad, Calif.). Ten microliters of the RT product was added to the PCR mix containing primers for CYP2D6 and CYP2D7 genes and Platinum Taq DNA polymerase (Invitrogen, Carlsbad, Calif.). The forward primer sequence was 5'-GGC-CAAGGGGAACCCTGAGA-3' (SEQ ID NO:5) and reverse primer was 5'-GGTCATACCCAGGGGGACGA-3' (SEQ ID NO:6). The PCR reaction was denatured at 95° C. for 5 minutes followed by 40 cycles at 95° C. for 30 seconds, 60° C. for 30 seconds, and 72° C. for 1 minute, and then an extension step cycle at 72° C. for 10 minutes. PCR products were analyzed on a 2% agarose gel (Sigma, St. Louis, Mo.) stained with ethidium bromide. The expected sizes of the PCR products were 282 bp for CYP2D6 and 340 bp for CYP2D7.

DNA Sequencing

After excising the PCR product from the gel, DNA purification was performed with the Qiaquick gel extraction kit (Qiagen). The PCR product was dissolved in 35 µL $H_2O$ and sent to Lark Technologies, Inc. (Houston, Tex.) for direct sequencing.

Results

Figure 16:
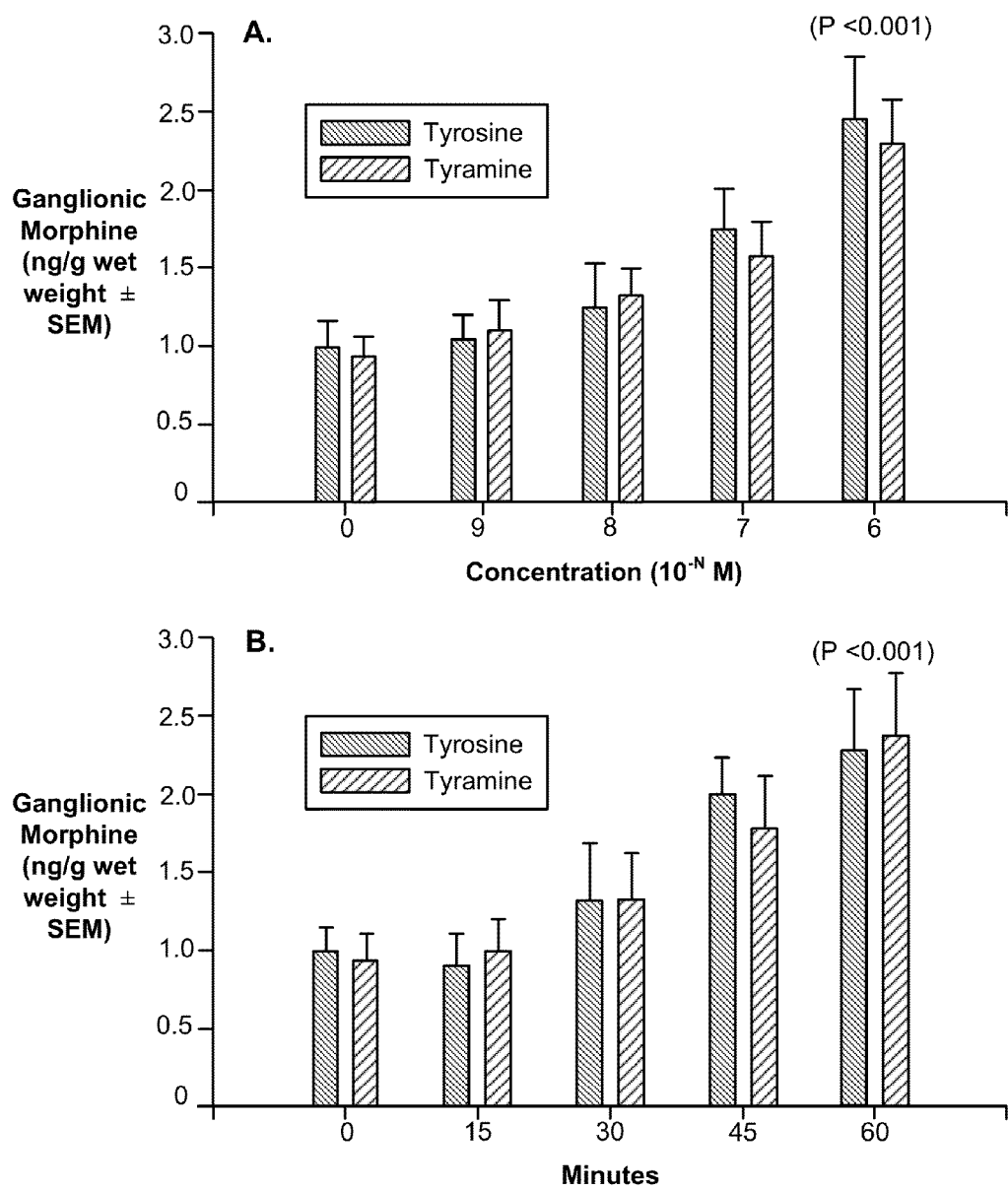

Mytilus pedal ganglia were incubated in vitro with tyrosine or tyramine, both of which resulted in an increase in ganglionic morphine levels in a concentration and time dependent manner (FIG. 16; $P<0.001$, from $1.08\pm0.27$ ng/g ganglionic wet weight to $2.51\pm0.36$ ng/g for tyramine and from $0.96\pm0.31$ ng/g to $2.39\pm0.64$ ng/g for tyrosine). The increase in ganglionic morphine levels, after tyrosine and tyramine exposure, occurred gradually over the 60 minute incubation period (FIG. 16B). About 7 percent of tyrosine or tyramine appears to be converted to morphine under these in vitro conditions. Blank runs between morphine HPLC determinations as well as running negative tissue controls, e.g., mantle, did not reveal a morphine residue with HPLC coupled RIA. Analysis of the marine water and various chemicals used in the protocol also demonstrated a lack of morphine.

Ganglia treated with quinidine and tyramine exhibited less tyramine-induced morphine production than the levels observed with ganglia treated with tyramine only (FIG. 17). This inhibition of morphine production was quinidine concentration dependent (FIG. 17). Likewise, ganglia treated with AMPT and tyrosine exhibited less tyrosine-induced morphine production than the levels observed with ganglia treated with tyrosine only (FIG. 18). This inhibition of morphine production was AMPT concentration dependent (FIG. 18). Exposure to either enzyme inhibitor alone did not significantly reduce morphine levels below the level of non-exposed ganglia (FIGS. 17 and 18). Exposure of pedal ganglia to both enzyme inhibitors, however, reduced ganglionic morphine levels significantly ($0.23\pm0.16$ ng/g wet weight$\pm$SEM; $P<0.01$) below that of controls (0.99 and 0.92 ng/g wet weight, respectively), indicating that both pathways were working simultaneously, compensating for the other's inhibition.

Figure 20:
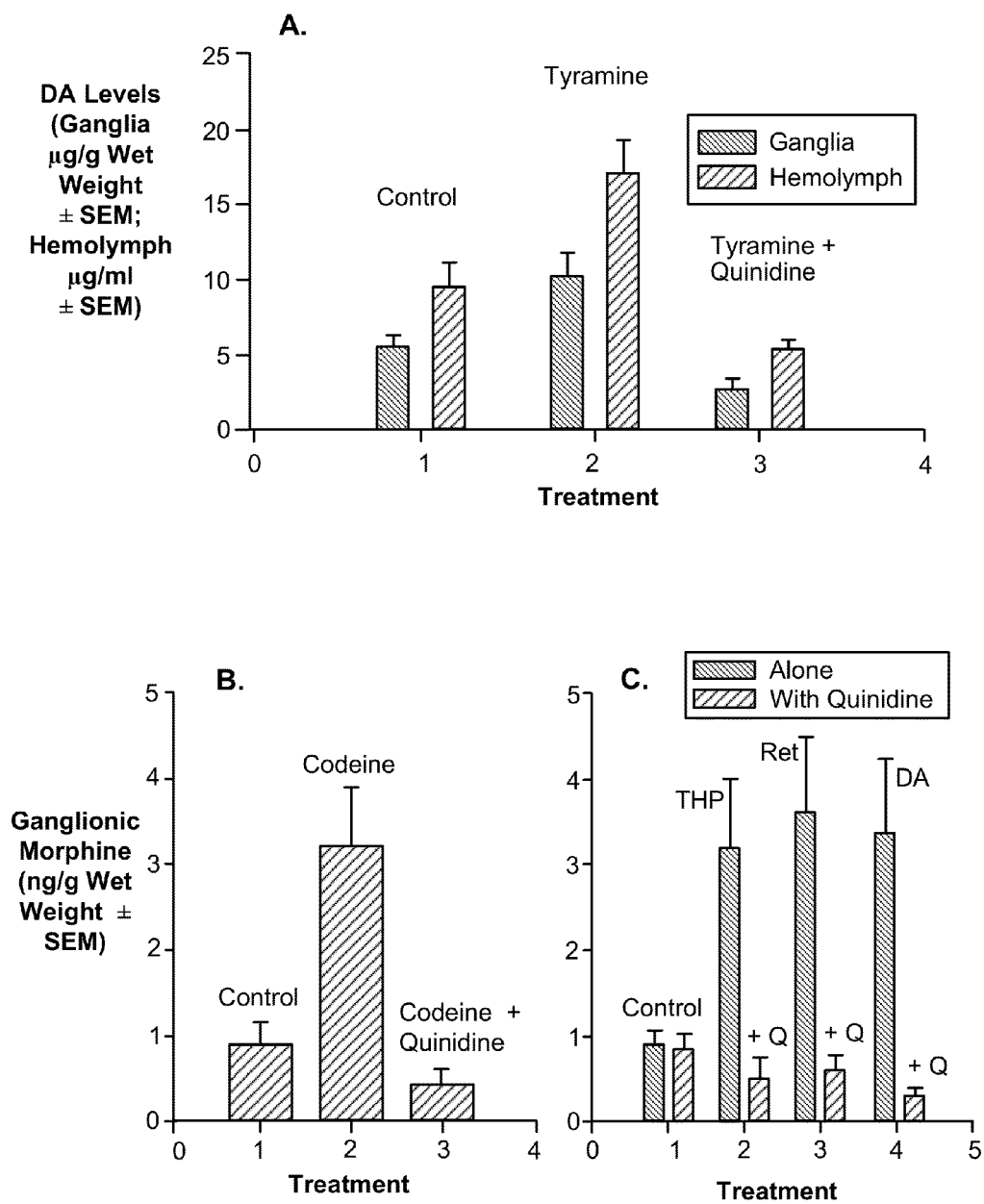

To examine the tyramine to dopamine step, dopamine (DA) levels in ganglia and hemolymph were examined before and after tyramine addition followed by CYP2D6 inhibition by quinidine. Tyramine injection significantly increased ganglionic ($4.98\pm0.27$ µg/g to $9.17\pm1.21$ µg/g wet weight; $P<0.01$) and hemolymph ($10.13\pm1.24$ µg/mL to $16.47\pm1.28$ µg/mL, $P<0.05$) DA levels (FIGS. 19 and 20). The ganglionic and hemolymph DA level increases were blocked by quinidine exposure, demonstrating that the CYP2D6 enzyme was mediating this step. Ganglia were also exposed to THP, reticuline, DA, or codeine. Each resulted in significantly enhanced morphine levels, a phenomenon that was also significantly blocked by quinidine exposure, again demonstrating a role for CYP2D6 in the second part of the morphine biosynthetic pathway (FIGS. 15 and 20).

A molecular analysis was performed to confirm the pharmacological evidence for the involvement of CYP2D6 in ganglia. Briefly, RT-PCR was used to amplify a 282 bp fragment from Mytilus tissue. The sequence of this fragment was found to be about 94 percent similar to the human cytochrome P450, family 2, subfamily D, polypeptide 6 mRNA sequence set forth in GenBank accession number M20403 (FIG. 21).

In in vivo experiments, animals were injected with either tyrosine ($10^{-5}$ M) or tyramine ($10^{-5}$ M) in their foot. One hour after injection, ganglia were dissected and extracted for morphine analysis. Both precursors significantly enhanced ganglionic morphine levels compared with control values (2.46±0.22 ng/g wet weight for tyrosine and 3.28±0.45 ng/g for tyramine compared to controls 1.02±0.24 ng/g; $P<0.001$; FIG. 22). Statistical significance was not be achieved at the $10^{-7}$ to $10^{-6}$ M concentrations, but was achieved at the $10^{-5}$ M concentration (FIG. 22). Additionally, 20 animals per drug protocol were injected via the foot with either AMPT ($10^{-4}$ M) or quinidine ($10^{-4}$ M). These animals did not exhibit any change in morphine levels even when both AMPT and quinidine were co-administered. This indicates that basal morphine levels were being maintained via morphine storage, or the inhibitors did not reach the ganglia. Compared to controls injected with saline, the tyrosine and tyramine animals exhibited a significant decrease in ganglionic morphine levels when the respective enzyme inhibitors were topically applied to the pedal ganglia of intact animals after they were injected with the respective amino acids in the foot (decrease of 30 and 25 percent, respectively; $P<0.01$; FIG. 22). In this regard, it was estimated that only 1-2 percent of the injected amino acids were directed to morphine biosynthesis.

Taken together, these results demonstrate that tyrosine and tyramine are, in part, being converted to dopamine then morphine, and that this process can be inhibited by altering either or both CYP2D6 or tyrosine hydroxylase. This process appears to be dynamic in that the inhibition of one pathway allows the other to continue with morphine synthesis. Moreover, dopamine and morphine synthesis appear to be coupled (FIG. 15). In particular, these results demonstrate that morphine biosynthesis can occur by way of tyrosine and/or tyramine, making it very likely that morphine synthesis occurs regardless of circumstances. As demonstrated, neither AMPT or quinidine when administered alone reduced endogenous morphine levels below that of controls suggesting the presence of a storage pool of morphine. Co-administration of AMPT and quinidine reduced endogenous morphine levels below that of controls. These results indicate that if one pathway is blocked, the overall pathway continued because the other complementary pathway to dopamine remains functional. This coupling to dopaminergic processes can have biomedical implications. For example, the DA component can modulate excitatory states, including rage, whereas the morphinergic component can result in a calming action associated with relaxation and reward. This association can explain the calming effect that follows excitatory emotional states.

Example 8

Use of Low Dose Morphine

The following experiments were performed to evaluate the ability of low doses of morphine to exert biological effects. Whole *Mytilus* animals were treated with saline or morphine ($10^{-6}$ to $10^{-10}$ M) by injection. After a five minute incubation, hemolymph was collected and incubated with LPS (1 µg/mL). Cells from animals pre-treated with morphine from $10^{-7}$ to $10^{-10}$ M did not exhibit a reduction in the level of cell activation that was observed with LPS-treated cells obtained from saline-treated animals (FIG. 23). Cells from animals pre-treated with morphine ($10^{-6}$ M) exhibited 19.3±3.8 percent activation. Thus, lower doses of morphine did little to alter the LPS stimulatory action on immunocytes when administered in an almost concomitant manner.

Whole *Mytilus* animals were treated daily with saline or morphine ($10^{-6}$ to $10^{-10}$ M) by injection for 4 days. After a five minute incubation, hemolymph was collected and incubated with LPS (1 µg/mL). Cells from animals pre-treated with morphine from $10^{-7}$ to $10^{-9}$ M exhibited a reduction in the level of cell activation that was observed with LPS-treated cells obtained from saline-treated animals (FIG. 24). Cells from animals pre-treated with morphine ($10^{-10}$ M) did not exhibit a reduction in the level of cell activation. Thus, lower doses of morphine (e.g., $10^{-7}$ to $10^{-9}$ M) can limit excitatory activations and possibly reduce pre-existing activation when given over time.

100 healthy *Mytilus* animals were treated with 10 U/mL of TNF-α by injection. After 4 days, about 20 percent of the TNF-treated animals died (FIG. 25). Pre-treatment for four days with daily injections of morphine at a low dose ($10^{-7}$ M) reduced the number of animals that died (FIG. 25). These results demonstrate that repeated administration of low doses of morphine can protect against TNF-α-induced death by apparently reducing the level of TNF-α-induced inflammation within the animals.

In another experiment, COS-1 cells were transfected with nucleic acid that directs expression of a human mu3 opiate receptor. The stably transfected cells were then incubated with morphine, and the amount of nitric oxide (NO) released from the cells was measured amperometrically. Cells treated with $10^{-7}$ M and $10^{-8}$ M of morphine released 9±2 nM and 18±3 nM of NO, respectively, within 2 minutes of morphine addition. These results demonstrate that the mu3 opiate receptor mediates morphine coupled no release.

In another experiment, human saphenous veins were treated with morphine and assessed for NO release. Tissue treated with $2\times10^{-7}$ M morphine released 7±2 nM of NO. When pre-treated with $10^{-6}$ M of CTOP, an opiate receptor inhibitor specific for mu receptors, 10 minutes before adding morphine, no NO release was detected. These results demonstrate that the NO release was mediated via an opiate receptor.

*Mytilus* animals were divided into three groups. The first group was a control group with each animal being untreated prior to receiving a single injection of saline. The second and third groups of animals received daily injections of 1 µM and 0.01 µM of morphine, respectively, via the foot. Two hours post-injection, pedal ganglia were obtained from the animals and assessed for mu3 opiate receptor binding densities. This experiment was repeated 5 times, each with a separate set of *Mytilus* animals.

Treatment with 1 µM of morphine resulted in reduced mu3 opiate receptor binding, while treatment with 0.01 µM of morphine did not (FIG. 27). These results demonstrate that low dose morphine is effective without altering binding site densities.

45 *Mytilus* animals were divided into three groups. The first group was a control group with each animal receiving a mock injection of saline. The second and third groups of animals received daily injections of 1 µM and 0.01 µM of morphine, respectively, via the foot for up to four days. Two hours post-injection, NO release was measured. This experiment was repeated 5 times, each with a separate set of *Mytilus* animals.

Animals receiving 1 µM morphine exhibited NO release on day one (FIG. 28). The level of NO release for animals receiving 1 µM morphine for four days, however, was substantially lower than the level of NO release observed after one day of treatment with 1 µM morphine. When challenged with 10 µM morphine, animals receiving 1 µM morphine for four days exhibited about half the amount of NO release observed with animals receiving 1 µM morphine for one day. These results demonstrate that animals receiving repeated administrations of 1 µM morphine develop tolerance to morphine. Animals receiving 0.01 µM morphine exhibited NO release on day one at a level similar to that which was also observed after days two, three, and four (FIG. 28). These results demonstrate that animals receiving repeated administrations of 0.01 µM morphine continue to respond to morphine administration without developing detectable or significant tolerance to morphine.

In another experiment, human SH-SY5Y cells were cultured in 96 well plates (250,000 cells per well). The cells were continuously exposed to $10^{-8}$ M or $10^{-6}$ M of morphine sulfate. At various time points (initial and 1, 2, and 7 days), the cells were washed in phosphate buffered saline (PBS), placed in 250 µL PBS, and assessed for NO release. NO release was measured using an Apollo-4000 free radical analyzer with a 30 nm probe. The probe was calibrated daily with SNAP. Each assay was performed in quadruplicate. The mean±the standard error were graphed for each time point. Control cells remained untreated until being challenged with $10^{-6}$ M morphine.

Cells treated with a high morphine dose of $10^{-6}$ M lost their initial levels of NO release, while cells treated with a low morphine dose of $10^{-8}$ M remained capable of releasing NO in response to morphine (FIGS. 29 and 30). Cells treated daily with $10^{-6}$ M morphine for six days and given $10^{-6}$ M of morphine on the seventh day exhibited 3.4 nM of NO release. These results demonstrate that tolerance occurs only at the high dose.

Example 9

Morphine-6β-Glucuronide Increases mu3 Opiate Receptor Expression Levels

Human blood cells (mononuclear cells and polymorphonuclear cells) were incubated with $10^{-7}$M morphine-6β-glucuronide (M6G) for 30 minutes and assessed from the relative gene expression level of mu3 opiate receptor sequences using real time RT-PCR (Applied Biosystems 5700 SDS). In addition, the cells were either incubated with or without $10^{-6}$M CTOP 10 minutes prior to adding M6G.

Both mononuclear cells and polymorphonuclear cells exhibited an increase in mu3 opiate receptor expression when treated with M6G (FIG. 31). In both cases, the increase in mu3 opiate receptor expression levels was blocked by CTOP pre-treatment (FIG. 31). These results demonstrate that the increase in mu3 opiate receptor expression levels is mediated by M6G.

Example 10

Morphine Modulates β-Amyloid Metabolism Via Nitric Oxide Providing a Protective Mechanism for Morphine in Alzheimer's Disease The deposition of intracellular and extracellular β-amyloid peptide (Aβ) in the brain is a pathologic feature of Alzheimer's disease (AD), a prevalent neurodegenerative disorder. The following experiments were performed to better understand the role of Aβ in causing AD's symptoms.
Methods and Materials
SH-SY5Y human neuroblastoma cells (ATCC, USA) were cultured in Dulbecco's modified Eagle's medium/Ham's nutrient mixture (DMEM-F12) (Invitrogen, USA), and HTB-11 human neuroblastoma cells (ATCC, USA) were cultured in Minimum Essential Medium Alpha Medium (MEM-α) (Invitrogen, USA). Cells were kept in a 37° C. incubator (Napco) gassed with 5% $CO_2$/95% air. All treatments were performed under a sterile hood.

Reverse transcriptase-polymerase chain reaction (RT-PCR) was performed to analyze the effects of $A\beta_{1-42}$, morphine, and SNAP treatments upon BACE-1 and BACE-2 mRNA expression in SH-SY5Y and HTB-11 cells. After the treatment time-period, cells were harvested, and total RNA was extracted using RNeasy RNA Isolation kit (Qiagen) following the manufacturer's procedures. Total RNA yield was determined using a Spectrophotometer RNA/DNA calculator (Pharmacia Biotech). Total RNA concentration was then standardized for semi-quantitative RT-PCR, which was carried out in a Geneamp Thermocycler PCR System 9700 (P.E. Applied Biosystems). Primers used for PCR were as follows: Forward 5'-TGACTGGGAACACCCCATAACT-3' (SEQ ID NO:7) and reverse 5'-CGAGCGCCTCAGTGTTACTCT-3' (SEQ ID NO:8) for BACE-1, and forward 5'-AGCCATC-CTCCTTGTCTTAATCG-3' (SEQ ID NO:9) and reverse 5'-TCTGGCGGAAAATAACCTCAA-3' (SEQ ID NO:10) for BACE-2. The expected product length was 556 bp for both primer sets. PCR products and a 100 bp DNA marker were then loaded in a 2% agarose gel stained with ethidium bromide. Gel electrophoresis was performed using a power-supply (E-C Apparatus Corp.) set at 110V with constant amperage for 1.5 hours. Gels were then photographed using a Gel Documentation System (UVP), and bands analyzed using Gel-Pro Analyzer (MediaCybernetics) on a P4 Windows machine. Expression levels were standardized to a reference gene, cyclophilin, using the following primers: forward 5'-TTTCGTGCTCTG-AGCACTGG-3' (SEQ ID NO:11) and reverse 5'-CTTGCCATTCCTGGACCCAA-3' (SEQ ID NO:12).

The production of NO in SH-SY5Y cells was detected using the Apollo 4000 Free Radical Analyzer (World Precision Instruments). SH-SY5Y cells were trypsinized and cultured in a 6-well plate for 48 hours. An L-shaped amperometric NO-specific probe was connected to the Apollo Analyzer and calibrated using a SNAP+$CuCl_2$ solution, which releases calculable amounts of NO. Cells were pretreated with 10 and 25 µM Aβ for 30 minutes and 24 hours. At the end of the treatment time-point, the media was removed and replaced with PBS warmed in a 37° C. bath, which is non-reactive with the probe. The probe was inserted about 1.5 mm above the cells and allowed to equilibrate for 5 minutes. Then, morphine-6β-gluconuride (M6G) was added to each plate at a concentration of 1 µM. M6G attaches to G-protein-coupled mu3 receptors on SH-SY5Y cells, stimulating release of $Ca^{+2}$ ions which activate cNOS (Cadet et al., *Frontiers in Bioscience*, 9:3176-86 (2004)), thereby normally releasing constitutive NO from neuroblastoma cells within minutes. The probe was monitored in real-time for the production of NO "spikes." NO data was recorded using Free Radical Analyzer (World Precision Instruments). Cells were then discarded.

$A\beta_{1-42}$, nitro-L-arginine methyl ester (L-NAME), ethidium bromide, and trypsin-EDTA were purchased from Sigma-Aldrich, USA. 0.1 M dithiothreitol (DTT), 10× Polymerase Chain Reaction (PCR) buffer, Superscript reverse-transcription enzyme, TAQ polymerase, 50 µM $MgCl_2$, 5× First Strand Buffer, the custom PCR primers, and random primers were purchased from Invitrogen, USA, and stored at −20° C. Phosphate-buffered saline was also purchased from Invitrogen, USA, and stored at room temperature. Nucleotides (dNTPs) were purchased from Amershar Pharmacia Biotech, USA, and stored at 25 µM concentration at −20° C. RNeasy RNA Isolation reagents and columns were purchased from Qiagen, USA. A stock solution of the $A\beta_{1-42}$ peptide was prepared at 1 mM concentration and kept frozen at −20° C. Electrophoresis-grade agarose was purchased from Fisher Biotech, USA, and stored at room temperature. S-Nitroso-N- acetyl-D, L-penicillamine (SNAP) used for both cell treatment and NO detector calibration was purchased from World Precision Instruments, USA.

Results

Untreated HTB-11 cells constitutively express BACE-1 and BACE-2 mRNA. Morphine exposure to these cells down regulates the expression of BACE-1 after 24 hours in a concentration dependent manner (1 μM dosage having a greater effect than 5 μM, 44% as compared to 18%; FIG. 32). Simultaneously, morphine up regulates the expression of BACE-2 expression in HTB-11 cells, an effect enhanced in the presence of $A\beta_{1-42}$ (FIG. 33). Since BACE-1 promotes production of $A\beta_{1-42}$ and BACE-2 inhibits it, morphine can be neuroprotective since morphine modulation of the BACE enzymes would decrease $A\beta_{1-42}$ production. Morphine's effects on both BACE-1 and BACE-2 expression were blocked by naloxone (FIG. 34), verifying that the neuroprotective action of morphine is directly related to its binding to the mu3 opiate receptor.

One of endogenous morphine's primary physiological effects is cNOS derived NO release via mu3 opiate receptor subtype coupling. To determine whether morphine's neuroprotective effects on the Aβ pathway were NO dependent, HTB-11 cells were treated with L-NAME, a cNOS inhibitor. L-NAME significantly blocked the effects of morphine (FIG. 35), indicating that NO release is involved in morphine's neuroprotective moderation of BACE-1 and -2. HTB-11 cells were exposed to SNAP, a NO donor, and then analyzed for BACE expression levels. After 4- and 24-hour exposures, cells treated with SNAP exhibited reduced BACE-1 expression in a concentration dependent manner similar to that observed with morphine, which also was enhanced in the presence of $A\beta_{1-42}$ (FIGS. 36 and 37). SNAP also up regulated in a concentration dependent manner BACE-2 expression at both the 4- and 24-hour timepoints (FIGS. 38 and 39), as did morphine. In the presence of $A\beta_{1-42}$, SNAP dose-dependently increased BACE-2 expression (FIGS. 38 and 39).

To verify the semi-quantitative accuracy of the RT-PCR procedures and to explore whether the effects of SNAP on BACE expression occur earlier than four hours, gene expression of BACE-1 and BACE-2 was analyzed in an additional mRNA expression experiment for two hours (FIG. 40). BACE-1 and BACE-2 expression levels were altered in cells treated with SNAP for two hours with BACE-1 expression being down-regulated and with BACE-2 expression being up-regulated. The expression of the reference gene β-actin was not affected.

SH-SY5Y neuroblastoma cells normally release NO via cNOS in response to application of either morphine or its metabolite, M6G. To determine whether $A\beta_{1-42}$ disrupts this process, SH-SY5Y cells were pre-treated with varying concentrations of $A\beta_{1-42}$ for 1 hour. Following the addition of M6G, the $A\beta_{1-42}$-treated cells exhibited a dose-dependent decrease in NO release, demonstrating that $A\beta_{1-42}$ is dose-dependently inhibiting the release of constitutive NO (FIG. 41). Pretreatment with L-NAME ($10^{-4}$ M), a cNOS inhibitor, for 4 minutes also prevented M6G-induced release of NO, verifying that M6G was inducing release of NO through cNOS given the rapid time course of the coupling (FIG. 41; panel G). The reduction of M6G-induced NO release after $A\beta_{1-42}$ treatment suggests that $A\beta_{1-42}$ is either (a) directly inhibiting the activation of cNOS or (b) interfering with the binding of M6G to the mu3 opiate receptor, both of which would potentially impact the level of basal NO in the AD-afflicted human brain. Furthermore, SH-SY5Y cells release NO at a low level compared to human immune and vascular tissues (3-4 nM compared to 26-29 nM when treated with morphine at $10^{-6}$ M).

These results demonstrate that morphine, in a concentration and time dependent manner, up regulates BACE-2 expression while simultaneously down regulating BACE-1 expression. This phenomenon can be blocked by treating the cells with the opiate receptor antagonist, naloxone. This morphine-mediated process is coupled to cNOS-derived NO release, which was ascertained by treating the tissue with the NOS inhibitor L-NAME. NO alone can mediate this effect, further substantiating this observation. Additionally, in the presence of $A\beta_{1-42}$, both the morphine and NO effects are enhanced. $A\beta_{1-42}$ alone appears to have the ability to inhibit cNOS-derived NO release at higher concentrations. A two-way relationship between $A\beta_{1-42}$ and morphine/NO appears to exist. Morphine/NO modifies the expression of two polypeptides involved in the production of Aβ, down regulating BACE-1 expression and up regulating BACE-2 expression. In addition, after long-term incubation, $A\beta_{1-42}$ appears to enhance the ability of NO to modify BACE expression. Taken together, morphine, via its coupling to NO, appears to be neuroprotective since it promotes BACE-2 up regulation, which enhances Aβ catabolism, avoiding the effect of Aβ inhibiting NO production.

The results provided herein can support the following pathway regarding the origin of AD (FIG. 42). Assuming a deficiency of endogenous morphine or other cNOS activators/scavengers, a decrease in levels of basal NO can occur over time. Reduced NO levels can result in increased BACE-1 expression and reduced BACE-2 expression. More BACE-1 then becomes available to cleave APP into Aβ, and Aβ levels increase. A can then be secreted out of the cell to aggregate into amyloid plaques, and soluble Aβ levels increase within the cell. Internalized Aβ can inhibit NO release by the cell, which then can create a vicious cycle causing NO levels to be further decreased, lessening regulation of the BACE genes, which again increases the production of Aβ. Simultaneously, Aβ can promote a chronic and progressively increasing inflammatory reaction, initiating both vascular and neural damage. As the pathology of AD continues, NO levels can decrease to a point where hypoperfusion of the brain becomes chronically destructive. In brain cells, oxidative stress can increase, and neurons can undergo apoptosis. The result can be an overall decrease in neuronal function, producing memory loss, cognitive disorders, and other typical symptoms of AD.

Example 11

Modulation of the Ubiquitin-Proteasome Complex Via Morphine Coupled NO Release

The following experiments were performed to determine if morphine and NO play a role in the prevention of cellular stress via protein metabolism. In particular, the following experiments were performed to determine if morphine, via stimulating the production of NO, protects neural cells by attenuating the induction of cellular stress and imbalances in protein metabolism.

Methods and Materials

The human SK-N-SH neuroblastoma cell line (ATCC #HTB-11) was used as a cellular model. Cells were propagated in Minimum Essential Medium alpha (MEMα) with 10% fetal bovine serum (FBS), 2% penicillin/streptomycin, 1.5 g/L NaHCO$_3$, and 1.0 mM pyruvic acid. A 5% CO$_2$ incubator (NAPCO) at 37° C. was used for maintenance of temperature and pH. A trypsin-EDTA solution (0.25% trypsin, 0.03% EDTA) was used to aspirate and pellet the adherent cells (400 G for 5 minutes at room temperature). When needed, cells were plated in 6- or 12-well plates using a hemocytometer (2×10$^5$ cells/well in 6-well plates or 1×10$^5$ cells/well in 12-well plates). Experimental manipulations were performed under sterile conditions under a lamina airflow hood after cells had adhered to the bottom of the plates.

Compounds were weighed accurately using an atomic balance and eluted with solvent under sterile conditions. Rotenone (Sigma), a mitochondrial complex I inhibitor, and IFNγ (Endogen) were used to stimulate oxidative and inflammatory stress. Morphine sulfate (Sigma) was obtained in solution along with naloxone (a mu3 opiate receptor antagonist) and L-NAME (an NO synthase inhibitor).

Cell viability was determined via Trypan blue exclusion. An inverted light microscope (Nikon) with a phase-contrast filter was used to observe the cells. Pictures of the cells were taken via a digital camera (Optronix) attached to the microscope ocular. Images were uploaded onto ImagePro Plus Software (Applied Biosystems), where cell viability was calculated based on both the number of cells covering the field and the cells that present as dead from the stain. In addition, ImagePro Plus was used for determining cellular morphology. The area and perimeter were found and used in the formula $(4\pi*\text{Area})/(\text{Perimeter})$, resulting in a value between 0 (a straight line) and 1 (a perfect circle).

Isolation of total RNA was performed via RNA MiniPrep Kit (QIAGEN). Concentration of RNA was determined via GeneQuant II Spectrophotometer (Pharmacia Biotech) by multiplying A260 value with dilution factor and nucleic acid constant (0.04). Agarose gel electrophoresis (1%) was used to check for RNA quality.

RT and PCR reactions were performed in GeneAmp PCR System 9700 (Applied Biosystems) using reverse transcriptase and Taq DNA Polymerase. Forward and reverse gene specific-primers for various subunits of the 20S proteasome and immunoproteasome were either obtained from the literature or designed through Primer Express Software 2.0 (Applied Biosystems) (Table 4). NMDA receptor subunit primers were also designed (Table 4). NMDA receptor expression was used as a marker of neurodegenerative disease.

TABLE 4

Gene Specific Forward and Reverse Primers

| Primer Name | Forward Primer (5'→ 3') | Reverse Primer (5'→ 3') | Fragment Size |
| --- | --- | --- | --- |
| 20S Proteasome LMP7 Subunit (β5i) | CTCGCCTTCAAGTTCCAGCA (SEQ ID NO: 13) | TGCAGCAGGTCACTGACATC (SEQ ID NO: 14) | 483 bp |
| 20S Proteasome X Subunit (β5) | AGAGACCGCTACCGGTGAACC (SEQ ID NO: 15) | TGCAGCAGGTCACTGACATC (SEQ ID NO: 14) | 245 bp |
| 20S Proteasome C2 Subunit (α) | AGATACCAACACAACGATATG (SEQ ID NO: 16) | CTCTCCAAGTAAGTACGAGC (SEQ ID NO: 17) | 230 bp |
| 20S Proteasome C3 Subunit (α) | TCAGGTGGTGTTCGTCCATT (SEQ ID NO: 18) | TTCAAAGCTTTCCTTTAGGGTT (SEQ ID NO: 19) | 220 bp |
| NMDA NR1 Subunit | GATGTCTTCCAAGTATGCGGA (SEQ ID NO: 20) | GGGAATCTCCTTCTTGACCAG (SEQ ID NO: 21) | 667 bp |
| NMDA NR2B Subunit | CCCAGCATTGGCATTGCTGTC (SEQ ID NO: 22) | CATGATGTTGAGCATTACGGA (SEQ ID NO: 23) | 394 bp |
| β-actin Reference Gene | GTGGGGCGCCCCAGGCACCA (SEQ ID NO: 24) | CTCCTTAATGTCACGCACGATT (SEQ ID NO: 25) | 557 bp |

All primers were optimized for annealing temperatures and cycles (Table 5). Gel electrophoresis (2% agarose, 0.01% ethidium bromide) was performed and analyzed using a UV transilluminator (UVP) and GelPro Analyzer Software (Applied Biosystems). Relative band intensity was normalized with β-Actin reference gene.

TABLE 5

Primer Optimization

| Primer Name | Denaturation | Annealing 30 sec | Extension | Number of Cycles |
| --- | --- | --- | --- | --- |
| 20S Proteasome LMP7 Subunit (β5i) | 95° C. 30 sec | 57° C. | 72° C. 1 min | 32 |
| 20S Proteasome X Subunit (β5) | | 57° C. | | 30 |
| 20S Proteasome C2 Subunit (α) | | 55° C. | | 35 |
| 20S Proteasome C3 Subunit (α) | | 55° C. | | 35 |
| NMDA NR1 Subunit | | 55° C. | | 35 |
| NMDA NR2B Subunit | | 65° C. | | 35 |
| β-actin Reference Gene | | 55° C. | | 25 |

To determine protein concentrations, protein was harvested using the following buffer: 20 mM Hepes (Sigma), 100 mM NaCl (Fisher), 10 mM NaF (Sigma), 1% Triton X-100 (Sigma), 1 mM sodium orthovanadate (Sigma), 10 mM EDTA (Sigma), pH 7.4, 0.1% protease inhibitor cocktail (Sigma), and ddH$_2$O. Homogenized samples were spun in an ultracentrifuge at 10,000 G for 20 minutes at 4° C. Concentration was determined via the Bradford assay (Bio-Rad) using bovine serum albumin (BSA, Sigma) for standard curve. To eliminate any potential pipetting error, samples and standards were read in triplicate.

Western blotting was performed as follows. SDS-polyacrylamide gels (12% for separation and 5% for stacking) were made using the Mini Trans-Blot Cell (Bio-Rad). Based on the concentrations from the protein concentration determination assay, the proteins were mixed with 2× Protein Loading Buffer (0.2M DTT) for a final volume of 24 µL. Tris-Glycine Electrophoresis Buffer (1×) was used in SDS-PAGE, and proteins were separated at constant amperage (35 mA).

Subsequent protein transfer to a nitrocellulose membrane involved use of the Mini Trans-Blot Cell apparatus run at constant voltage (100V) for 40 minutes. Overnight blocking was performed in 5% non-fat dry milk dissolved in TBST buffer at 4° C. Primary and secondary antibodies were used (Table 6). The primary incubation lasted for 1 hour and was followed by 4 washes with TBST buffer, 10 minutes each. The secondary incubation lasted for 1 hour and was followed by 3 washes with TBST buffer, 15 minutes each.

TABLE 6

Primary and Secondary Antibodies

| | Type | Dilution | Company |
|---|---|---|---|
| Primary Antibody | | | |
| 20S Proteasome X (β5) Subunit | Rabbit Polyclonal | 1:1000 | Affinity Bioreagents, Inc. |
| Immunoproteasome LMP7 (β5i) Subunit | Rabbit Polyclonal | 1:1000 | Affinity Bioreagents, Inc. |
| Ubiquitin (whole molecule) | Mouse Monoclonal | 1:100 | Santa Cruz Biotechnologies, Inc. |
| Secondary Antibody | | | |
| HRP Conjugated | Anti-Mouse | 1:12500 | Pierce, Inc. |
| HRP Conjugated | Anti-Rabbit | 1:12500 | Sigma-Aldrich, Inc. |

Substrate (Pierce) was administered as a means of stimulating chemiluminescence. Blots were developed and subsequently analyzed for relative band intensity using Gel-Pro software (Applied Biosystems).

Proteasome function assays were performed in an effort to examine the modulation in levels of protein degradation. Fluorometric assays were performed for both the chymotrypsin activity of the 26S proteasome as well as activity of the whole 20S proteasome using procedures adapted from Kotamraju et al. (Proc. Natl. Acad. Sci. USA, 100:10653-8 (2003)). Excitation at 365 nM and emission at 460 nM of the fluorogenic compound, 4-amido-7-methylcoumarin (AMC), were measured using a Spectrofluoroscence Detector (McPherson).

Nitric oxide release was determined upon administration of morphine sulfate to the neuroblastoma cells through the use of the Apollo 4000 free radical detector (WPI Sarasota, Fla.). The amperometric NO probe was calibrated based upon a solution of 0.2M CuCl$_2$ using the NO donor, S-nitroso-N-acetyl-L-penicillamine (SNAP) at concentrations of 10 µM, 20 µM, 40 µM, and 80 µM. To make sure morphine was not reacting with the probe, negative controls were performed using PBS.

All data from cell viability and cell morphology experiments was normalized with the standard error of the mean (±SEM). RT-PCR data was normalized with β-actin reference gene expression and, subsequently, ±SEM from the average obtained over the course of three trials. Western blotting involved densitometric analysis of band intensity based expression of protein. Functional assays for proteasome activity were normalized with ±SEM for 3 trials. For all experiments, two-variable t-tests were used to compare levels of significance between treatments.

Results

Morphine-stimulated, cNOS-derived NO release occurred in neuroblastoma cells (FIGS. 43A and B; peak value of 22.3 nM±0.85, p<0.001 compared to baseline 2 nM NO, baseline was insignificant when compared to negative controls). Naloxone ($10^{-6}$ M) and L-NAME (le M) blocked the NO release induced by $10^{-6}$ M morphine (3.2 nM NO and 0.3 nM NO, respectively).

Rotenone, an agent inducing oxidative stress at the intracellular level, stimulated cellular death when used to treat neuroblastoma cells ($LD_{50}$=30 nM). Cell viability experiments (FIGS. 44A and B) involved a 24-hour pretreatment of morphine sulfate (5 µM) and a subsequent 48-hour incubation with rotenone (30 nM). This resulted in a significant level of protection (p<0.01) between the rotenone-treated cells, which exhibited about 45% confluency, and the morphine-pretreated cells, which exhibited an increase to about 78% confluency.

Cellular morphology was used as an indicator of cell activation and was calculated via the Form Factor (FF; FF=1 is a round cell that is immobile and less than 0.7 indicates an elongated adhering cell; FIG. 44C). The FF determination demonstrated that morphine produced a neuroprotective effect (cells were round and inactive) against the toxicity of a 24-hour pretreatment with rotenone (p<0.003; FIG. 44C). A reversal in morphine neuroprotection was achieved via treatments with naloxone (10 µM), an opiate receptor antagonist, and L-NAME (10 µM), an inhibitor of NO, suggesting that NO was involved with morphine's protective action.

The following experiments were designed to determine the molecular events involved in the protective process. Relative band intensity was measured in arbitrary units (AU) through a computer-assisted imaging system. Rotenone was examined for its ability to induce an imbalance in the expression of a molecular marker for neurodegenerative disease, the NMDA receptor. A rotenone-induced imbalance was observed in the NMDA receptor (NR1 and NR2B subunits) mRNA expression, and morphine reversed the imbalance of this indicator. NR1 expression in controls (1.57±0.072 AU) was decreased with rotenone to 1.22±0.010 AU ($LD_{50}$, 30 nM) and 1.21±0.028 AU (40 nM; p<0.003 when compared to control) (FIG. 45A). Morphine (5 µM) significantly increased NR1 expression to 1.40±0.056 AU at the $LD_{50}$ of rotenone (p<0.035). NR2B expression was 0.98±0.02 in the control compared to 1.22±0.08 AU and 1.49±0.02 AU (p<0.001 for both compared to control) with 30 nM ($LD_{50}$) and 40 nM rotenone, respectively (FIG. 45B). A significant decrease in NR2B expression to 1.09±0.06 AU and 1.17±0.04 AU with morphine (5 µM) administration was observed with 30 nM and 40 nM of rotenone, p<0.042 and p<0.018, respectively, compared to rotenone values.

Examination of expression of various subunits of the 20S proteasome initially involved testing for mRNA expression of the proteasomal non-catalytic C2 and C3 alpha subunits as well as catalytic X (β5) subunit since this may be the sight of the effect. No change in the level of expression of the alpha subunits was observed.

Regulation of X subunit expression was observed with rotenone and morphine, indicating neuroprotection (FIG. 46). Morphine increased the level of expression of the proteasomal X subunit in a dose dependent manner at both 4 and 24 hours ($p<0.014$ at 4 hours, and $p<0.009$ from $0.716\pm0.015$ AU control to $0.868\pm0.007$ AU 5 µM at 24 hours). Morphine (5 µM) induced neuroprotection was observed in a dose dependent decrease in X subunit expression, which was significant when compared to treatments with rotenone alone ($p<0.01$ at 4 hours and $p<0.012$ at 24 hours).

Morphine also stimulated a decrease in mRNA expression of the LMP7 immunoproteasome subunit, blocking a slight increase in LMP7 mRNA caused by rotenone (FIG. 47). There was a significant dose dependent decrease in LMP7 expression from the value of the rotenone control at 1 µM morphine ($p<0.026$) and to $0.792\pm0.001$ AU at 5 µM morphine ($p<0.018$).

The data above, regarding mRNA expression, was reinforced through Western blotting detection of the X subunit protein levels. Relative band intensity was measured in arbitrary units through a computer-assisted imaging system. A time course with morphine treatment (FIG. 48A), indicates a dose dependent significant increase in the level of expression of the X subunit after morphine administration (1 µM and 5 µM) at 24 hours ($p<0.01$ with 1 µM compared to control and $p<0.001$ when 5 µM). The expression of the X subunit also was examined after concomitant rotenone treatments and morphine exposure (FIG. 48B). The previous mRNA results (from FIG. 46) were confirmed by changes in protein expression, showing evidence of morphine neuroprotection. The control band intensity of 149 AU increased to 162 AU and 188 AU (1 µM and 5 µM morphine, respectively). Rotenone caused an increase in expression from control value to 182 AU. There was a decrease exhibited in morphine-induced neuroprotection from 182 AU to 168 AU (1 µM morphine) and subsequently to 154 AU ($p<0.028$).

Experiments determining the modulation of the 20S proteasome and chymotrypsin activity of the 26S proteasome revealed a differential regulation (FIG. 49). Rotenone decreased the activity of the chymotrypsin functional 26S active site (control value of $236\pm4.8$ µM to $221\pm4.8$ µM; $p<0.043$), whereas morphine (5 µM) increased the control value to $277\pm8.0$ µM ($p<0.021$). Concomitant treatment of morphine and rotenone resulted in a restoring of chymotrypsin activity ($p<0.050$; FIG. 49A). These results demonstrate that, through the increase in 26S chymotrypsin activity, morphine was able to prevent the need for increased 20S activity by decreasing 20S activity (FIG. 49B) involved in degradation of oxidized and misfolded proteins.

Western blotting revealed that morphine caused a dose dependent increase in the levels of free ubiquitin from the control value of 44 AU to 64 AU and 125 AU (1 µM and 5 µM, respectively). A slight decrease in free ubiquitin, although not significant, was observed with rotenone, which was reversed significantly with concomitant administration of morphine and rotenone ($p<0.039$; FIG. 50). The increase in free ubiquitin expression—ubiquitin not bound to proteins—stimulated by morphine and subsequent counteraction against the decreased expression caused by rotenone provides further evidence into the functional value of morphine neuroprotection.

To understand the effects of neuroinflammation, interferon (IFN)$_\gamma$ was used to simulate an immune response, i.e., proinflammatory. IFNγ did not cause significant cellular death. However, IFNγ did cause changes in cellular morphology indicative of the neuroinflammatory stress. A FF increase from $0.54\pm0.02$ to $0.76\pm0.02$ was observed between control and IFNγ treatments ($p<0.014$). A decrease in the FF resulted from concomitant treatment of both morphine and IFNγ, (FF $0.76\pm0.02$ to $0.58\pm0.01$ reveals cellular elongation). A non-significant reversal in morphine neuroprotection was observed with treatments of naloxone and L-NAME.

IFNγ induction of LMP7 was examined IFN-γ caused an increase in LMP7 expression after 24 hours from the control value of $0.29\pm0.01$ to $0.93\pm0.06$ ($p<0.001$), demonstrating neuroinflammatory stress. Morphine blocked the LMP7 increase induced by IFNγ ($p<0.034$; FIG. 51).

Western blotting for the LMP7, after IFNγ stimulated its expression, revealed that morphine exposure blocked this action at both 36 and 48 hours (FIG. 52; $p<0.001$ for comparison between treatment #2 and treatment #3; $p<0.001$ for comparison between treatment #5 and treatment #6).

These results demonstrates that morphine exerts neuroprotective actions following the administration of rotenone, a compound that initiates cellular oxidative stress thereby inducing a high rate of cell death. Morphine exerts the same protective mechanism in regard to immune tissues activated by IFN-γ, which also exerts deleterious actions. Additionally, morphine was shown to stimulate production of cNOS-derived NO in neurobastoma cells. Taken together, morphine appears to exert its protective actions via constitutive NO release, where NO may act as an antioxidant.

Rotenone, an inhibitor of mitochondrial complex I, stimulates production of ROS and causes cell death. Cells treated with morphine prior to rotenone exposure, exhibit significant amelioration of cell death. Moreover, rotenone was able alter the molecular imbalance between NR1 and NR2B subunits, demonstrating that cellular stress or oxidative damage occurred. Morphine corrected this imbalance.

In regard to the ubiquitin-proteasome complex mRNA and protein expression, morphine increased X subunit expression in a dose dependent manner. Interestingly, rotenone also stimulated an increase in X subunit expression, which was blocked by morphine, causing a shift in levels of expression back to the control. In addition, experiments were performed to test for the expression of LMP7, an immunoproteasome catalytic subunit. These experiments revealed an increase in LMP7 mRNA expression that was blocked by morphine, further signifying morphine induced neuroprotection not only against oxidative stress, but also inflammatory stress as well.

Proteasome function assays were performed to observe proteasome enzymatic activity, i.e., actual protein degradation. Rotenone caused an increase in activity of the 20S proteasome along with a decrease in activity of the 26S chymotrypsin active site. The decreased 26S chymotrypsin activity was most probably due to increased surface hydrophobicity of oxidized proteins, preventing intake into the 19S regulatory particle. Thus, 20S activity increased in order to degrade oxidized proteins. In this regard, morphine stimulated an increase in 26S chymotrypsin activity and a decrease in 20S activity. This differential effect may have been achieved through the nitration of oxidized proteins. NO may have marked proteins for degradation via the chymotrypsin active site, specific for nitrated proteins. As more proteins were degraded through the 26S proteasome, there was a decrease in 20S activity because of the reduced quantity of oxidized proteins. Thus, from the proteasome function assays, morphine neuroprotection can be attributed not only to prevention of ROS, but also through specific targeting of proteins for degradation at the chymotrypsin active site on the 26S proteasome.

Examining free ubiquitin, a marker for protein degradation, revealed lower levels after treatment with rotenone because more ubiquitin molecules were used to mark oxidized proteins. Interestingly, morphine caused a dose dependent increase in ubiquitin protein expression. This implies that, upon treatment with morphine, fewer proteins were oxidized and misfolded, further supporting morphine stimulated neuroprotection.

Examination of the LMP7 mRNA and protein expression revealed that morphine inhibited the induction of this immunoproteasome subunit. Western blotting revealed that IFN-γ caused both a decrease in X expression, as well as an increase in LMP7 expression. This effect was blocked by morphine after IFN-γ exposure.

Taken together, these results demonstrate that morphine, via NO, produces neuroprotection not just by acting as an antioxidant, but also by targeting oxidized and misfolded proteins for degradation via the 26S proteasome. Thus, endogenous morphine signaling may normally function to overcome cellular stress processes, revealing a new pharmacological way to treat neurodegenerative disorders.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for inducing nitric oxide release from cells in a mammal, said method comprising administering, to said mammal, a composition in an amount, at a frequency more frequent than once a week, and for a duration longer than one month, wherein said composition comprises one or more agents selected from the group consisting of reticuline, norlaudanosoline, and salutaridine, and wherein said amount of said composition results in less than 1 mg of said one or more agents being administered to said mammal per kg of body weight of said mammal per day.

2. The method of claim 1, wherein said cells are immune cells.

3. The method of claim 1, wherein said mammal is a human.

4. The method of claim 1, wherein said composition further comprises morphine in an amount that results in less than 0.05 mg of said morphine being administered to said mammal per kg of body weight of said mammal per day.

5. The method of claim 1, wherein said composition is in the form of a tablet.

6. The method of claim 1, wherein said composition comprises selenium.

7. The method of claim 1, wherein said composition comprises L-arginine.

8. The method of claim 1, wherein said composition comprises a calcium source.

9. The method of claim 1, wherein said amount of said composition results in less than 0.5 mg of said one or more agents being administered to said mammal per kg of body weight of said mammal per day.

10. The method of claim 1, wherein said amount of said composition results in less than 0.05 mg of said one or more agents being administered to said mammal per kg of body weight of said mammal per day.

11. The method of claim 1, wherein said frequency is more frequent than four times a week.

12. The method of claim 1, wherein said frequency is between two and five times a day.

13. The method of claim 1, wherein said frequency is once a day.

14. The method of claim 1, wherein said duration is longer than two months.

15. The method of claim 1, wherein said duration is longer than three months.

16. The method of claim 1, wherein said composition comprises reticuline, norlaudanosoline, and salutaridine.

* * * * *

UNITED STATES PATENT AND TRADEMARK OFFICE
CERTIFICATE OF CORRECTION

PATENT NO. : 8,865,696 B2  
APPLICATION NO. : 13/924211  
DATED : October 21, 2014  
INVENTOR(S) : George B. Stefano et al.

Page 1 of 1

It is certified that error appears in the above-identified patent and that said Letters Patent is hereby corrected as shown below:

On the Title Page

Page 2, Column 2 (Other Publications), line 15 (approx.), please delete "sequency" and insert -- sequence --, therefor;

Page 2, Column 2 (Other Publications), line 19-20 (approx.), please delete "ofμ3," and insert -- of μ3, --, therefor.

In the Specification

Column 1, line 7 (approx.), please delete "Oct. 4, 2010," and insert -- Oct. 14, 2010, --, therefor.

Signed and Sealed this  
Tenth Day of February, 2015

Michelle K. Lee  
*Deputy Director of the United States Patent and Trademark Office*

SEQUENCE LISTING

```
<160> NUMBER OF SEQ ID NOS: 25

<210> SEQ ID NO 1
<211> LENGTH: 264
<212> TYPE: DNA
<213> ORGANISM: Mytilus edulis
<220> FEATURE:
<221> NAME/KEY: misc_feature
<222> LOCATION: 1, 2, 113, 133, 155, 249, 250
<223> OTHER INFORMATION: n= a, c, g, or t

<400> SEQUENCE: 1
nnccaagggg aaccctgaga gcagcttcaa tgatgagaac ctgcgcatag tggtggctga      60
cctgttctct gccgggatgg tgaccacctc gaccacgctg gcctggggca tcntgctcat     120
gatcatacat ctnggatgtg cagcgccggg tcaanaggag attgactacg tgatagggca     180
ggtgcggaga ccagagatgg gtgaccaggc tacatgccct acaccactgc cgtgattcat     240
gaggtgcann gctttgggga catc                                             264

<210> SEQ ID NO 2
<211> LENGTH: 265
<212> TYPE: DNA
<213> ORGANISM: Homo sapiens

<400> SEQUENCE: 2
ggccaagggg aaccctgaga gcagcttcaa tgatgagaac ctgcgcatag tggtggctga      60
cctgttctct gccgggatgg tgaccacctc gaccacgctg gcctggggcc tcctgctcat     120
gatcctacat ccggatgtgc agcgccgtgt ccaacaggag atcgacgacg tgatagggca     180
ggtgcggcga ccagagatgg gtgaccaggc tcacatgccc tacaccactg ccgtgattca     240
tgaggtgcag cgctttgggg acatc                                            265

<210> SEQ ID NO 3
<211> LENGTH: 28
<212> TYPE: DNA
<213> ORGANISM: Artificial Sequence
<220> FEATURE:
<223> OTHER INFORMATION: Primer

<400> SEQUENCE: 3
aggtgtgtct cgaggagccc atttggta                                         28

<210> SEQ ID NO 4
<211> LENGTH: 24
```

```
<212> TYPE: DNA
<213> ORGANISM: Artificial Sequence
<220> FEATURE:
<223> OTHER INFORMATION: Primer

<400> SEQUENCE: 4
gcagaaagcc cgactcctcc ttca                                          24

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
ggccaagggg aaccctgaga                                               20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
ggtcataccc aggggacga                                                20

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
tgactgggaa caccccataa ct                                            22

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
cgagcgcctc agtgttactc t                                             21

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
agccatcctc cttgtcttaa tcg                                           23

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
```

```
tctggcggaa ataacctca a                                              21

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
tttcgtgctc tgagcactgg                                               20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
cttgccattc ctggacccaa                                               20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
ctcgccttca agttccagca                                               20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
tgcagcaggt cactgacatc                                               20

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
agagaccgct accggtgaac c                                             21

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
agataccaac acaacgatat g                                             21

<210> SEQ ID NO 17
<211> LENGTH: 20
<212> TYPE: DNA
<213> ORGANISM: Artificial Sequence
```

```
<220> FEATURE:
<223> OTHER INFORMATION: Primer

<400> SEQUENCE: 17
ctctccaagt aagtacgagc                                               20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
tcaggtggtg ttcgtccatt                                               20

<210> SEQ ID NO 19
<211> LENGTH: 22
<212> TYPE: DNA
<213> ORGANISM: Artificial Sequence
<220> FEATURE:
<223> OTHER INFORMATION: Primer

<400> SEQUENCE: 19
ttcaaagctt tcctttaggg tt                                            22

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
gatgtcttcc aagtatgcgg a                                             21

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
gggaatctcc ttcttgacca g                                             21

<210> SEQ ID NO 22
<211> LENGTH: 21
<212> TYPE: DNA
<213> ORGANISM: Artificial Sequence
<220> FEATURE:
<223> OTHER INFORMATION: Primer

<400> SEQUENCE: 22
cccagcattg gcattgctgt c                                             21

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23
catgatgttg agcattacgg a                                             21
```

```
<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
gtggggcgcc ccaggcacca                                               20

<210> SEQ ID NO 25
<211> LENGTH: 22
<212> TYPE: DNA
<213> ORGANISM: Artificial Sequence
<220> FEATURE:
<223> OTHER INFORMATION: Primer

<400> SEQUENCE: 25
ctccttaatg tcacgcacga tt                                            22
```